United States Patent
Dong et al.

(10) Patent No.: US 11,406,616 B2
(45) Date of Patent: Aug. 9, 2022

(54) LIPIDS WITH ODD NUMBER OF CARBON ATOMS AND THEIR USE AS PHARMACEUTICAL COMPOSITION OR NUTRITIONAL SUPPLEMENT

(71) Applicant: SunRegen Healthcare AG, Reinach Basel-Land (CH)

(72) Inventors: Yuhong Dong, Basel-land (CH); Chun-Hsiung Chang, Taiwan (TW); Sheng-Tang Lin, Taiwan (CN)

(73) Assignee: SunRegen Healthcare AG, Reinach Basel-Land (CH)

( * ) Notice: Subject to any disclaimer, the term of this patent is extended or adjusted under 35 U.S.C. 154(b) by 773 days.

(21) Appl. No.: 16/307,663

(22) PCT Filed: Jun. 6, 2017

(86) PCT No.: PCT/CN2017/087341
§ 371 (c)(1),
(2) Date: Dec. 6, 2018

(87) PCT Pub. No.: WO2017/211274
PCT Pub. Date: Dec. 14, 2017

(65) Prior Publication Data
US 2019/0255129 A1    Aug. 22, 2019

Related U.S. Application Data

(60) Provisional application No. 62/347,103, filed on Jun. 8, 2016.

(51) Int. Cl.
| | | |
|---|---|---|
| *A61K 31/225* | (2006.01) | |
| *A61P 21/00* | (2006.01) | |
| *A61P 9/10* | (2006.01) | |
| *A61P 25/28* | (2006.01) | |
| *A61P 11/06* | (2006.01) | |
| *A61P 25/02* | (2006.01) | |
| *A61P 3/10* | (2006.01) | |
| *A61P 13/12* | (2006.01) | |
| *A61K 31/215* | (2006.01) | |
| *A61K 36/11* | (2006.01) | |
| *A61Q 19/08* | (2006.01) | |
| *A61P 25/00* | (2006.01) | |
| *A61K 31/22* | (2006.01) | |

(52) U.S. Cl.
CPC .......... *A61K 31/225* (2013.01); *A61K 31/215* (2013.01); *A61K 31/22* (2013.01); *A61K 36/11* (2013.01); *A61P 3/10* (2018.01); *A61P 9/10* (2018.01); *A61P 11/06* (2018.01); *A61P 13/12* (2018.01); *A61P 21/00* (2018.01); *A61P 25/00* (2018.01); *A61P 25/02* (2018.01); *A61P 25/28* (2018.01); *A61Q 19/08* (2013.01); *Y02A 50/30* (2018.01)

(58) Field of Classification Search
None
See application file for complete search history.

(56) References Cited

U.S. PATENT DOCUMENTS

| | | |
|---|---|---|
| 8,426,468 B2 | 4/2013 | Henderson |
| 9,468,229 B2 | 10/2016 | Mochel et al. |
| 2007/0123588 A1 | 5/2007 | Charles |
| 2011/0201558 A1 | 8/2011 | Roe et al. |
| 2011/0207819 A1 | 8/2011 | Boll |
| 2011/0301238 A1 | 12/2011 | Borges |
| 2016/0051506 A1 | 2/2016 | Boll |

FOREIGN PATENT DOCUMENTS

| | | |
|---|---|---|
| CA | 1 244 722 | 11/1988 |
| CN | 1514723 | 7/2004 |
| CN | 101879156 | 11/2010 |
| CN | 102781438 | 11/2012 |
| CN | 103641713 | 3/2014 |
| CN | 105381182 | 3/2016 |
| DE | 3032300 | 4/1982 |
| EP | 1 292 294 | 3/2009 |
| EP | 1 385 500 | 7/2010 |
| EP | 2 319 508 | 5/2011 |
| EP | 2 749 281 | 7/2014 |
| EP | 2 519 234 | 6/2017 |

(Continued)

OTHER PUBLICATIONS

Hinton, et al., The New England Journal of Medicine, 316:485. (Year: 1986).*
Moschos, et al., Current Alzheimer Research, 9:1. (Year: 2012).*
Berisha, et al., IOVS, 48:2285. (Year: 2007).*
International Search Report mailed in PCT/CN2017/087341 dated Sep. 26, 2017.
Written Opinion of the International Searching Authority mailed in PCT/CN2017/087341 dated Sep. 29, 2017.

(Continued)

*Primary Examiner* — Michael Barker
(74) *Attorney, Agent, or Firm* — Grüneberg and Myers PLLC

(57) ABSTRACT

Provided are the use of lipids bearing fatty acids with an odd number of carbon atoms as pharmaceuticals or nutritional supplement. In particular, such lipids are used in the treatment and/or prevention of neurodegenerative diseases, optic and retinal degenerative diseases, demyelinating diseases, neuromuscular disorders and muscular dystrophy, brain or spinal cord nerve injury, amyloid related diseases, other chronic diseases selected from kidney diseases, diabetes or asthma, but also a functional food or food supplement for anti-aging or life-span prolongation and brain function improvement for human and/or animals. Moreover, provided is the herb *Ophioglossum* which can be used for the treatment and/or prevention of said diseases.

3 Claims, 19 Drawing Sheets

(56) References Cited

FOREIGN PATENT DOCUMENTS

| | | |
|---|---|---|
| JP | H02-247125 | 10/1990 |
| JP | 3558351 | 5/2004 |
| JP | 2005-89375 | 4/2005 |
| JP | 2013516416 | 5/2013 |
| JP | 2016088885 | 5/2016 |
| KR | 100829729 | 5/2008 |
| WO | 2001/95914 | 12/2001 |
| WO | 2002/083120 | 10/2002 |
| WO | 2002/083122 | 10/2002 |
| WO | 2008/039855 | 4/2008 |
| WO | 2008/068230 | 6/2008 |
| WO | 2009/055933 | 5/2009 |
| WO | 2010/057804 | 5/2010 |
| WO | 2011/082111 | 7/2011 |
| WO | 2011/159634 | 12/2011 |
| WO | 2015/073803 | 5/2015 |
| WO | 2015/110977 | 7/2015 |
| WO | 2017/093060 | 6/2017 |

OTHER PUBLICATIONS

Aguilaniu et al., "Asymmetric Inheritance of Oxidatively Damaged Proteins during Cytokinesis," Science, vol. 299, 2003, pp. 1751-1753.
Brown, "Delicious, Nutritious, and a Colorful Dish for the Holidays," AgResearch Magazine, vol. 62, No. 10, Nov. 2014, pp. 14-15.
Dember, "Amyloidosis-Associated Kidney Disease,", J. Am. Soc. Nephrol, vol. 17, Iss. 12, 2006, pp. 3458-3471.
Deshpande et al., "Different Conformations of Amyloid β Induce Neurotoxicity by Distinct Mechanisms in Human Cortical Neurons," vol. 26, Iss. 22, 2006, pp. 6011-6018.
Fahr, "Voigt Pharmazeutische Technologie," 2015, Stuttgart, ISBN: 978-3-7692-6194-3, pp. V, VII-XXI, XXIII, XXIV, and 1-5.
"Functional Foods Research in ARS," AgResearch Magazine, vol. 58, No. 6, Jul. 2010.
Grad et al., "From molecule to molecule and cell to cell: Prion-like mechanisms in amyotrophic lateral sclerosis," Neurobiology of Disease, vol. 77, 2015, pp. 257-265.
Guo et al., "Targeting amyloid-β in glaucoma treatment," Proc Natl Acad Sci USA, vol. 104, Iss. 33, 2007, pp. 13444-13449.
Lorenzo et al., "Pancreatic islet cell toxicity of amylin associated with type-2 diabetes mellitus," Nature, vol. 368, Iss. 6473, 1994, pp. 756-760.
Petschow et al., "*Susceptibility of Helicobacter pylori to Bactericidal Properties of Medium-Chain Monoglycerides and Free Fatty Acids*," Antimicrobial Agents and Chemotherapy, Feb. 1996, p. 302-306, vol. 40. No. 2.
Sweeney et al., "Mechanistic and Structural Insights into the Prion-Disaggregase Activity of Hsp104," J. Mol. Biol. vol. 428, Iss. 9, 2016, pp. 1870-1885.
Zhang et al., "Chemical Constituents of Ophioglossum thermale Kom." Nat Prod Res Dev, vol. 22, Iss. 6, 2010, pp. 1006-1008, with English language abstract.
Zhang et al., "Chemical Constituents of Ophioglossum thermale Kom." Nat Prod Res Dev, vol. 22, Iss. 6, 2010, pp. 1006-1008 (previously filed on Dec. 6, 2018; submitting English-language translation, 4 pp.).
Extended Search Report dated Jan. 3, 2020 in European Application No. 17809713.5, 9 pages.
Written Opinion dated May 28, 2018 in International Application No. PCT/EP2017/072849, 7 pages.
Japanese Office Action dated Feb. 10, 2022 in Japanese Application No. 2021-067485, with English translation, 6 pages.
Search Report dated Mar. 3, 2020 in Singaporean Application No. 11201810580P, 3 pages.
Written Opinion dated Mar. 3, 2020 in Singaporean Application No. 11201810580P, 6 pages.
Francis et al., Journal Inherited Metabolic Disease; 2013, 37(3):369-381.
Park et al., PLos One; 2014, 9(10):e109527 (pp. 1-22).

\* cited by examiner

Left: AβO control; Right: compound C at 320nM added at 48 hours before adding AβO Left: AβO control; Right: herb B at 32 ng/mL added at 48 hours before adding AβO

LIPIDS WITH ODD NUMBER OF CARBON ATOMS AND THEIR USE AS PHARMACEUTICAL COMPOSITION OR NUTRITIONAL SUPPLEMENT

This application is a National Stage entry under § 371 of International Application No. PCT/CN2017/087341, filed on Jun. 6, 2017, and claims priority to U.S. Application No. 62/347,103, filed on Jun. 8, 2016.

RELATED APPLICATION

This application claims the benefit of priority from U.S. Provisional Application Ser. No. 62/347,103, filed on Jun. 8, 2016, the entire content of each of which is incorporated herein by reference in its entirety.

FIELD OF THE INVENTION

The present invention relates to lipids and their use as pharmaceutical composition or nutritional supplement. In particular, the invention provides novel use of lipids bearing fatty acids with an odd number of carbon atoms, particularly tripentadecanoin, that exhibit potent neuroprotective, anti-apoptotic, neuro-rescuing, and axon-outgrowth effects, which are useful as pharmaceuticals or nutritional supplement for the treatment and/or prevention of neurodegenerative diseases, optic and retinal degenerative diseases, demyelinating diseases, neuromuscular disorders and muscular dystrophy, brain or spinal cord nerve injury, amyloid related diseases, other chronic diseases or conditions selected from kidney diseases, diabetes, asthma and dyspnea, but also a functional food or food supplement for anti-aging or lifespan prolongation and brain function improvement for human. Moreover, the present invention relates to the novel use of *Ophioglossum* and/or extracts thereof in the treatment and/or prevention of said diseases and conditions.

BACKGROUND OF THE INVENTION

Hundreds of millions of people worldwide are affected by neurological disorders. Neurological disorders include diseases of the central and peripheral nervous system. In other words, the brain, spinal cord, cranial nerves, peripheral nerves, nerve roots, autonomic nervous system, neuromuscular junction, and muscles.

The current invention is related to the treatment of different neurological diseases and associated chronic diseases as detailed as below:

A. Neurodegenerative Diseases

Neurodegenerative disease is the umbrella disease term for the progressive loss of structure or function of neurons, including death of neurons. The damage or death of neurons lead to a gradual deterioration of the functions controlled by the affected part of the nervous system. The selected group of neurodegenerative disorders include Alzheimer's Disease (AD), Parkinson's disease (PD), Huntington's diseases (HD), Amyotrophic Lateral Sclerosis (ALS), Dementia, dementia with Lewy bodies (DB), frontotemporal dementia (FTD), Creutzfeldt-Jakob disease (CJD), and brain atrophy.

Most neurodegenerative diseases are also classified as proteinopathies as they are associated with the aggregation of misfolded proteins during aging process. Protein misfolding and aggregation is a major histopathologic hallmark of neurodegenerative diseases. A major histopathologic focus in all the neurodegenerative diseases is now on small protein aggregates termed oligomers. These aggregates may be the toxic species of β-amyloid, α-synuclein, prions, etc. Disposition of β-amyloid is the major component of senile plaques in Alzheimer's disease and strongly implicated in the pathogenesis of AD; tau protein is the main component of neurofibrillary tangles implicated in the pathogenesis of AD; α-synuclein can aggregate to form insoluble fibrils in pathological conditions characterized by Lewy bodies, such as Parkinson's disease, dementia with Lewy bodies, and multiple system atrophy, and is strongly implicated in the pathogenesis of PD and DLB; prion is the main component of prion diseases and transmissible spongiform encephalopathies and is strongly associated with spongiform encephalopathy (Creutzfeldt-Jakob disease).

Apoptosis, or programmed cell death, plays an important role in both physiologic and pathologic conditions. There is mounting evidence for an increased rate of apoptotic cell death in a variety of acute and chronic neurological diseases including neurodegenerative disease. Apoptosis is characterized by neuronal shrinkage, chromatin condensation, and DNA fragmentation, whereas necrotic cell death is associated with cytoplasmic and mitochondrial swelling followed by dissolution of the cell membrane. Evidence of DNA fragmentation has been found in several degenerative neurologic disorders, including AD, HD and ALS.

There is no effective treatment targeting the original causes of neurodegenerative diseases.

Dementia is defined as an acquired deterioration in cognitive abilities with memory loss as the most common symptoms. It is estimated that there are globally 35.6 million people with dementia—AD is the most common cause of dementia, accounting for 60-70% of all patients (WHO Online Q&A, February 2014). The strongest risk factor for dementia is increasing age. AD is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Increasing evidence suggests that soluble amyloid species called oligomers may cause cellular dysfunction and represent the early toxic molecule in AD. There are neuritic plaques containing β-amyloid (Aβ). Aβ is a protein of 39-42 amino acids that is derived proteolytically from a larger transmembrane protein, amyloid precursor protein (APP), when APP is cleaved by and secretases. Moreover, none of the molecules currently available efficiently target the underlying causative pathophysiological processes of the disease.

Parkinson's disease is a degenerative disorder of the central nervous system. It results from the death of dopamine-generating cells in the substantia nigra, a region of the midbrain; the cause of cell-death is unknown. Parkinson's disease is the second most common neurodegenerative disorder and manifests as bradykinesia, rigidity, resting tremor and posture instability. PD affects approximately 7 million people globally and 1 million people in the United States. The number of new cases per year of PD is between 8 and 18 per 100,000 persons-year. Levodopa has been the most widely used treatment for over 30 years but with very limited efficacy. Investigations on neuroprotection are at the forefront of PD research.

Huntington's Disease (HD) causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. There is no treatment for HD.

Amyotrophic lateral sclerosis (ALS), sometimes called Lou Gehrig's disease, is a rapidly progressive, invariably fatal neurological disease that attacks the nerve cells (neurons) responsible for controlling voluntary muscles. The disease belongs to a group of disorders known as motor neuron diseases, which are characterized by the gradual degeneration and death of motor neurons. Management of ALS attempts to relieve symptoms and extend life expectancy. Riluzole has been found to modestly improve survival by several months. The major pathological hallmark of ALS is abnormal accumulation of protein inclusions containing TDP-43, FUS or SOD1 protein. In vitro and cell line experimental evidence suggests that SOD1, TDP-43 and FUS form insoluble fibrillar aggregates. Notably, these protein aggregates can act as seeds to trigger the aggregation of native counterparts. Many evidences support the prion-like properties of major ALS-associated proteins and the possible therapeutic strategies for ALS based on a prion-like mechanism were discussed. (Grad, Leslie I.; et al. Neurobiology of Disease. 2015; 77: 257-265.)

B. Retinal and Optical Nerve Degenerative Diseases

B-1. Optic Nerve Degenerative Diseases

Optic atrophy is a condition that affects the optic nerve, which carries impulses from the eye to the brain. Optic atrophy results from damage to the optic nerve from many kinds of pathologies. The condition can cause problems with vision, including blindness, glaucoma, stroke of the optic nerve, known as anterior ischemic optic neuropathy; tumor that is pressing on the optic nerve; optic neuritis, an inflammation of the optic nerve caused by multiple sclerosis; a hereditary condition known as Leber's hereditary optic neuropathy (LHON).

Optic neuritis (ON) is inflammation of the optic nerve that can cause partial or complete vision loss. The optic nerve comprises axons that emerge from the retina of the eye and carry visual information to the primary visual nuclei, most of which is relayed to the occipital cortex of the brain to be processed into vision. Inflammation of the optic nerve causes loss of vision, usually because of the swelling and destruction of the myelin sheath covering the optic nerve. Direct axonal damage may also play a role in nerve destruction.

Dominant Optic Atrophy (DOA) is neuro-ophthalmic condition characterized by a bilateral degeneration of the optic nerves, causing insidious visual loss, typically starting during the first decade of life. The disease affects primary the retinal ganglion cells (RGC) and their axons forming the optic nerve, which transfer the visual information from the photoreceptors to the lateral geniculus in the brain. The prevalence of the disease varies from 1/10000 to 1/30000 in the rest of the world.

B-2. Retinal Degenerative Diseases

Macular degeneration, also known as age-related macular degeneration (AMD or ARMD), is a medical condition which may result in blurred or no vision in the center of the visual field. It is one of the most common causes of irreversible blindness affecting nearly 50 million individuals globally. Degenerative processes in the ageing retina and brain show striking similarities, and offers scope for identifying novel targets as well as pathogenic mechanisms. Amyloid beta, which builds up in Alzheimer's disease brains, is one the proteins accumulating in AMD, which is one of the reasons AMD is sometimes called "Alzheimer's of the eye" or "Alzheimer's of the retina". At present, the majority of AMD patients have no effective treatment.

Glaucoma, a major cause of blindness worldwide, is commonly linked to raised intraocular pressure (IOP). The precise means by which IOP may lead to the irreversible destruction of retinal ganglion cells (RGCs) is far from clear. The principal step leading to irreversible loss of vision in glaucoma is RGC apoptosis. Aβ has been reported to be implicated in the development of RGC apoptosis in glaucoma, with evidence of increased expression of Aβ in RGCs in experimental glaucoma and decreased vitreous Aβ levels (consistent with retinal Aβ deposition) in patients with glaucoma. Strong evidence from an animal model of glaucoma supporting the involvement of Aβ in glaucoma-induced apoptosis of RGCs and show that the use of agents targeting multiple phases of the Aβ pathway raises the possibility of a neuroprotective approach to the treatment of glaucoma. (Guo L, et al. Targeting amyloid-β in glaucoma treatment. Proc Natl Acad Sci USA. 2007; 104 (33): 13444-13449.)

Retinitis pigmentosa (RP) is an inherited, degenerative eye disease that causes severe vision impairment due to the progressive degeneration of the rod photoreceptor cells in the retina. The progressive rod degeneration is later followed by abnormalities in the adjacent retinal pigment epithelium (RPE) and the deterioration of cone photoreceptor cells. Patients in the early stages of RP first notice compromised peripheral and dim light vision due to the decline of the rod photoreceptorsinherited, and finally blindness. It is estimated that 1.5 million people worldwide 1/4,000 are currently affected. There is no cure for retinitis pigmentosa.

C. Demyelinating Neurological Disorders

The group of demyelinating neurological disorders include adrenoleukodystrophy, multiple sclerosis (MS), optical neuritis, acute inflammatory demyelinating polyneuropathy (AIDP), chronic inflammatory demyelinating polyneuropathy (CIDP), Guillian-Barre syndrome (GBS), encephalitis caused by or related to Zika virus, neuromyelitis optica (NMO), acute disseminated encephalomyelitis, acute necrotizing hemorrhagic encephalitis, concentric sclerosis, diffuse sclerosis, metachromatic leukodystrophy, ball-like cell leukodystrophy, spongy degeneration of the central nervous system, Perry-plum disease, Alexander disease, radiation injury leukoencephalopathy, hypoxic leukoencephalopathy, periventricular leukomalacia disease, arteriosclerotic cortex under encephalopathy, progressive multifocal leukoencephalopathy, and central pontine myelinolysis syndrome.

C-1. Adrenoleukodystrophy

Adrenoleukodystrophy (also known as X-linked adrenoleukodystrophy, ALD, X-ALD, Siemerling-Creutzfeldt disease or bronze Schilder disease) is a disease linked to the X chromosome. It is a result of fatty acid buildup caused by the relevant enzymes not functioning properly, which then causes damage to the myelin sheathes of the nerves, resulting in seizures and hyperactivity. Other symptoms include problems with speaking, listening and understanding verbal instructions. ALD is the most common peroxisomal inborn error of metabolism, with an incidence estimated between 1:18,000 and 1:50,000.

Initial attempts at dietary therapy in ALD involved restricting the intake of very-long chain fatty acids (VLCFA), however it did not impact the levels of VLCFA in plasma and other body tissues. The parents of Lorenzo Odone, a boy with ALD, spearheaded efforts to develop a dietary treatment to slow the progression of the disease. They developed a mixture of unsaturated fatty acids (glycerol trioleate and glyceryl trierucate in a 4:1 ratio), known as Lorenzo's oil that inhibits elongation of saturated fatty acids in the body. Supplementation with Lorenzo's oil has been found to normalize the VLCFA concentrations in the body, although its effectiveness at treating the cerebral manifestations of the disease is still controversial and unproven. Trials with Lorenzo's oil have shown that it does not stop the neurological degradation in symptomatic patients, nor does it improve adrenal function.

C-2. Multiple Sclerosis

The total estimated number of people diagnosed with multiple sclerosis (MS) is approximately 1.3 million globally. MS is a debilitating, and disabling neurological disease characterized by multifocal destruction of myelin in central nervous system. Due to demyelination of myelin sheath of axons in white matter of central nervous system, myelin is damaged or destroyed, and the nerve impulses get slower or do not transmit at all, leading to disrupted communication between the brain and other parts of the body. Axonal damage occurs in every newly formed MS lesion, and cumulative axonal loss is the major cause of progressive and irreversible neurologic disability in MS. As many as 70% of axons are lost from the lateral corticospinal (e.g., motor) tracts in patients with advanced paraparesis from MS, and longitudinal MRI studies suggest there is progressive axonal loss over time within established, inactive lesions.

C-3. Other Demyelinated Diseases

Other demyelinated diseases include Acute inflammatory demyelinating polyneuropathy (AIDP), chronic inflammatory demyelinating polyneuropathy (CIDP), Guillian-Barre syndrome (GBS), encephalitis caused by or related to Zika virus, neuromyelitis optica (NMO), acute disseminated encephalomyelitis, acute necrotizing hemorrhagic encephalitis, concentric sclerosis, diffuse sclerosis, metachromatic leukodystrophy, ball-like cell leukodystrophy, spongy degeneration of the central nervous system, Perry-plum disease, Alexander disease, radiation injury leukoencephalopathy, hypoxic leukoencephalopathy, periventricular leukomalacia disease, arteriosclerotic cortex under encephalopathy, progressive multifocal leukoencephalopathy, and central pontine myelinolysis syndrome.

D. Neuromuscular Disorders and Muscular Dystrophy

Neuromuscular disease encompasses many diseases, disorders or conditions that impair the functioning of the muscles, either directly, or indirectly, being pathologies of nerves, muscle or neuromuscular junctions. Spinal muscular atrophies are disorders of lower motor neuron while amyotrophic lateral sclerosis is a mixed upper and lower motor neuron condition. Myasthenia gravis and Lambert-Eaton syndrome are examples of neuromuscular junction disorders. There is no cure for the treatment of these neuromuscular disorders. Current treatments are mostly symptomatic treatment and with modest efficacy.

Muscular dystrophy (MD) is a group of muscle diseases that results in increasing weakening and breakdown of skeletal muscles over time. The disorders differ in which muscles are primarily affected, the degree of weakness, how fast they worsen, and when symptoms begin. The most common type is Duchenne muscular dystrophy (DMD) which typically affects males beginning around the age of four. Other types include Becker muscular dystrophy, facioscapulohumeral muscular dystrophy, and myotonic dystrophy. Many people eventually become unable to walk. Some types are also associated with problems in other organs. Charcot-Marie-Tooth disease (CMT), named after the three doctors who first identified it, is one of the most common inherited nerve disorders. CMT affects an estimated 1 in 2,500 people in the United States and 2.6 million people worldwide, although experts believe the number could be much higher.

Currently, there is no cure for muscular dystrophy.

E. Brain Injury or Spinal Cord Nerve Injury, Cranial Nerve Disorders, or Seizures A brain injury is any injury occurring in the brain. Brain injuries can be classified along several dimensions. Primary and secondary brain injury are ways to classify the injury processes that occur in brain injury, while focal and diffuse brain injury are ways to classify the extent or location of injury in the brain. Brain injuries have far-reaching and varied consequences due to the nature of the brain as the main source of bodily control. Patients commonly experience issues with memory. This can be issues with either long or short-term memories depending on the location and severity of the injury. Memory can improve through rehabilitation but in some cases the damage can be permanent.

A spinal cord injury (SCI) is damage to the spinal cord that causes changes in its function, either temporary or permanent. These changes translate into loss of muscle function, sensation, or autonomic function in parts of the body served by the spinal cord below the level of the lesion.

Cranial nerve disease is an impaired functioning of any one of the twelve cranial nerves that emerge directly from the brain (including the brainstem), including the olfactory nerve (I), the optic nerve (II), oculomotor nerve (III), trochlear nerve (IV), trigeminal nerve (V), abducens nerve (VI), facial nerve (VII), vestibulocochlear nerve (VIII), glossopharyngeal nerve (IX), vagus nerve (X), accessory nerve (XI), and hypoglossal nerve (XII).

There is no cure for the treatment of these cranial nerve disorders. Current treatments are mostly symptomatic treatment and with modest efficacy.

Epilepsy is a group of neurological diseases characterized by epileptic seizures. About 1% of people worldwide (65 million) have epilepsy, and nearly 80% of cases occur in developing countries. In seizures, a group of neurons begin firing in an abnormal, excessive, and synchronized manner. This results in a wave of depolarization known as a paroxysmal depolarizing shift. Factors around the neuron include synaptic plasticity and ion concentrations are potential pathological mechanism. Current treatments are mostly symptomatic treatment.

F. Amyloid Deposit Related Diseases

Amyloid deposit related diseases are selected from the group consisting of diabetes, cardiac amyloidosis, primary amyloidosis, familial amyloidosis, senile systemic amyloidosis (SSA), secondary amyloidosis, and haemodialysis-associated amyloidosis.

Amyloidosis is a group of related diseases in which a protein called amyloid builds up in one or many organs—typically the kidney, heart, central nervous system (CNS), and/or liver—and interferes with organ function, eventually leading to organ failure. Primary amyloidosis (AL, amyloid light chain) is associated with a clonal plasma cell disease and the immunoglobulin light chains made by the abnormal plasma cells. AL also occurs in amyloidosis associated with multiple myeloma.

Familial amyloidosis (AF) is associated with a genetic abnormality that can be inherited. AF causes the liver to make an abnormal form of a protein called transthyretin.

Secondary amyloidosis (AA) is associated with inflammation and elevated levels of serum amyloid A caused by inflammation.

G. Other Chronic Diseases

Other chronic diseases or conditions in the present invention are selected from the group consisting of chronic kidney diseases, diabetes asthma and dyspnea.

Chronic kidney disease (CKD), also known as chronic renal disease, is progressive loss in kidney function over a period of months or years. At stage 5 CKD, renal replacement therapy is usually required, in the form of either dialysis or a transplant. Chronic kidney disease was the cause of 956,000 deaths globally in 2013. The kidney is one of the most frequent sites of amyloid deposition in amyloidosis related diseases. Renal disease is a frequent manifestation of the systemic amyloidosis and often is the major source of morbidity for individuals with these disorders. Without treatment, amyloidosis-associated kidney disease usually progresses to end-stage renal disease (ESRD). (Dember L M. J Am Soc Nephrol. 2006; 17(12):3458-71.)

Diabetes mellitus (DM), commonly referred to as diabetes, is a group of metabolic diseases in which there are high blood sugar levels over a prolonged period. The association of amylin with the development of type 2 diabetes has been known. Amyloid deposits deriving from islet amyloid polypeptide (IAPP, or amylin) are commonly found in pancreatic islets of patients suffering diabetes mellitus type 2, or containing an insulinoma cancer. Recent results suggest that amylin, like the related beta-amyloid (A$\beta$) associated with Alzheimer's disease, can induce apoptotic cell-death in insulin-producing beta cells, an effect that leads to the development of diabetes. (Lorenzo A, et al. Nature. 368 (6473): 756-60.)

Asthma is a common long term inflammatory disease of the airways of the lungs. It is characterized by variable and recurring symptoms, reversible airflow obstruction, and bronchospasm. Symptoms include episodes of wheezing, coughing, chest tightness, and shortness of breath. The patients may become worse at night or with exercise. There is no cure for asthma. Symptoms can be prevented by avoiding triggers, such as allergens and irritants, and inhaled corticosteroids.

H. Anti-Aging or Life-Span Prolongation

Maximum life span for humans, (or, maximum reported age at death or MRAD) is a measure of the maximum amount of time one or more members of a population have been observed to survive between birth and death. Currently there is no effective methods to prolong human life-span.

I. Brain Functions

Basic brain functions include vision, memory, learning, imaging, judgment, reading, perception, thinking and creating etc. Different people may have different levels of intellectual quotient (IQ). There is still a lot of undiscovered area about how brain works and the human brain functions are not fully developed. How to further develop the brain functions in human is an underdeveloped area in neuroscience.

SUMMARY OF THE INVENTION

It is an object of the present invention to provide a medicament for the treatment and the prophylaxis of neurological diseases in humans, but also in animals. These diseases include neurodegenerative diseases, optic or retinal degenerative diseases, demyelinating diseases, neuromuscular disorders and muscular dystrophy, brain or spinal cord nerve injury, cranial nerve disorders, or seizures, amyloid deposit related diseases, chronic diseases or conditions selected from the group consisting of kidney diseases, diabetes, asthma and dyspnea. It is further an object of the present invention to provide a functional food or nutrition supplement for humans and animals, e.g. for anti-aging, life-span prolongation or improving brain functions. Moreover, the present invention relates to the use of *Ophioglossum* and/or extracts thereof in the treatment and/or prevention of neurodegenerative diseases, optic or retinal degenerative diseases, demyelinating diseases, neuromuscular disorders and muscular dystrophy, brain or spinal cord nerve injury, amyloid related diseases, other chronic diseases or conditions selected from kidney diseases, diabetes, asthma and dyspnea, but also a functional food, e.g. for anti-aging, life-span prolongation and brain function improvement for human.

The present invention is based on the surprising findings that lipids bearing fatty acids with an odd number of carbon atoms and use of *Ophioglossum* and/or extracts thereof can be used for treating and/or prevention of diseases and disorders of the central nervous system.

DETAILED DESCRIPTION OF THE INVENTION

I. General Definitions

Figure 1:
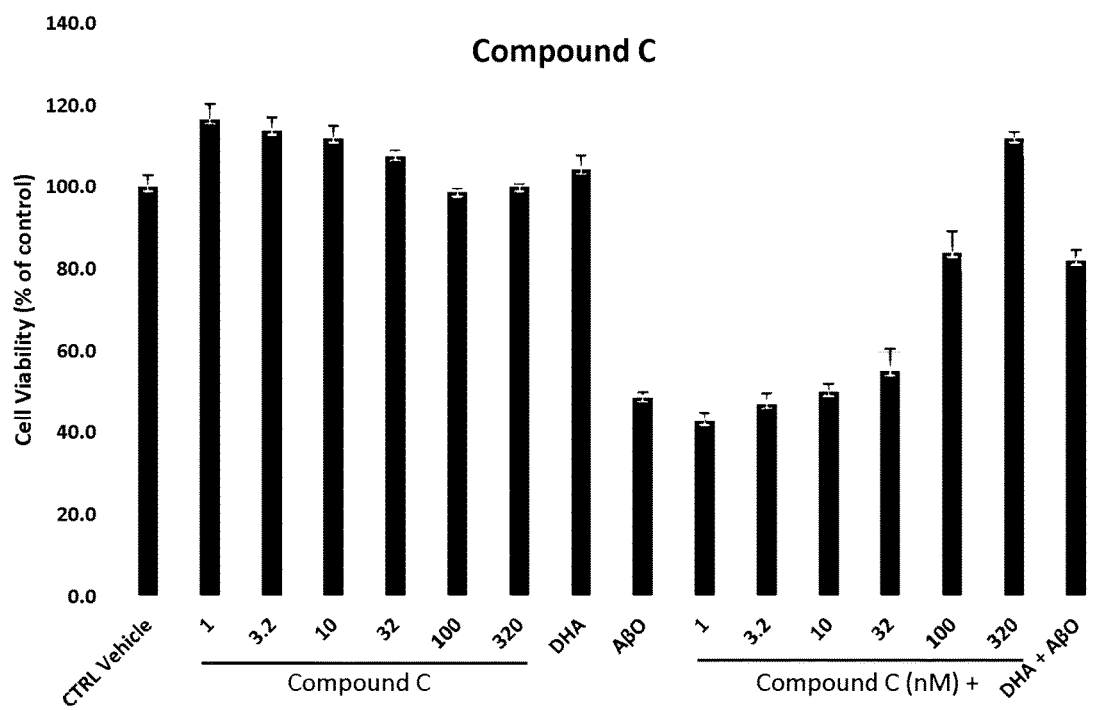
FIG. 1 relates to Example I-1 and shows neuroprotective effects of Compound C (added alone or 48 hours before A$\beta$O treatment) based on cell viability evaluated with MTT.

"Treat" or "treating" means any treatment, including, but not limited to, alleviating symptoms of a disease, disorder or condition, elimination the causation of a disease, disorder or condition on either on a temporary or permanent basis; or slowing, reducing, or inhibiting an ongoing pathological process in an asymptomatic individual.

"Preventing" and/or "prophylaxis" refers to inhibiting the initial onset of a pathologic process, such that that pathologic process that could eventually lead to development of symptoms never develops (i.e., preventing the development of a disease, disorder, or condition in a prophylactic manner).

"Therapeutically effective amount" means an amount of a compound that is effective in treating and/or preventing a particular disorder or condition.

"Pharmaceutically acceptable carrier" is a non-toxic solvent, dispersant, excipient, or other material used in formation of a pharmaceutical composition, i.e., a dosage form capable of administration to a subject or patient.

"Functional food" refers to a food given an additional function (often one related to health-promotion or disease prevention) by adding new ingredients or enriching existing ingredients. The term may also apply to traits purposely bred into existing edible plants, such as purple or gold potatoes having enriched anthocyanin or carotenoid contents, respectively. Functional foods may be "designed to have physiological benefits and/or reduce the risk of chronic disease beyond basic nutritional functions, and may be similar in appearance to conventional food and consumed as part of a regular diet" (US Department of Agriculture, Agricultural Research Service, AgResearch Magazine. November 2014; US Department of Agriculture, Agricultural Research Service. July 2010)

The term "pharmaceutically acceptable salt" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

As used herein, "rescue" means returning or rejuvenating the current pathological structure, state, condition or function of human body to a previous younger or better structure, state, condition or function status.

As used herein, "regenerating" means regrowing new tissues to replace lost or injured tissues or function of human body.

(1) In a first embodiment, the present invention relates to a compound of the formula (I)

wherein $R^2$ and $R^3$ are independently selected from H or —C(O)$R^4$, wherein $R^4$ is
- ($C_5$-$C_{20}$)alkyl, which is optionally mono-, di- or trisubstituted with OH, $NH_2$, $NHCH_3$, $N(CH_3)_2$, F or Cl; or
- ($C_5$-$C_{20}$)alkenyl, bearing 1, 2 or 3 double bonds;

whereby at least one of $R^1$, $R^2$ and $R^3$ is —C(O)$R^4$ with $R^4$ being ($C_6$-$C_{20}$) alkyl with an even number of carbon atoms; or a pharmaceutically acceptable salt thereof, for the use as a medicament for human and/or animals.

(2) In a further embodiment, the present invention relates to embodiment (1), wherein $R^2$ and $R^3$ are independently selected from H or —C(O)$R^4$, wherein $R^4$ is
- ($C_5$-$C_{20}$)alkyl, which is optionally mono-, di- or trisubstituted with OH, F or Cl; or
- ($C_5$-$C_{20}$)alkenyl, bearing 1, 2 or 3 double bonds;

whereby at least one of $R^1$, $R^2$ and $R^3$ is —C(O)$R^4$ with $R^4$ being ($C_6$-$C_{20}$) alkyl with an even number of carbon atoms.

(3) In a further embodiment, the present invention relates to embodiment (1) or (2), wherein $R^2$ and $R^3$ are independently selected from H or —C(O)$R^4$, wherein $R^4$ is
- ($C_5$-$C_{20}$)alkyl, which is optionally mono-, di- or trisubstituted with OH, F or Cl;

whereby at least one of $R^1$, $R^2$ and $R^3$ is —C(O)$R^4$ with $R^4$ being ($C_6$-$C_{20}$) alkyl with an even number of carbon atoms.

(4) In a further embodiment, the present invention relates to any one of embodiments (1) to (3), wherein $R^1$, $R^2$ and $R^3$ are independently selected from H or —C(O)$R^4$, wherein $R^4$ is
- ($C_5$-$C_{20}$)alkyl, which is optionally mono-, di- or trisubstituted with OH or F; or
- ($C_5$-$C_{20}$)alkenyl, bearing 1, 2 or 3 double bonds;

whereby at least one of $R^1$, $R^2$ and $R^3$ is —C(O)$R^4$ with $R^4$ being ($C_6$-$C_{20}$) alkyl with an even number of carbon atoms.

(5) In a further embodiment, the present invention relates to any one of embodiments (1) to (4), wherein $R^1$, $R^2$ and $R^3$ are independently selected from H or —C(O)$R^4$, wherein $R^4$ is
- ($C_5$-$C_{20}$)alkyl, which is optionally mono-, di- or trisubstituted with OH or F; or whereby at least one of $R^1$, $R^2$ and $R^3$ is —C(O)$R^4$ with $R^4$ being ($C_6$-$C_{20}$) alkyl with an even number of carbon atoms.

(6) In a further embodiment, the present invention relates to any one of embodiments (1) to (5), wherein $R^1$, $R^2$ and $R^3$ are independently selected from H or —C(O)$R^4$, wherein $R^4$ is
- ($C_5$-$C_{20}$)alkyl, which is optionally mono-, di- or trisubstituted with F; or
- ($C_5$-$C_{20}$)alkenyl, bearing 1, 2 or 3 double bonds;

whereby at least one of $R^1$, $R^2$ and $R^3$ is —C(O)$R^4$ with $R^4$ being ($C_6$-$C_{20}$) alkyl with an even number of carbon atoms.

(7) In a further embodiment, the present invention relates to any one of embodiments (1) to (6), wherein $R^1$, $R^2$ and $R^3$ are independently selected from H or —C(O)$R^4$, wherein $R^4$ is ($C_5$-$C_{20}$)alkyl, which is optionally mono-, di- or trisubstituted with F;

whereby at least one of $R^1$, $R^2$ and $R^3$ is —C(O)$R^4$ with $R^4$ being ($C_6$-$C_{20}$) alkyl with an even number of carbon atoms.

(8) In a further embodiment, the present invention relates to any one of embodiments (1) to (7), wherein $R^2$ and $R^3$ are independently selected from H or —C(O)$R^4$ and wherein at least one of $R^1$, $R^2$ and $R^3$ is —C(O)$R^4$ with $R^4$ being ($C_6$-$C_{20}$) alkyl with an even number of carbon atoms.

(9) In a further embodiment, the present invention relates to any one of embodiments (1) to (8), wherein $R^1$, $R^2$ and $R^3$ are independently selected from —C(O)$R^4$ with $R^4$ being ($C_6$-$C_{20}$) alkyl with an even number of carbon atoms.

(10) In a further embodiment, the present invention relates to any one of embodiments (1) to (9), wherein $R^4$ is H or —C(O)$R^4$ with $R^4$ being $C_{12}$-alkyl, $C_{14}$-alkyl, $C_{16}$-alkyl, $C_{18}$-alkyl, or $C_{20}$-alkyl, whereby not all $R^1$, $R^2$ and $R^3$ are H at the same time.

(11) In one embodiment of (10), one of $R^1$, $R^2$ and $R^3$ is H and the others are —C(O)$R^4$ with $R^4$ being $C_{12}$-alkyl, $C_{14}$-alkyl, $C_{16}$-alkyl, $C_{18}$-alkyl or $C_{20}$-alkyl.

(12) In one embodiment of (10), two of $R^1$, $R^2$ and $R^3$ are H and the other is —C(O)$R^4$ with $R^4$ being $C_{12}$-alkyl, $C_{14}$-alkyl, $C_{16}$-alkyl, $C_{18}$-alkyl or $C_{20}$-alkyl.

(13) In one embodiment of (10), $R^1$, $R^2$ and $R^3$ are independently from each other —C(O)$R^4$ with $R^4$ being $C_{12}$-alkyl, $C_{14}$-alkyl, $C_{16}$-alkyl, $C_{18}$-alkyl or $C_{20}$-alkyl. It is to be understood, that each of the alkyls of $R^4$ can be combined with each other of the alkyls. In particular, all $R^1$, $R^2$ and $R^3$ can be the same kind of —C(O)$R^4$. Preferably, $R^1$, $R^2$ and $R^3$ are either independently from each other or all together —C(O)$R^4$ with $R^4$ being $C_{14}$-alkyl or $C_{16}$-alkyl.

(14) In a particularly preferred embodiment, the present invention relates to a compound of formula (I), wherein $R^4$ is —C(O)$C_{14}$-alkyl, i.e. a compound of formula (I) wherein $R^1$, $R^2$ and $R^3$ are all —C(O)$C_{14}$-alkyl. The compound of this embodiment is the same as Compound C described below. The chemical name of Compound C is tripentadecanoin, also known as 1,2,3-Propanetriyl tripentadecanoate, 1,2,3-propanetriyl tripentadecanoate, or 1,2,3-tripentadecanoylglycerol.

(15) In another embodiment, the present invention relates to a compound of formula (I), wherein one of $R^1$, $R^2$ and $R^3$ is H and the others are —C(O)$C_{14}$-alkyl.

(16) In another embodiment, the present invention relates to a compound of formula (I), wherein two of $R^1$, $R^2$ and $R^3$ is H and the third one is —C(O)$C_{14}$-alkyl.

(17) In a further embodiment, the invention relates to metabolites or prodrugs of the compound according to embodiments (10) to (16), namely to the carboxylic acids HOC(O)$C_{12}$-alkyl, HO C(O)$C_{14}$-alkyl, HOC(O)$C_{16}$-alkyl, HOC(O)$C_{18}$-alkyl and HOC(O)$C_{20}$-alkyl. In particular, the invention relates to metabolites or prodrugs of the compound according to embodiment (14), namely to HOC(O)$C_{14}$-alkyl.

(18) It is to be understood that all embodiments (1) to (17) relate to the described compounds or a pharmaceutically acceptable salt thereof, for the use as a medicament for human and/or animals.

(19) A further embodiment of the invention relates to any one of the compounds described in embodiments (1) to (17), for the use in the treatment and/or prevention of neurodegenerative diseases, retinal or optic nerve degenerative diseases, demyelinating diseases, neuromuscular disorders and muscular dystrophy, brain or spinal cord nerve injury, cranial nerve disorders, or seizures, amyloid deposit related diseases, chronic diseases or conditions selected from the group consisting of kidney diseases, diabetes, asthma and dyspnea; and for the use of anti-aging or life-span prolongation and improving brain function.

(20) A further embodiment of the invention relates to any one of the compounds described in embodiments (1) to (17), for the use in the treatment and/or prevention of neurodegenerative diseases which are selected from the group consisting of Alzheimer's disease (AD), Parkinson's disease (PD), Huntington's disease (HD), Amyotrophic lateral sclerosis (ALS), dementia, Dementia with Lewy bodies (DLB), frontotemporal dementia (FTD), Creutzfeldt-Jakob disease, and brain atrophy.

(21) A further embodiment of the invention relates to any one of the compounds described in embodiments (1) to (17), for the use in the treatment and/or prevention of optic and retinal degenerative diseases which are selected from the group consisting of optical atrophy, Leber's hereditary optic neuropathy (LHON), Dominant Optic Atrophy (DOA), age-related macular degeneration, glaucoma and retinitis pigmentosa.

(22) A further embodiment of the invention relates to any one of the compounds described in embodiments (1) to (17), for the use in the treatment and/or prevention of demyelinating diseases which are selected from the group consisting of adrenoleukodystrophy, multiple sclerosis, optical neuritis, Acute Inflammatory Demyelinating Polyneuropathy (AIDP), Chronic Inflammatory Demyelinating Polyneuropathy (CIDP), Guillian-Barre syndrome, encephalitis caused by or related to Zika virus, cranial nerve palsy, neuromyelitis optica (NMO), acute disseminated encephalomyelitis, acute necrotizing hemorrhagic encephalitis, concentric sclerosis, diffuse sclerosis, metachromatic leukodystrophy, ball-like cell leukodystrophy, spongy degeneration of the central nervous system, Perry-plum disease, Alexander disease, radiation injury leukoencephalopathy, hypoxic leukoencephalopathy, periventricular leukomalacia disease, arteriosclerotic cortex under encephalopathy, progressive multifocal leukoencephalopathy, and central pontine myelinolysis syndrome. In particular, for the use in the treatment and/or prevention of multiple sclerosis, optical neuritis, Acute Inflammatory Demyelinating Polyneuropathy (AIDP), Chronic Inflammatory Demyelinating Polyneuropathy (CIDP), Guillian-Barre syndrome, encephalitis caused by or related to Zika virus, cranial nerve palsy, and neuromyelitis optica (NMO).

(23) A further embodiment of the invention relates to any one of the compounds described in embodiments (1) to (17), for the use in the treatment and/or prevention of neuromuscular disorders and muscular dsytrophy diseases which are selected from the group consisting of myasthenia gravis, Lambert-Eaton syndrome, Duchenne muscular dystrophy, Becker muscular dystrophy, facioscapulohumeral muscular dystrophy, myotonic dystrophy, Charcot-Marie-Tooth disease (CMT).

(24) A further embodiment of the invention relates to any one of the compounds described in embodiments (1) to (17), for the use in the treatment and/or prevention of neurological injury related diseases or mixed neurological diseases selected from the group consisting of acute or chronic brain injury or spinal cord or nerve injury, cranial nerve disorders and seizures.

(25) A further embodiment of the invention relates to any one of the compounds described in embodiments (1) to (17), for the use in the treatment and/or prevention of amyloid deposit related diseases which are selected from the group consisting of diabetes, cardiac amyloidosis, primary amyloidosis, familial amyloidosis, senile systemic amyloidosis (SSA), secondary amyloidosis, and haemodialysis-associated amyloidosis.

(26) A further embodiment of the invention relates to any one of the compounds described in embodiments (1) to (17), for the use in the treatment and/or prevention of chronic diseases or conditions selected from the group consisting of kidney diseases, diabetes, asthma and dyspnea.

(27) A further embodiment of the invention relates to any one of the compounds described in embodiments (1) to (17), for the use in the treatment and/or prevention of diseases or disorders of the central nervous system.

(28) A further embodiment of the invention relates to any one of the compounds described in embodiments (8) to (17), for the use in the treatment and/or prevention of the diseases and conditions of embodiments (19) to (27).

A particularly preferred embodiment of the invention relates to any one of the compounds described in embodiment (14), for the use in the treatment and/or prevention of the diseases and conditions of embodiments (19) to (27).

(29) A further embodiment of the invention relates to the compound according to any one of embodiments (1) to (17) for the use in the treatment and/or prevention of the diseases and conditions of embodiments (19) to (27), wherein the treatment dosage is from 1 mg/day to 1000 mg/day. In a further embodiment, the treatment dosage is from 1 mg/day to 1000 mg/day. The lower limits are for instance 1 mg/day, 5 mg/day, 10 mg/day, 20 mg/day, 25 mg/day or 50 mg/day. The upper limits are for instance 1000 mg/day, 900 mg/day, 800 mg/day, 750 mg/day, 700 mg/day, 600 mg/day, 500 mg/day, 250 mg/day, 200 mg/day. It is to be understood that each upper limit can be combined with each lower limit. In a preferred embodiment, the dosage is from 10 mg/day to 200 mg/day.

In one embodiment, the given doses apply in particular to the compound according to any one of embodiments (8) to (17), particularly to embodiment (14).

(30) A further embodiment of the invention relates to a pharmaceutical composition as such and in particular for the use in the treatment and/or prevention of the diseases and conditions of any one of embodiments (19) to (27), wherein the composition contains the compound of any one of embodiments (1) to (17) and a pharmaceutically acceptable carrier. Preferably, the composition contains the compound of any one of embodiments (8) to (17), in particular embodiment (14).

(31) In a further embodiment, the pharmaceutical composition according to embodiment (30) contains the compound of any one of embodiments (1) to (17) in an amount of 1 mg/day to 1000 mg/day. The lower limits are for instance 1 mg/day, 5 mg/day, 10 mg/day, 20 mg/day, 25 mg/day or 50 mg/day. The upper limits are for instance 1000 mg/day, 900 mg/day, 800 mg/day, 750 mg/day, 700 mg/day, 600 mg/day, 500 mg/day, 250 mg/day, 200 mg/day. It is to be understood that each upper limit can be combined with each lower limit. In a preferred embodiment, the dosage is from 10 mg/day to 200 mg/day.

In one embodiment, the given doses apply in particular to the compound according to any one of embodiments (8) to (17), particularly to embodiment (14).

(32) In one embodiment, the pharmaceutical composition of embodiment (30) relates to formulations containing the active ingredient preferably in an amount as indicated embodiment (29) or (31), and can be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

In one embodiment, the formulations apply in particular to the compound according to any one of embodiments (8) to (17), particularly to embodiment (14).

(33) A further embodiment of the invention relates to the use of the compound according to any one of embodiments (1) to (17) for the manufacture of a medicament for the treatment and/or prevention of the diseases and conditions of any one of embodiments (19) to (27). It is to be understood that all embodiments relating to the compounds of embodiments (1) to (17) for the use as medicament as such or for the treatment and/or prevention of the diseases given in embodiments (19) to (27) are disclosed and may be reformulated as use of the compound(s) for the manufacture of a medicament for the treatment and/or prevention of the disclosed diseases and conditions.

Preferably, the compound according to any one of embodiments (1) to (17), particularly of embodiments (8) to (17), preferably of embodiment (14) is comprised in the medicament in the amount as described in embodiments (29) and (31). Moreover, the medicament may be formulated as described in embodiment (32).

(34) A further embodiment of the invention relates to a method for treating and/or preventing the diseases and conditions of any one of embodiments (19) to (27), comprising administering to a patient an effective amount of the compound according to any one of embodiments (1) to (17). Thereby, the "effective amount" is as described above. In particular, the effective amount is as described in embodiments (29) and (31). It is to be understood that all embodiments relating to the compounds of embodiments (1) to (17) for the use as medicament as such or for the treatment and/or prevention of the diseases given in embodiments (19) to (27) are disclosed and may be reformulated in the respective method for treating and/or prevention format. The doses are the same as disclosed for example in embodiment (29) or (31). Moreover, the treatment and/or prevention can be performed with a medicament formulated as described in embodiment (32).

Preferably, the compound according to any one of embodiments (1) to (17), particularly of embodiments (8) to (17), preferably of embodiment (14) is comprised in the amount as described in embodiments (29) and (31). Moreover, the compound may be formulated as described in embodiment (32).

(35) A further embodiment of the invention relates to the use of the compound according to any one of embodiments (1) to (17) as functional food or food supplement for human and/or animals. A functional food or food supplement in this sense is a food or food supplement that has physiological benefits and/or reduces the risk of the diseases and disorders of embodiments (18) to (27). A functional food or food supplement can be consumed as a part of a regular diet.

(36) A further embodiment of the invention relates to the use of any one of the compounds described in embodiments (1) to (17), for humans and animals for anti-aging, life-span prolongation or improving brain functions.

(37) A further embodiment of the invention relates to the use according to embodiment (35), wherein the functional food or the food supplement is for humans and animals for anti-aging, life-span prolongation or improving brain functions.

(38) A further embodiment of the invention relates to the use of the compound according to any one of embodiments (1) to (17) as functional food or food supplement for human and/or animals, wherein the functional food or food supplement is for improving brain functions including vision, memory, learning, imaging, judgement, reading, perception, thinking, creating, elevating intellectual quotient (IQ).

(39) A further embodiment of the invention relates to the use of the compound according to any one of embodiments (1) to (17) as functional food or food supplement for human and/or animals, wherein the functional food is for neurodegenerative diseases, retinal or optic nerve degenerative diseases, demyelinated diseases, neuromuscular disorders and muscular dystrophy, brain or spinal cord nerve injury, amyloid deposit related diseases, and chronic diseases or conditions selected from the group consisting of kidney diseases, diabetes, asthma and dyspnea.

(40) A further embodiment of the invention relates to the use of the compound according to any one of embodiments (1) to (17) as functional food or food supplement for human and/or animals for specific diseases and conditions, wherein the diseases and conditions are those recited in embodiments (19) to (27).

(41) A further embodiment of the invention relates to any one of the compounds described in embodiments (8) to (17), as functional food or food supplement for human and/or animal according to embodiments (35) to (40).

A particularly preferred embodiment of the invention relates to the compound described in embodiment (14), as functional food or food supplement for human and/or animal according to embodiments (35) to (40).

In one embodiment, the compound relates to any one of the compounds described in embodiments (8) to (17), particularly to embodiment (14).

(42) A further embodiment of the invention relates to the use of the compound according to any one of embodiments (1) to (17) as functional food or food supplement for human and/or animals, wherein the dosage is from 1 (microgram)/day to 50 mg/day. In a further embodiment, the dosage is from 1 (microgram)/day to 20 mg/day. The lower limits are for instance 1 (microgram)/day, 2 µg (microgram)/day, 3 µg (microgram)/day, 4 µg (microgram)/day, 5 µg (microgram)/day, 7 µg (microgram)/day, 10 µg (microgram)/day, 20 µg (microgram)/day, 25 µg (microgram)/day, 50 µg (microgram)/day, 100 µg (microgram)/day, 200 µg (microgram)/day, 300 µg (microgram)/day, 400 µg (microgram)/day or 500 µg (microgram)/day. The upper limits are for instance 50 mg/day, 40 mg/day, 30 mg/day, 20 mg/day, 10 mg/day, 5 mg/day, 3 mg/day, 2 mg/day, 1 mg/day, 900 µg (microgram)/day. It is to be understood that each upper limit can be combined with each lower limit. In one embodiment, the dosage is from 1 (microgram)/day to 20 mg/day. In another embodiment, the dosage is from 1 (microgram)/day to 900 µg (microgram)/day.

In one embodiment, the given doses apply in particular to the compound according to any one of embodiments (8) to (17), particularly to embodiment (14).

(43) A further embodiment of the invention relates to the preparation of a compound of formula (I) according to any one of embodiments (1) to (17) by esterification of glycerol with a fatty acid of the formula (II) HOC(O)R$^4$, wherein R$^4$ is independently from each other
- ($C_5$-$C_{20}$) alkyl, which is optionally mono-, di- or trisubstituted with OH, $NH_2$, $NHCH_3$, $N(CH_3)_2$, F or Cl; or
- ($C_5$-$C_{20}$) alkenyl, bearing 1, 2 or 3 double bonds;
whereby at least one of HOC(O)R$^4$ bears an R$^4$ being ($C_6$-$C_{20}$) alkyl with an even number of carbon atoms.

Esterification of glycerol is known to the skilled person. For example, esterification can be acid-catalysed, for instance with methanolic HCl, methanolic $H_2SO_4$, borontrifluoride as an example of a Lewis acid and other acidic catalysts. Moreover, esters can be obtained via activated fatty acids, such as acid halides, fatty acid anhydrides, imidazolides and with other well-known coupling reagents like DCC (N,N'-Dicyclohexylcarbodiimid) or EDC (1-Ethyl-3-(3-dimethylaminopropyl)carbodiimide).

Moreover, protecting group strategies can be used in order to specifically esterify a desired position with a desired fatty acid. Appropriate protecting groups can form 5- or 6-membered 1,2-diols, such as the reaction of glycerol with benzaldehyde, leading to a 1,3-benzylidene derivative, or the formation of a 1,2-acetonide with acetone. 1,2-Diols may also be protected as their cyclic carbonates, which can be prepared with phosgene ($COCl_2$), or triphosgene ($CCl_3OC(O)OCCl_3$). Protecting group strategies are known to the skilled person, for instance from "Protective Groups in Organic Synthesis", T. W. Greene, P. G. M. Wuts, Wiley-Interscience, 1999.

(44) A further embodiment of the invention relates to the preparation of the compound according to embodiment (14) by esterification of glycerol with pentadecanoic acid.

(45) In a further embodiment of the invention, the compound of embodiment (14) can be obtained from herbs or from human/animal milk.

(46) It may be stated that the compound of embodiment (14) is contained in the plant genus *Ophioglossum*.

(47) In the present invention, it is to be understood that *Ophioglossum* comprises all species of *Ophioglossum*. In particular, it consists of the group selected from *Ophioglossum* sp., *Ophioglossum* L., *Ophioglossum thermale* Kom., *Ophioglossum thermale* Komarov, *Ophioglossum austroasiaticum* Nishida, *Ophioglossum austroasiaticum* Nish., *Ophioglossum petiolatum* L., *Ophioglossum pendulum* L., *Ophioderma pendula* (L.) Presl., *Ophioglossum reticulatum* L., *Ophioglossum vulgatum* L., *Ophioglossum pedunculosum* Desv., *Ophioglossum parvifolium* Grey. et HK., *Ophioglossum petiolatum* Hook., *Ophioglossum petiolatum* Hooker, *Ophioglossum tenerum*, *Ophioglossum pycnostichum*, *Ophioglossum pycnostichum* (Fern.) A.&D. Love, *Ophioglossum pycnostichum* (Fernald) A. Löve & D. Löve; *O. vulgatum* var. *pycnostichum* Fernald, *Ophioglossum crotalophoroides* Walt., *Ophioglossum crotalophoroides* Walter var. *crotalophoroides*, *Ophioglossum crotalophoroides* Walter var. *nanum* Osten ex J. S. Licht., *Ophioglossum azoricum*, *Ophioglossum azoricum* C. Presl, *Ophioglossum vulgatum Linnaeus* var. *pseudopodum* (S. F. Blake) Farwell, *Ophioglossum dendroneuron* E.P. St.John; *O. ellipticum* Hooker & Greville; *O. mononeuron* E.P. St.John, *Ophioglossum dendroneuron* E.P. St. John, *Ophioglossum Linnaeus*, *Ophioglossum palmatum* L., *Ophioglossum mononeuron* E.P. St. John, *Ophioglossum austroasiaticum*, *Ophioglossum bergianum*, *Ophioglossum bucharicum*, *Ophioglossum californicum*, *Ophioglossum caroticaule*, *Ophioglossum convexum*, *Ophioglossum californicum* Prantl, *Ophioglossum concinnum*, *Ophioglossum concinnum* Brack., *Ophioglossum costatum*, *Ophioglossum costatum* R.Br., *Ophioglossum coriaceum*, *Ophioglossum decipi-* ens, *Ophioglossum dietrichiae, Ophioglossum dudadae, Ophioglossum engelmannii, Ophioglossum engelmannii* Prantl, *Ophioglossum ellipticum* Hook. & Grey., *Ophioglossum fernandezianum, Ophioglossum gomezianum, Ophioglossum gracile, Ophioglossum gramineum* Willd., *Ophioglossum gramineum, Ophioglossum harrisii, Ophioglossum intermedium, Ophioglossum kawamurae, Ophioglossum lancifolium, Ophioglossum latifolium, Ophioglossum litorale, Ophioglossum loureirianum, Ophioglossum lusitanicum* L., *Ophioglossum lusitanicum* L. ssp. *californicum* (Prantl) R.T. Clausen, *Ophioglossum lusitanicum* L. var. *californicum* (Prantl) Broun, *Ophioglossum moultoni, Ophioglossum namegatae, Ophioglossum nudicaule, Ophioglossum nudicaule* L. f., *Ophioglossum nudicaule* L. f. var. minus R.T. Clausen, *Ophioglossum nudicaule* L. f. var. *tenerum* (Mett. ex Prantl) R.T. Clausen, *Ophioglossum oblongum, Ophioglossum obovatum, Ophioglossum opacum, Ophioglossum ovatum, Ophioglossum parvifolium, Ophioglossum parvum, Ophioglossum pendulum, Ophioglossum pendulum* L. ssp. *falcatum* (C. Presl) R.T. Clausen, *Ophioglossum pendulum* L. ssp. *Pendulum, Ophioglossum petiolatum, Ophioglossum polyphyllum, Ophioglossum polyphyllum* A. Braun, *Ophioglossum polyphyllum* A. Braun ex Schub., *Ophioglossum pumilio, Ophioglossum pusillum, Ophioglossum pusillum* Raf., *Ophioglossum raciborskii, Ophioglossum ramosii, Ophioglossum reticulatum, Ophioglossum rubellum, Ophioglossum savatieri, Ophioglossum scariosum, Ophioglossum schmidii, Ophioglossum simplex, Ophioglossum thermal, Ophioglossum thomasii, Ophioglossum timorense, Ophioglossum tenerum* Mett. ex Prantl, *Ophioglossum usterianum, Ophioglossum vulgatum, Ophioglossum vulgatum* auct. non L., *Ophioglossum vulgatum* L. var. *alaskanum* (E.G. Britton) C. Chr., *Ophioglossum vulgatum* L. var. *pseudopodum* (S.F. Blake) Farw., *Ophioglossum vulgatum* L. var. *pycnostichum* Fernald, Ophioglossaceae Martinov, *Cheiroglossa palmata* (L.) C. Presl, *Ophioglossum eliminatum* Khand. & Goswami, *Ophioglossum namegatae* Nish. & Kurita, *Ophioglossum nipponicum* Miyabe & Kudo, and/or *Ophioglossum oleosum* Khand.

Preferred *Ophioglossum* are *Ophioglossum thermale, Ophioglossum petiolatum, Ophioglossum reticulatum, Ophioglossum parvifolium, Ophioglossum vulgatum, Ophioglossum austroasiaticum, Ophioglossum azoricum, Ophioglossum californicum, Ophioglossum costatum, Ophioglossum crotalophoroides, Ophioglossum engelmanii, Ophioglossum lusitanicum, Ophioglossum nudicaule, Ophioglossum polyphyllum, Ophioglossum pusillum*, and/or *Ophioglossum pycnosticum*.

Particularly preferred *Ophioglossum* are *Ophioglossum thermale, Ophioglossum* petiolatum, *Ophioglossum* reticulatum, *Ophioglossum vulgatum*, and/or *Ophioglossum austro-asiaticum* Nishida.

In the present invention, herb B is *Ophioglossum*.

(48) Hence, an embodiment of the present invention relates to *Ophioglossum* for the treatment and/or prevention of the diseases described in embodiments (19) to (27), i.e. the use of *Ophioglossum* for the treatment and/or prevention of the diseases and conditions of any one of embodiments (19) to (27).

(49) One embodiment of the invention relates to the use of *Ophioglossum* in an amount that contains 1 mg/day to 1000 mg/day of the compound of embodiment (14), i.e. tripentadecanoin or Compound C.

A further embodiment relates to the use of *Ophioglossum* in an amount that contains the compound of embodiment (14), i.e. tripentadecanoin or Compound C, from 1 mg/day to 1000 mg/day. The lower limits are for instance 1 mg/day, 5 mg/day, 10 mg/day, 20 mg/day, 25 mg/day or 50 mg/day of compound C contained in *Ophioglossum*. The upper limits are for instance 1000 mg/day, 900 mg/day, 800 mg/day, 750 mg/day, 700 mg/day, 600 mg/day, 500 mg/day, 250 mg/day, 200 mg/day of compound C contained in ophiglossum. It is to be understood that each upper limit can be combined with each lower limit. In a preferred embodiment, the dosage is from 10 mg/day to 200 mg/day.

Alternatively, the invention relates to the use of *Ophioglossum* in an amount of 10 mg to 10000 mg/day of dry *Ophioglossum* powder. The lower limits are for instance 10 mg/day, 20 mg/day, 30 mg/day, 40 mg/day, 50 mg/day, 100 mg/day, 150 mg/day, 200 mg/day, 300 mg/day, 500 mg/day, 700 mg/day. The upper limits are for instance 10000 mg/day, 8000 mg/day, 6000 mg/day, 5000 mg/day, 2500 mg/day, 1000 mg/day. It is to be understood that each upper limit can be combined with each lower limit.

(50) A further embodiment of the invention relates to a pharmaceutical composition for the use in the treatment and/or prevention of the diseases and conditions of any one of embodiments (19) to (27), wherein the composition contains *Ophioglossum*.

(51) A further embodiment of the invention relates to a pharmaceutical composition for the use in the treatment and/or prevention of the diseases and conditions of any one of embodiments (19) to (27), wherein the composition contains *Ophioglossum* in an amount that contains 1 mg/day to 1000 mg/day of the compound of embodiment (14), i.e. tripentadecanoin or Compound C.

A further embodiment of the invention relates to said pharmaceutical composition wherein the compound of embodiment (14), i.e. tripentadecanoin or Compound C is contained from 1 mg/day to 1000 mg/day. The lower limits are for instance 1 mg/day, 5 mg/day, 10 mg/day, 20 mg/day, 25 mg/day or 50 mg/day of compound C contained in *Ophioglossum*. The upper limits are for instance 1000 mg/day, 900 mg/day, 800 mg/day, 750 mg/day, 700 mg/day, 600 mg/day, 500 mg/day, 250 mg/day, 200 mg/day of compound C contained in ophiglossum. It is to be understood that each upper limit can be combined with each lower limit. In a preferred embodiment, the dosage is from 10 mg/day to 200 mg/day.

Alternatively, the invention relates to a pharmaceutical composition for human and/or animals, wherein *Ophioglossum* is contained as 10 mg to 10000 mg/day of dry *Ophioglossum* powder. The lower limits are for instance 10 mg/day, 20 mg/day, 30 mg/day, 40 mg/day, 50 mg/day, 100 mg/day, 150 mg/day, 200 mg/day, 300 mg/day, 500 mg/day, 700 mg/day. The upper limits are for instance 10000 mg/day, 8000 mg/day, 6000 mg/day, 5000 mg/day, 2500 mg/day, 1000 mg/day. It is to be understood that each upper limit can be combined with each lower limit.

(52) A further embodiment of the invention relates to a formulation containing *Ophioglossum* preferably in an amount as indicated embodiment (49) or (51), and can be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

(53) A further embodiment of the invention relates to the use of *Ophioglossum* for the manufacture of a medicament for the treatment and/or prevention of the diseases and conditions of any one of embodiments (19) to (27). It is to be understood that all embodiments relating to *Ophioglossum* for the treatment and/or prevention of the diseases given in embodiments (19) to (27) are disclosed and may be reformulated as use of *Ophioglossum* for the manufacture of a medicament for the treatment and/or prevention of the disclosed diseases and conditions.

Preferably, *Ophioglossum* contains the compound of embodiment (14), i.e. tripentadecanoin or Compound C in the amount as described in embodiments (49) and (51).

Moreover, the medicament may be formulated as described in embodiment (52).

(54) A further embodiment of the invention relates to a method for treating and/or preventing the diseases and conditions of any one of embodiments (19) to (27), comprising administering to a patient an effective amount of *Ophioglossum*. Thereby, the "effective amount" is as described above. In particular, the effective amount is as described in embodiments (49) and (51). It is to be understood that all embodiments relating to *Ophioglossum* for the treatment and/or prevention of the diseases given in embodiments (19) to (27) are disclosed and may be reformulated in the respective method for treating and/or prevention format. The doses are the same as disclosed for example in embodiment (49) or (51). Moreover, the treatment and/or prevention can be performed with a medicament formulated as described in embodiment (52).

Preferably, *Ophioglossum* contains the compound of embodiment (14), i.e. tripentadecanoin or Compound C in the amount as described in embodiments (49) and (51). Moreover, the medicament may be formulated as described in embodiment (52).

(55) Moreover, a further embodiment of the invention relates the use of *Ophioglossum* as functional food or food supplement for human and/or animal.

(56) A further embodiment of the invention relates to the use of *Ophioglossum* for humans and animals for anti-aging, life-span prolongation or improving brain functions.

(57) A further embodiment of the invention relates to the use according to embodiment (55), wherein the functional food or the food supplement is for humans and animals for anti-aging, life-span prolongation or improving brain functions.

(58) A further embodiment of the invention relates to the use of *Ophioglossum* as functional food or food supplement for human and/or animals, wherein the functional food or food supplement is for improving brain functions including vision, memory, learning, imaging, judgement, reading, perception, thinking, creating, elevating intellectual quotient (IQ).

(59) A further embodiment of the invention relates to the use of *Ophioglossum* as functional food or food supplement for human and/or animals, wherein the functional food is for neurodegenerative diseases, retinal or optic nerve degenerative diseases, demyelinated diseases, neuromuscular diseases and muscular dystrophy, brain or spinal cord nerve injury, amyloid deposit related diseases, and chronic diseases or conditions selected from the group consisting of kidney diseases, diabetes, asthma and dyspnea.

(60) A further embodiment of the invention relates to the use of *Ophioglossum* as functional food or food supplement for human and/or animals for specific diseases and conditions, wherein the diseases and conditions are those recited in embodiments (19) to (27).

(61) A further embodiment of the invention relates to the use of *Ophioglossum* as functional food or food supplement for human and/or animals, wherein the dosage of *Ophioglossum* is such that it contains the compound of embodiment (14), i.e. tripentadecanoin or Compound C in an amount from 1 (microgram)/day to 50 mg/day. In a further embodiment, the dosage is from 1 (microgram)/day to 20 mg/day. The lower limits are for instance 1 µg (microgram)/day, 2 µg (microgram)/day, 3 µg (microgram)/day, 4 µg (microgram)/day, 5 (microgram)/day, 7 µg (microgram)/day, 10 µg (microgram)/day, 20 µg (microgram)/day, 25 µg (microgram)/day, 50 µg (microgram)/day, 100 µg (microgram)/day, 200 µg (microgram)/day, 300 µg (microgram)/day, 400 µg (microgram)/day or 500 µg (microgram)/day. The upper limits are for instance 50 mg/day, 40 mg/day, 30 mg/day, 20 mg/day, 10 mg/day, 5 mg/day, 3 mg/day, 2 mg/day, 1 mg/day, 900 µg (microgram)/day. It is to be understood that each upper limit can be combined with each lower limit. In one embodiment, the dosage is from 1 µg (microgram)/day to 20 mg/day. In another embodiment, the dosage is from 1 µg (microgram)/day to 900 µg (microgram)/day.

Alternatively, the invention relates to the use of *Ophioglossum* as functional food or food supplement for human and/or animals, wherein *Ophioglossum* is contained as 10 mg/day to 2000 mg/day of dry *Ophioglossum* powder. The lower limits are for instance 10 mg/day, 20 mg/day, 30 mg/day, 40 mg/day, 50 mg/day, 100 mg/day, 150 mg/day, 200 mg/day, 300 mg/day. The upper limits are for instance 2000 mg/day, 1800 mg/day, 1600 mg/day, 1500 mg/day, 1250 mg/day, 1000 mg/day. It is to be understood that each upper limit can be combined with each lower limit.

The way of using herbs in herbal medicines is well known in the art. Therefore, the skilled person is aware of treating *Ophioglossum* in order to use it according to the embodiments (48) to (61).

*Ophioglossum* can be used in the form of a powder of the dried plant or plant parts, in particular root, stalk, leaf, flower, pollen, spore, epidermis or seed. Moreover, extracts may be produced with organic solvents, in particular with lipophilic organic solvents. Useful are EtOH, DMSO, chloroform, dichloromethane, methanol, 2-propanol, aliphatic hydrocarbons, acetone, methyl acetate etc. The extracts can also be dried, or can consist in the form of an oil. General methods for the production of extracts and tinctures are for instance disclosed in R. Voigt, "Pharmazeutische Technologie", Deutscher Apotheker Verlag Stuttgart, ISBN 978-3-7692-6194-3, 2015.

In summary, the present invention can also be formulated as follows:

(i). A compound of the formula (I)

wherein $R^1$, $R^2$ and $R^3$ are independently selected from H or —C(O)$R^4$, wherein $R^4$ is
($C_5$-$C_{20}$) alkyl, which is optionally mono-, di- or trisubstituted with OH, $NH_2$, $NHCH_3$, $N(CH_3)_2$, F or Cl; or
($C_5$-$C_{20}$) alkenyl, bearing 1, 2 or 3 double bonds;
whereby at least one of $R^1$, $R^2$ and $R^3$ is —C(O)$R^4$ with $R^4$ being ($C_6$-$C_{20}$) alkyl with an even number of carbon atoms;
or a pharmaceutically acceptable salt thereof, for the use as a medicament for human and/or animals.

(ii). The compound of the formula (I) according to (i), wherein $R^1$, $R^2$ and $R^3$ are independently selected from H or —C(O)$R^4$ and wherein at least one of $R^1$, $R^2$ and $R^3$ is —C(O)R⁴ with R⁴ being ($C_6$-$C_{20}$) alkyl with an even number of carbon atoms for the use as a medicament for human and/or animals.

(iii). The compound of the formula (I) according (i) or (ii), wherein $R^1$, $R^2$ and $R^3$ are independently selected from —C(O)R⁴ with R⁴ being ($C_6$-$C_{20}$) alkyl with an even number of carbon atoms; for the use as a medicament for human and/or animals.

(iv). The compound of the formula (I) according to (i) or (ii), wherein one or two of $R^2$ and $R^3$ are H and the other(s) is/are —C(O)R⁴ with R⁴ being $C_{12}$-alkyl, $C_{14}$-alkyl, $C_{16}$-alkyl, $C_{18}$-alkyl, or $C_{20}$-alkyl for the use as a medicament for human and/or animals.

(v). The compound of the formula (I) according to any one of (i) to (iii), wherein $R^1$, $R^2$, and $R^3$ are —C(O)R⁴ with R⁴ being $C_{14}$-alkyl for the use as a medicament for human and/or animals.

(vi). A metabolite or prodrug of the compound of formula (I) according to (iv), wherein the metabolite or prodrug is HOC(O)$C_{12}$-alkyl, HOC(O)$C_{14}$-alkyl, HOC(O)$C_{16}$-alkyl, HOC(O)$C_{18}$-alkyl or HOC(O)$C_{20}$-alkyl for the use as a medicament for human and/or animals.

(vii). The compound of the formula (I) according to any one of (i) to (vi) for the use in the treatment and/or prevention of neurodegenerative diseases, retinal or optic nerve degenerative diseases, demyelinating diseases, neuromuscular disorders and muscular dystrophy, brain or spinal cord nerve injury, cranial nerve disorders, or seizures, amyloid deposit related diseases, chronic diseases or conditions selected from the group consisting of kidney diseases, diabetes, asthma and dyspnea, and for the use of anti-aging or life-span prolongation and improving brain function.

(viii). The compound of the formula (I) according to any one of (i) to (vi) for the use in the treatment and/or prevention of neurodegenerative diseases which are selected from the group consisting of Alzheimer's disease (AD), Parkinson's disease (PD), Huntington's disease (HD), Amyotrophic lateral sclerosis (ALS), dementia, Dementia with Lewy bodies (DLB), frontotemporal dementia (FTD), Creutzfeldt-Jakob disease, and brain atrophy.

(ix). The compound of the formula (I) according to any one of (i) to (vi) for the use in the treatment and/or prevention of optic and retinal degenerative diseases which are selected from the group consisting of optical atrophy, Leber's hereditary optic neuropathy (LHON), Dominant Optic Atrophy (DOA), age-related macular degeneration, glaucoma and retinitis pigmentosa.

(x). The compound of the formula (I) according to any one of (i) to (vi) for the use in the treatment and/or prevention of demyelinating diseases which are selected from the group consisting of adrenoleukodystrophy, multiple sclerosis, optical neuritis, Acute Inflammatory Demyelinating Polyneuropathy (AIDP), Chronic Inflammatory Demyelinating Polyneuropathy (CIDP), Guillian-Barre syndrome, encephalitis caused by or related to Zika virus, cranial nerve palsy, neuromyelitis optica (NMO), acute disseminated encephalomyelitis, acute necrotizing hemorrhagic encephalitis, concentric sclerosis, diffuse sclerosis, metachromatic leukodystrophy, ball-like cell leukodystrophy, spongy degeneration of the central nervous system, adrenal leukodystrophy, Perry-plum disease, Alexander disease, radiation injury leukoencephalopathy, hypoxic leukoencephalopathy, periventricular leukomalacia disease, arteriosclerotic cortex under encephalopathy, progressive multifocal leukoencephalopathy, and central pontine myelinolysis syndrome.

(xi). The compound of the formula (I) according to any one of (i) to (vi) for the use in the treatment and/or prevention of neuromuscular disorders and muscular dsytrophy which are selected from the group consisting of myasthenia gravis, Lambert-Eaton syndrome, Duchenne muscular dystrophy, Becker muscular dystrophy, facioscapulohumeral muscular dystrophy, myotonic dystrophy, Charcot-Marie-Tooth disease (CMT).

(xii). The compound of the formula (I) according to any one of (i) to (vi) for the use in the treatment and/or prevention of neurological injury related diseases or mixed neurological diseases selected from the group consisting of acute or chronic brain injury or spinal cord nerve injury, cranial nerve disorders and seizures.

(xiii). The compound of the formula (I) according to any one of (i) to (vi) for the use in the treatment and/or prevention of amyloid deposit related diseases which are selected from the group consisting of diabetes, cardiac amyloidosis, primary amyloidosis, familial amyloidosis, senile systemic amyloidosis (SSA), secondary amyloidosis, and haemodialysis-associated amyloidosis.

(xiv). The compound of the formula (I) according to any one of (i) to (vi) for the use in the treatment and/or prevention of chronic diseases selected from the group consisting of kidney diseases, diabetes, and asthma.

(xv). The compound of the formula (I) according to any one of (i) to (vi) for the use in the treatment and/or prevention of the diseases and conditions of (vii) to (xiv), wherein the treatment dosage is from 1 mg/day to 1000 mg/day.

(xvi). A pharmaceutical composition for the use in the treatment and/or prevention of the diseases and conditions of (vii) to (xiv), wherein the composition contains the compound of the formula (I) of (i) to (vi) and a pharmaceutically acceptable carrier.

(xvii). Use of the compound of the formula (I) according to any one of (i) to (vi) for the manufacture of a medicament for the treatment and/or prevention of the diseases and conditions of (vii) to (xiv).

(xviii). A method for treating and/or preventing of the diseases and conditions of (vii) to (xiv), comprising administering to a patient an effective amount of the compound of the formula (I) according to any one of (i) to (vi).

(xix). Use of the compound of the formula (I) according to any one of (i) to (vi) as functional food or food supplement for human and/or animal.

(xx). Use of the compound of the formula (I) according to any one of (i) to (vi) as functional food or food supplement for human and/or animal, wherein the dosage is from 1 µg (microgram)/day to 50 mg/day.

(xxi). *Ophioglossum* for the treatment and/or prevention of the diseases and conditions of any one of (vii) to (xiv).

(xxii). *Ophioglossum* for the treatment and/or prevention of the diseases and conditions of any one of (vii) to (xiv), wherein the compound of (v) is contained in an amount of 1 mg/day to 1000 mg/day.

(xxiii). A pharmaceutical composition for the use in the treatment and/or prevention of the diseases and conditions of (vii) to (xiv), wherein the composition contains *Ophioglossum*. Emb, (50)

(xxiv). Use of *Ophioglossum* as functional food or food supplement for human and/or animal.

(xxv). Use of *Ophioglossum* as functional food or food supplement for human and/or animal, wherein the compound of (v) is contained in an amount of 1 (microgram)/day to 50 mg/day.

CONCLUSION

Surprisingly, the inventors have found that the administration of lipids bearing fatty acids with odd number of carbon atoms have presented neuroprotective effects. In particular Compound C (SBC003, tripentadecanoin) originated from an herb called *Ophioglossum* or human/animal milk were particularly efficacious in the neuron models, showing very potent neuroprotective, anti-apoptotic, neuro-rescuing, axon outgrowth and potential neuro-regenerative effects. Compound C presented a strong effect on preventing and/or clearing the age-induced protein aggregation during normal yeast ageing. The results from the Camptothecin model suggest that compound C may play a significant protective role at the gene level. A functional food containing Compound C (SBC003, tripentadecanoin) was particularly efficacious in the volunteers of patients with incurable diseases, showing very potent neuroprotective, anti-apoptotic, neuro-rescuing, and neuro-regenerative effects, accordingly it has potential to be used as a medicament and/or functional food for the treatment and/or prevention of neurodegenerative diseases and other chronic diseases.

Surprisingly the inventors have also shown that an herb called *Ophioglossum* (herb B, SBC002) was particularly efficacious in the neuron models and patients, showing very potent neuroprotective, anti-apoptotic, neuro-rescuing, anti-oxidative and neuro-regenerative effects. *Ophioglossum* extract presented a strong effect on preventing and/or clearing the age-induced protein aggregation during normal yeast ageing. The results from the Camptothecin model suggest that *Ophioglossum* extracts may play a significant protective role at the gene level. It has potential to be used as a medicament and functional food for the treatment and/or prevention of neurodegenerative diseases and other chronic diseases.

FIG. 1 relates to Example I-1—neuroprotective effects of Compound C (added alone or 48 hours before AβO treatment) based on cell viability evaluated with MTT Mouse primary cortical neurons were pre-incubated for 48 h with vehicle, 0.05 μM DHA (used as positive control) or different concentrations of Compound C. Then, cortical neurons were treated for 24 h with vehicle (FIG. 1 left) or 1 μM AβO (FIG. 2 right) and cell viability was determined using the MTT assay (n=3 determinations per condition, 1 independent experiment). Data are represented as % of vehicle control (Mean±SD).

Figure 2:
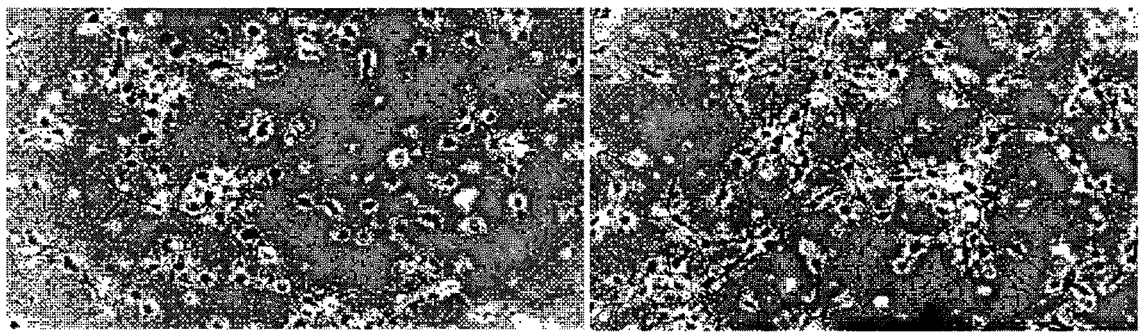
FIG. 2 relates to Example I-1 and shows neuroprotective effects of Compound C—microscopic images of neurons.

FIG. 2 relates to Example I-1—neuroprotective effects of compound C—microscopic images of neurons Left: vehicle control added for 48 hours, then adding AβO control for 24 hours; Right: compound C at 320 nM added for 48 hours, then adding AβO for 24 hours FIG. 3 relates to Example I-2—axon growth effects of Compound C Mouse primary cortical neurons were pre-incubated for 48 h with vehicle, 60 nM sAPPα (used as positive control) or different concentrations of Compound C. Then, cortical neurons were treated for 24 h with vehicle. Data are represented as % of vehicle control (Mean±SD).

Figure 4:
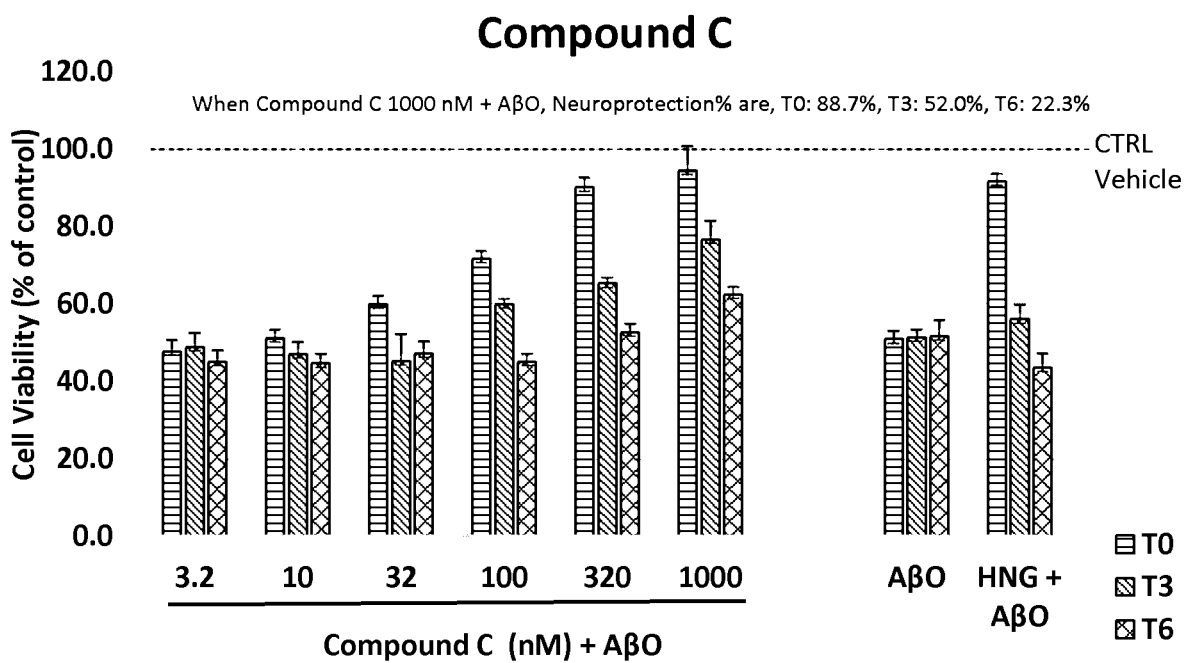
FIG. 4 relates to Example I-3 and shows neuroprotective, anti-apoptotic and neuro-rescuing effects of Compound C in mouse primary neuron models when added concomitantly or 3, 6 hours after A$\beta$O treatment.

FIG. 4 Relates to Example I-3—neuroprotective, anti-apoptotic and neuro-rescuing effects of Compound C in mouse primary neuron models when added concomitantly Or 3, 6 hours after AβO treatment Mouse primary cortical neurons were treated at 0 h (T0) with vehicle or 1 μM AβO. Different concentrations of Compound C or HNG (0.1 μM, used as positive control) were added concomitantly to AβO at 0 h (T0), 3 h (T3) or 6 h (T6) after AβO. Then, cortical neurons were incubated for 24 h and cell viability was determined using the MTT assay (n=3 determinations per condition, 1 independent experiment). Data are represented as % of vehicle control (Mean±SD).

Figure 5A:
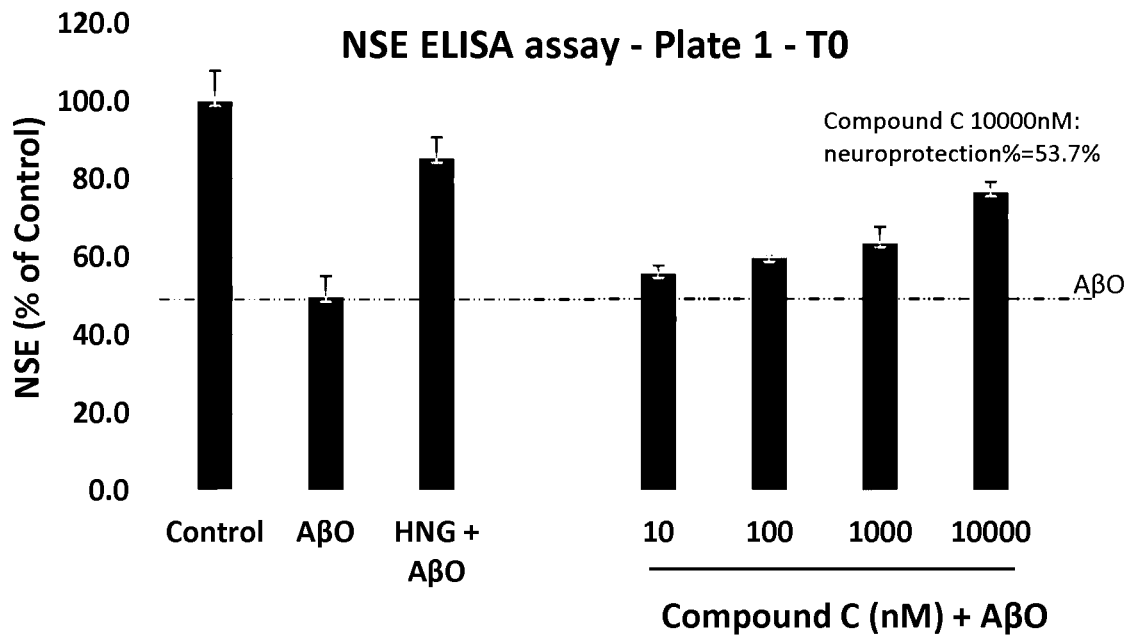
FIGS. 5a to 5c relate to Example I-4 and show neuroprotective, anti-apoptotic and neuro-rescuing effects of Compound C in human induced pluripotent stem cells (iPSCs) when added concomitantly or 3, 6 hours after A$\beta$O treatment.
Figure 5B:
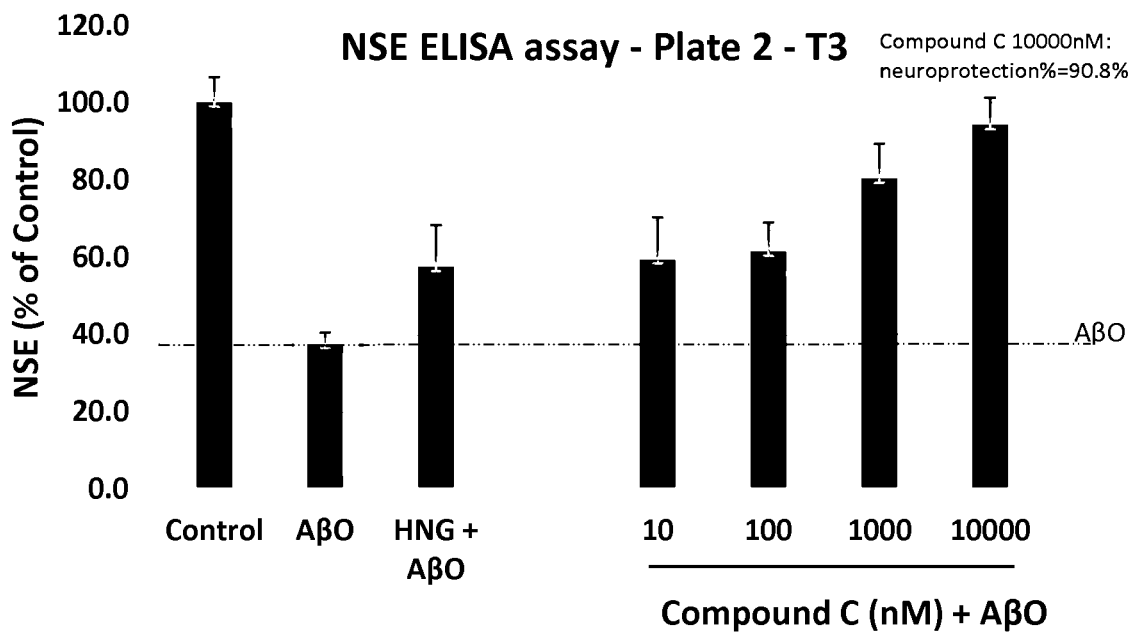
Figure 5C:
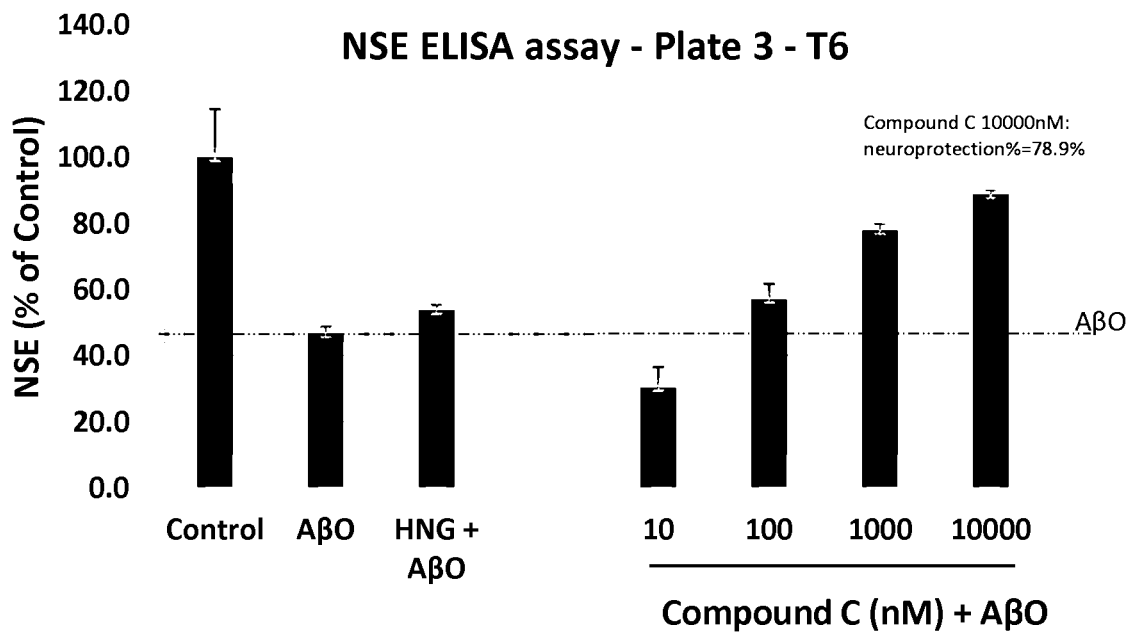

FIG. 5 (FIGS. 5a, 5b and 5c) relates to Example I-4—neuroprotective, anti-apoptotic and neuro-rescuing effects of Compound C in human induced pluripotent stem cells (iPSCs) when added concomitantly or 3, 6 hours after AβO treatment iPSCs were treated at 0 h (T0) with vehicle or 1 μM AβO. Different concentrations of Compound C or 0.1 μM HNG (used as positive control) were added concomitantly to A≈O at 0 h (T0), 3 h (T3) or 6 h (T6) after AβO. Then, were incubated for 24 h and cell viability was determined using the NSE ELISA assay (n=6 determinations per condition, 1 independent experiment). Data are represented as % of vehicle control (Mean±SD).

FIG. 6 (FIGS. 6a, 6b, 6c, 6d, 6e, 6f, 6g, 6h, 6i) relates to Example I-5—neuroprotective, anti-apoptotic and neuro-rescuing effects of Compound C in multiple toxins treated mouse primary neuron models when added at 3 hours after Toxin treatment Cortical neurons were treated at 0 h (T0) with vehicle or multiple neuron toxins. Different concentrations of Compound C or 0.1 μM HNG (0.1 μM, used as positive control) were added at 3 h (T3) after toxins treatment. Then, cortical neurons were incubated for 24 h and cell viability was determined using the MTT assay (n=3 determinations per condition, 1 independent experiment). Data are represented as % of vehicle control (Mean±SD).

Figure 7:
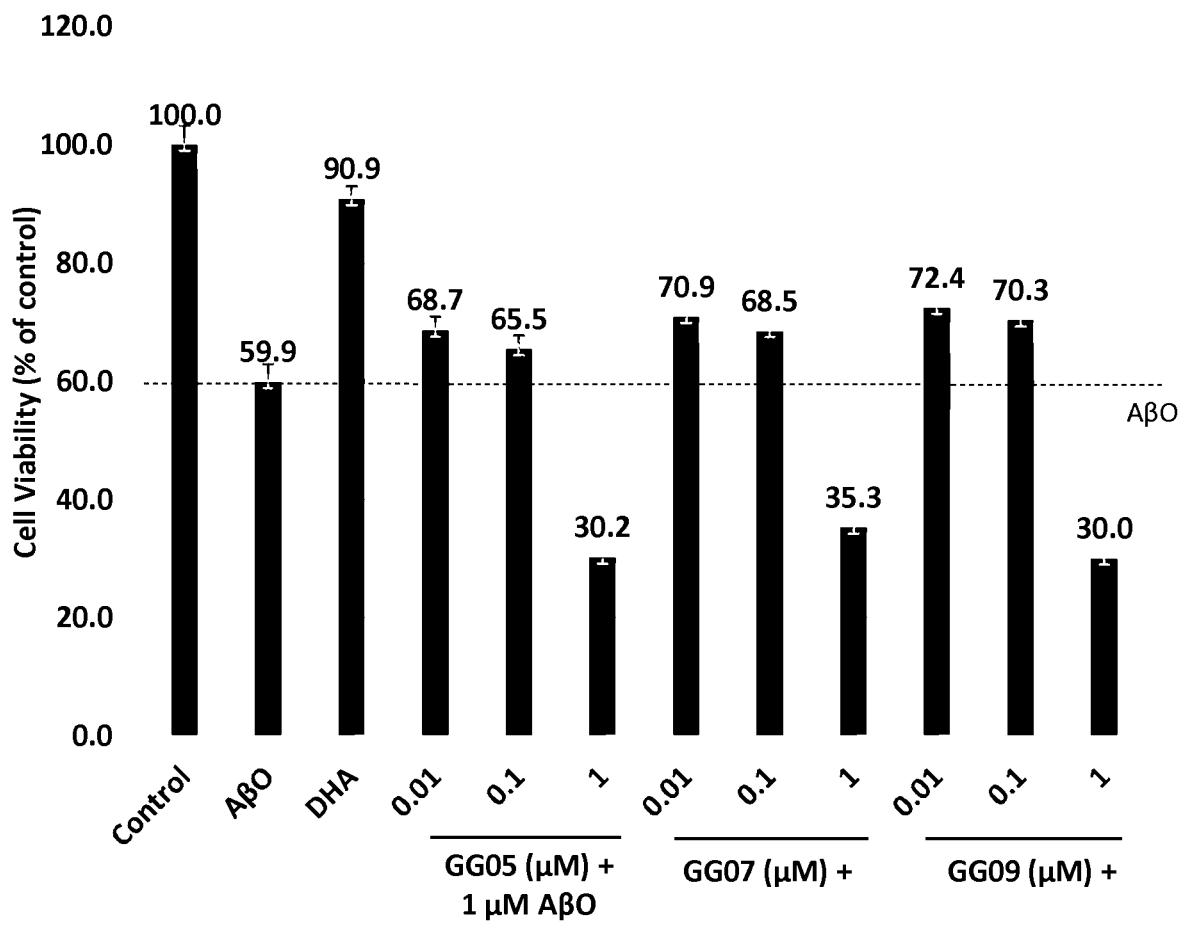
FIG. 7 relates to Example I-6 and shows neuroprotective effects of different fatty acids with odd number of carbons in A$\beta$O treated mouse primary neuron models—when added at 48 hours before A$\beta$O treatment.

FIG. 7 relates to Example I-6—neuroprotective effects of different fatty acids with odd number of carbons in AβO treated mouse primary neuron models—when added at 48 hours before AβO treatment Mouse primary cortical neurons were incubated with vehicle or 1 μM AβO in the absence or presence of different fatty acids with odd number of carbons at 1 μM) for 48 hours. Then AβO (1 μM Aβ1-42 oligomers) or vehicle were added for 24 h. AβO-induced neurotoxicity was evaluated using MTT assay. Data are represented as % of vehicle control (Mean±SD).

Figure 8:
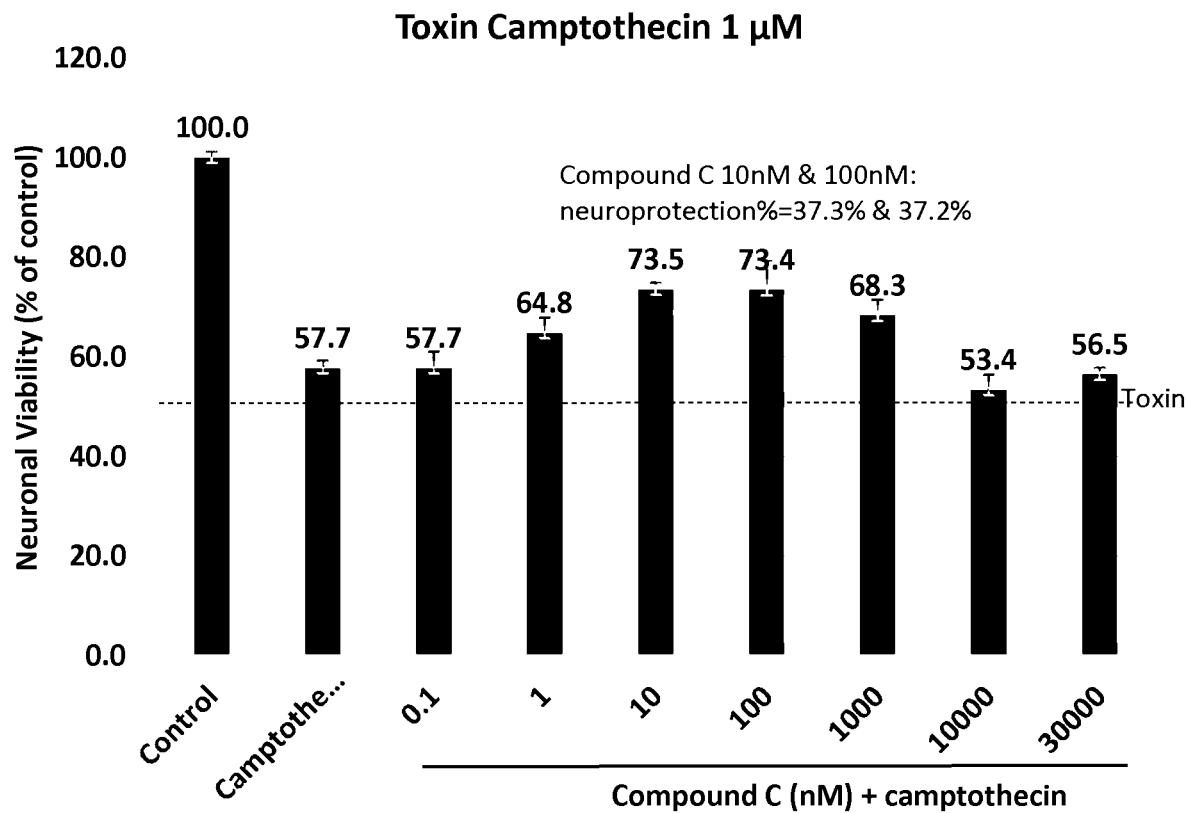
FIG. 8 relates to Example I-7 and shows neuroprotective effects of Compound C in camptothecin treated mouse primary neurons—when added at 48 hours before camptothecin treatment.

FIG. 8 relates to Example I-7—neuroprotective effects of Compound C in camptothecin treated mouse primary neurons—when added at 48 hours before camptothecin treatment Mouse primary neurons were incubated with vehicle or toxins in the absence or presence of different concentrations of compound C added 48 hours before toxin's challenge. After the addition of toxins, cells were further incubated for 24 h.

FIG. 9 (FIGS. 9a, 9b, 9c, and 9d) relates to Example I-8—The effects of Compound C and Herb B extracts in age-induced protein aggregates in *Saccharomyces cerevisiae*

Figure 9A:
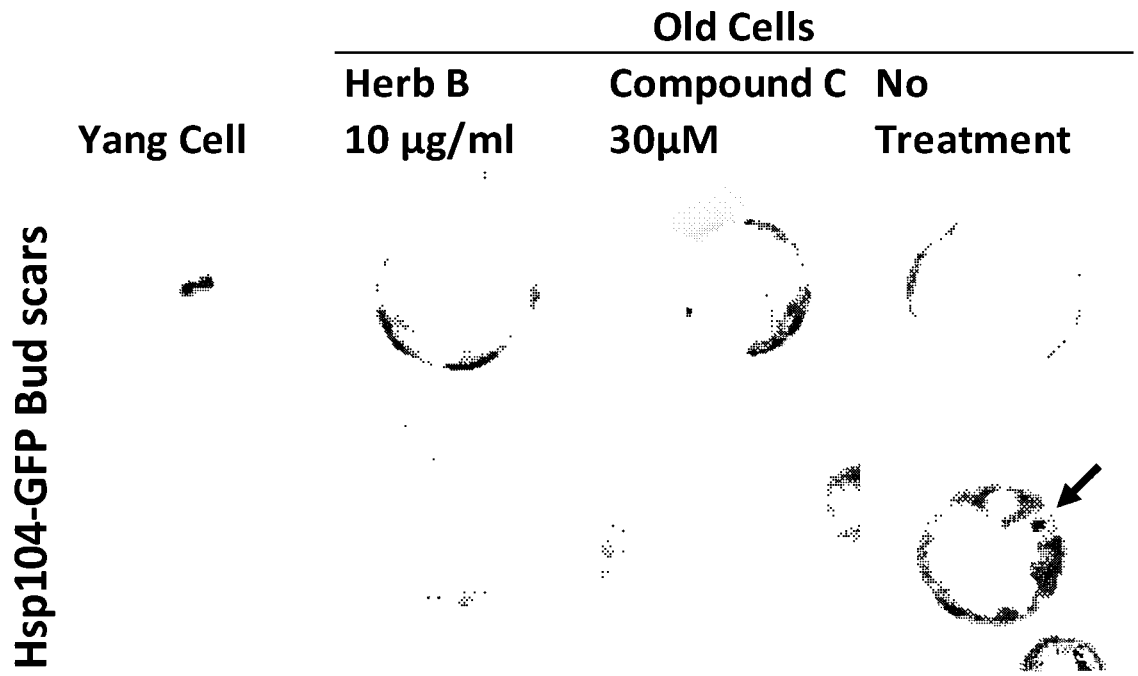
FIGS. 9a to 9d relate to Example I-8 and show effects of Compound C and Herb B extracts in age-induced protein aggregates in *Saccharomyces cerevisiae*.

FIG. 9a: Representative images of a young cell, or old cells untreated or treated with Herb B (10 μg/ml) or Compound C (30 μM). Upper panels are maximum projection of z-series stacks of cells stained with fluorescent brightener 28 and imaged in the DAPI channel to reveal bud scars. Lower panel are single focal planes images of the same cells that express Hsp104-GFP and imaged in the GFP channel. Arrow point at an Hsp104-GFP focus.

Figure 9B:
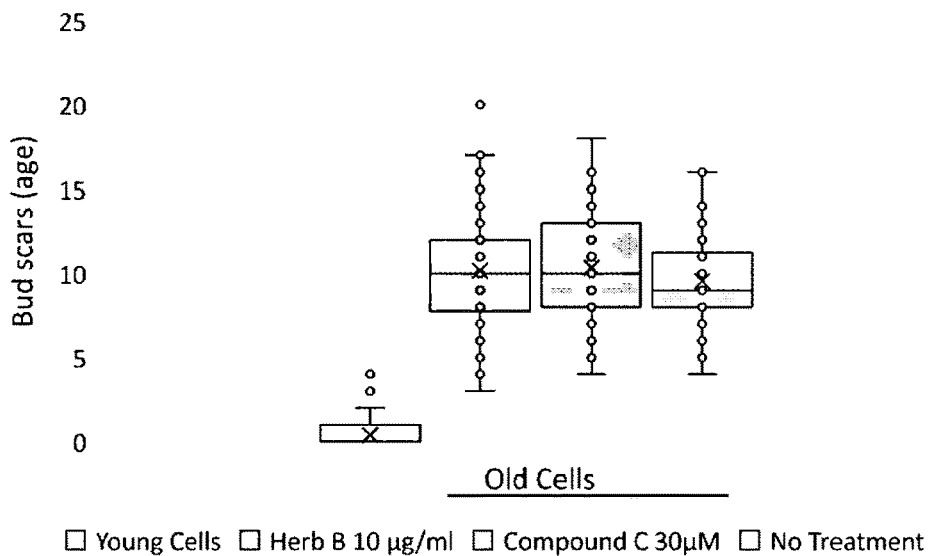

FIG. 9b: Quantification of age of old cells obtained in all conditions tested. Young cells obtained through an exponentially growing culture had an average age of 0.383±0.5952. The number of cells analyzed varied from 73 to 342.

Figure 9C:
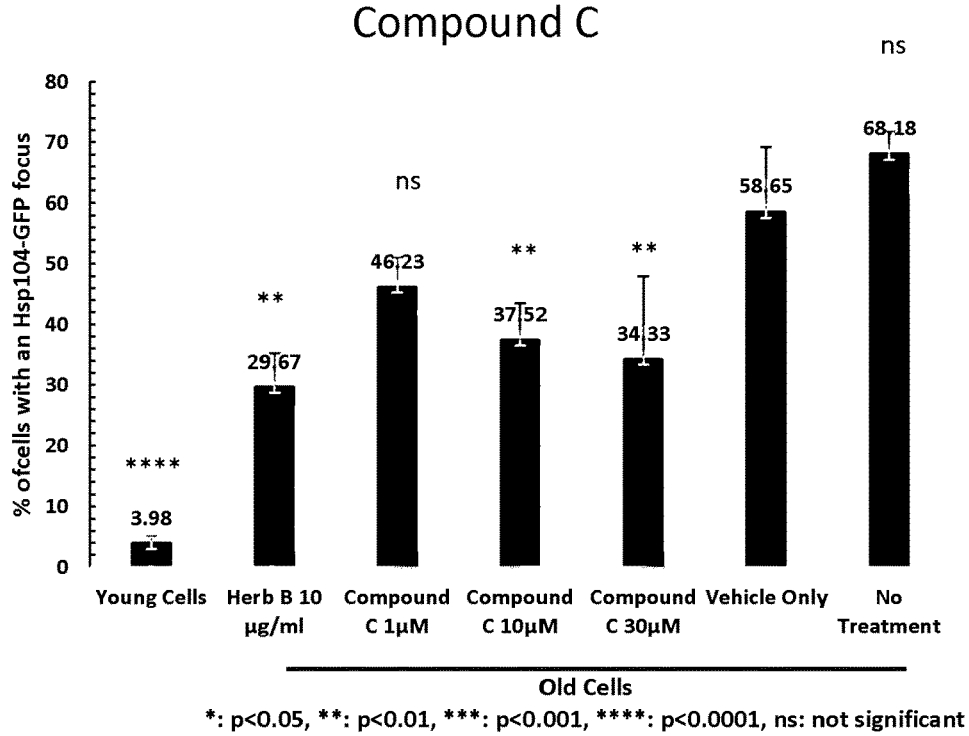

FIG. 9c: Percentage of cells with an Hsp104-GFP focus. Cells were imaged with the same illumination conditions. All old cells imaged were included (between 75 and 94 cells). All focal planes were examined. Mean±SD. P values are adjusted p values from an ANOVA comparing to vehicle only.

Figure 9D:
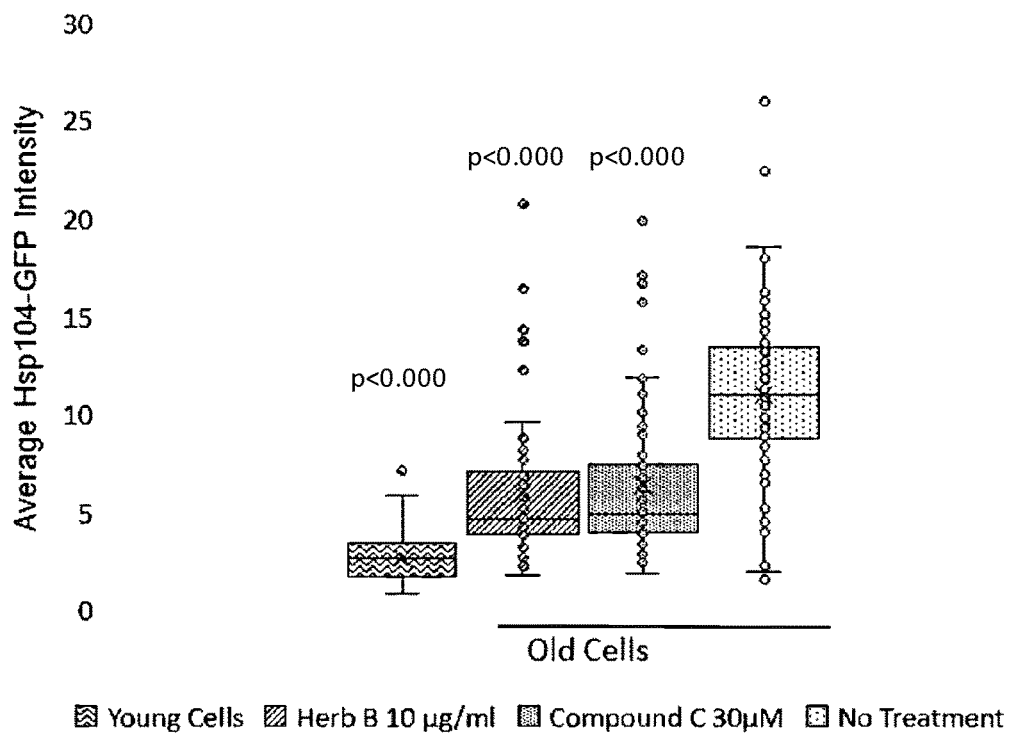

FIG. 9d: Average fluorescence intensity of Hsp104-GFP in the cell as a proxy for Hsp104-GFP concentration. Mean±SD. P values are adjusted p values obtained from ANOVA comparing to vehicle only.

Figure 10:
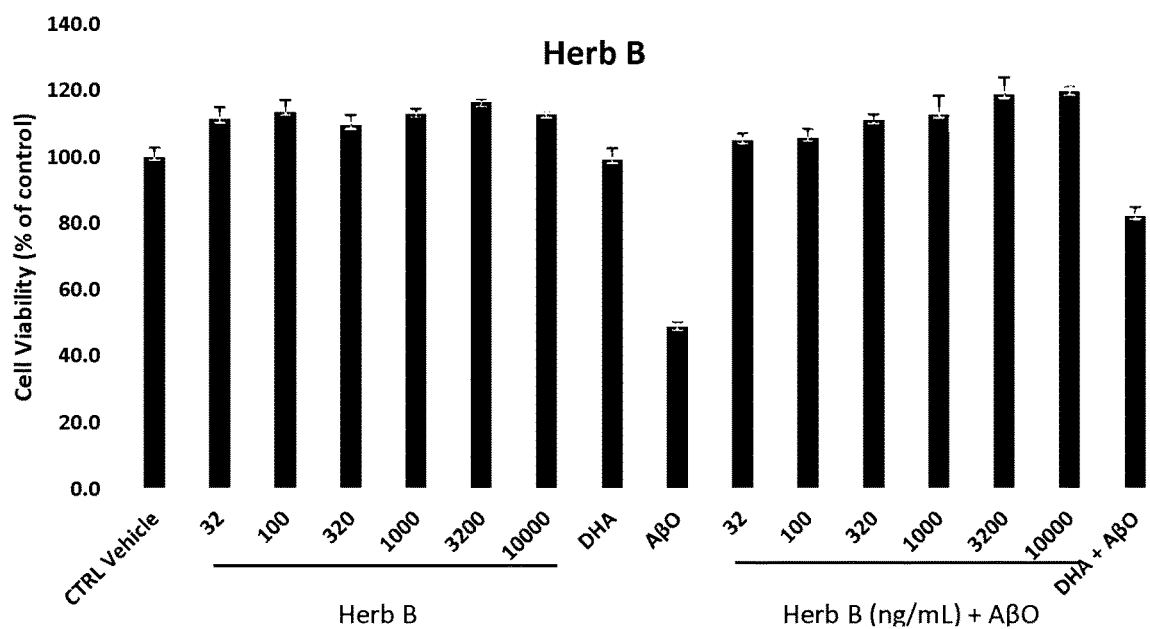
FIG. 10 relates to Examples IV-1 and show neuroprotective effects of Herb B extracts in A$\beta$O treated mouse primary neurons—when added at 48 hours before A$\beta$O treatment.

FIG. 10 relates to Examples IV-1—neuroprotective effects of Herb B extracts in AβO treated mouse primary neurons—when added at 48 hours before AβO treatment Mouse primary cortical neurons were pre-incubated for 48 h with vehicle, 0.05 μM DHA (used as positive control) or different concentrations of Herb B Extracts. Then, cortical neurons were treated for 24 h with vehicle (FIG. 10 left) or 1 μM AβO (FIG. 11 right) and cell viability was determined using the MTT assay (n=3 determinations per condition, 1 independent experiment). Data are represented as % of vehicle control (Mean±SD).

Figure 11:
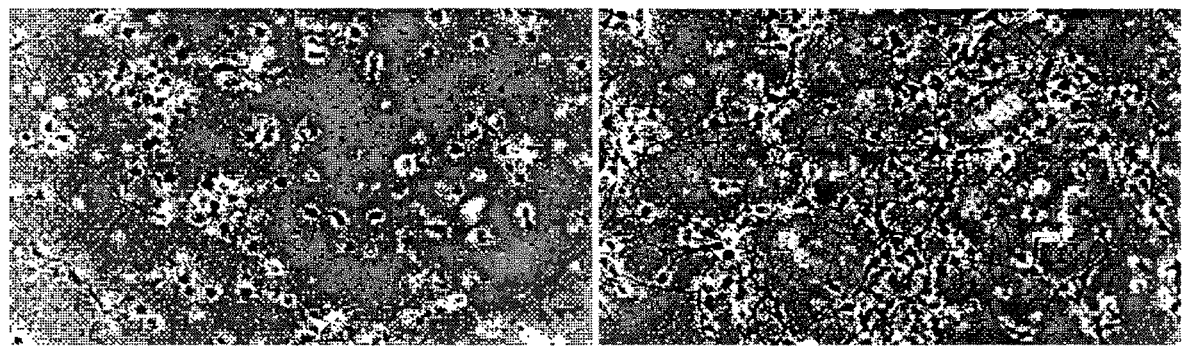
FIG. 11 relates to Examples IV-1 and shows neuroprotective effects of Herb B extracts—microscopic images of neurons.

FIG. 11 relates to Examples IV-1—neuroprotective effects of Herb B extracts—Microscopic Images of Neurons Left: vehicle control added for 48 hours, then adding AβO control for 24 hours; Right: Herb B extracts at 32 ng/mL added for 48 hours, then adding AβO for 24 hours FIG. 12 relates to Examples IV-2—neuroprotective, anti-apoptotic and neuro-rescuing effects of Herb B extracts in Mouse Primary Neuron when added concomitantly, or 3 or 6 hours after AβO treatment Mouse primary cortical neurons were treated at 0 h (T0) with vehicle or 1 M AβO. Different concentrations of Herb B extracts or 0.1 μM HNG (0.1 μM, used as positive control) were added concomitantly to AβO at 0 h (T0), 3 h (T3) or 6 h (T6) after AβO. Then, cortical neurons were incubated for 24 h and cell viability was determined using the MTT assay (n=3 determinations per condition, 1 independent experiment). Data are represented as % of vehicle control (Mean±SD).

Figure 13A:
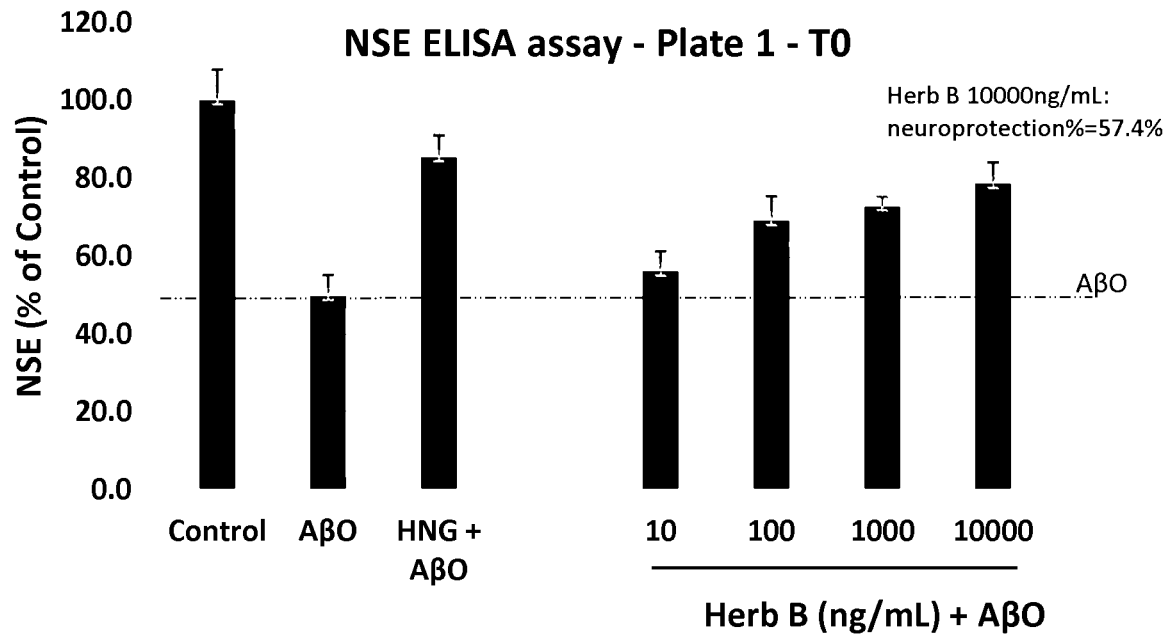
FIGS. 13a to 13c relate to Examples IV-3 and shows neuroprotective, anti-apoptotic and neuro-rescuing effects of Herb B extracts in A$\beta$O treated human induced pluripotent stem cells (iPSCs) when added concomitantly or 3 or 6 hours after A$\beta$O treatment.
Figure 13B:
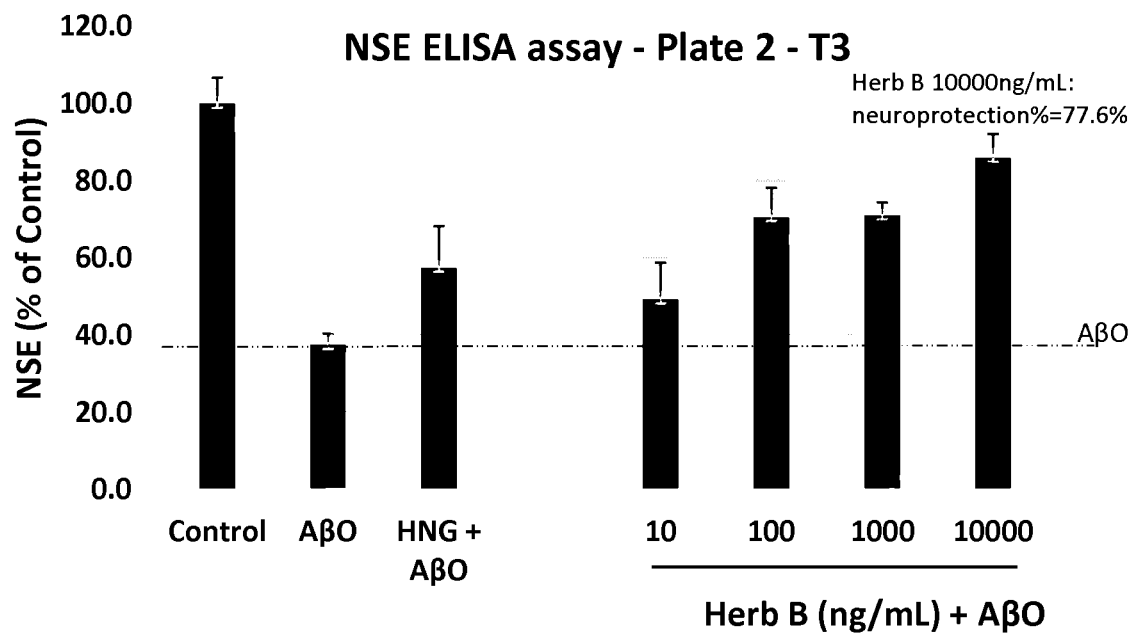
Figure 13C:
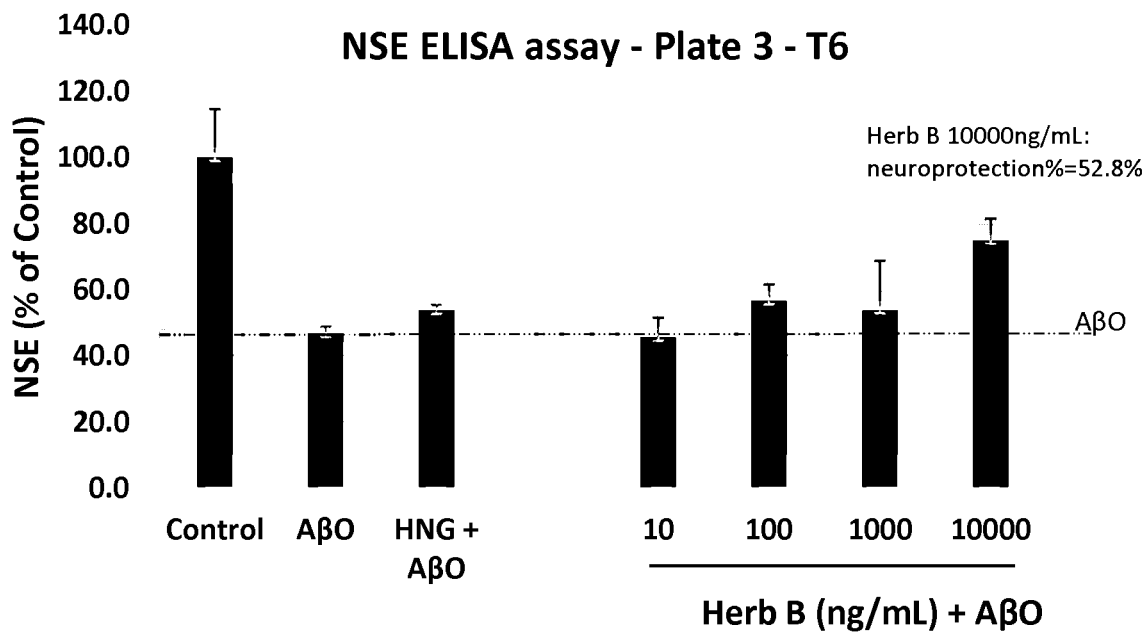

FIG. 13a, 13b, 13c relate to Examples IV-3—neuroprotective, anti-apoptotic and neuro-rescuing effects of Herb B extracts in AβO treated human induced pluripotent stem cells (iPSCs) when added concomitantly or 3 or 6 hours after AβO treatment iPSCs were treated at 0 h (T0) with vehicle or 1 μM AβO. Different concentrations of Herb B or 0.1 μM HNG (used as positive control) were added concomitantly to AβO at 0 h (T0), 3 h (T3) or 6 h (T6) after AβO. Then, were incubated for 24 h and cell viability was determined using the NSE ELISA assay. Data are represented as % of vehicle control (Mean±SD).

FIGS. 14a, 14b, 14c, 14d, 14e, 14f, 14f, relate to Examples IV-4—neuroprotective, anti-apoptotic and neuro-rescuing effects of Herb B extracts in multiple neuron toxins treated mouse primary neuron models—when added at 3 hours after toxins treatment Cortical neurons were treated at 0 h (T0) with vehicle or multiple neuron toxins. Different concentrations of Herb B or 0.1 μM HNG (0.1 μM, used as positive control) were added at 3 h (T3) after toxins treatment. Then, cortical neurons were incubated for 24 h and cell viability was determined using the MTT assay (n=3 determinations per condition, 1 independent experiment). Data are represented as % of vehicle control (Mean±SD).

Figure 15A:
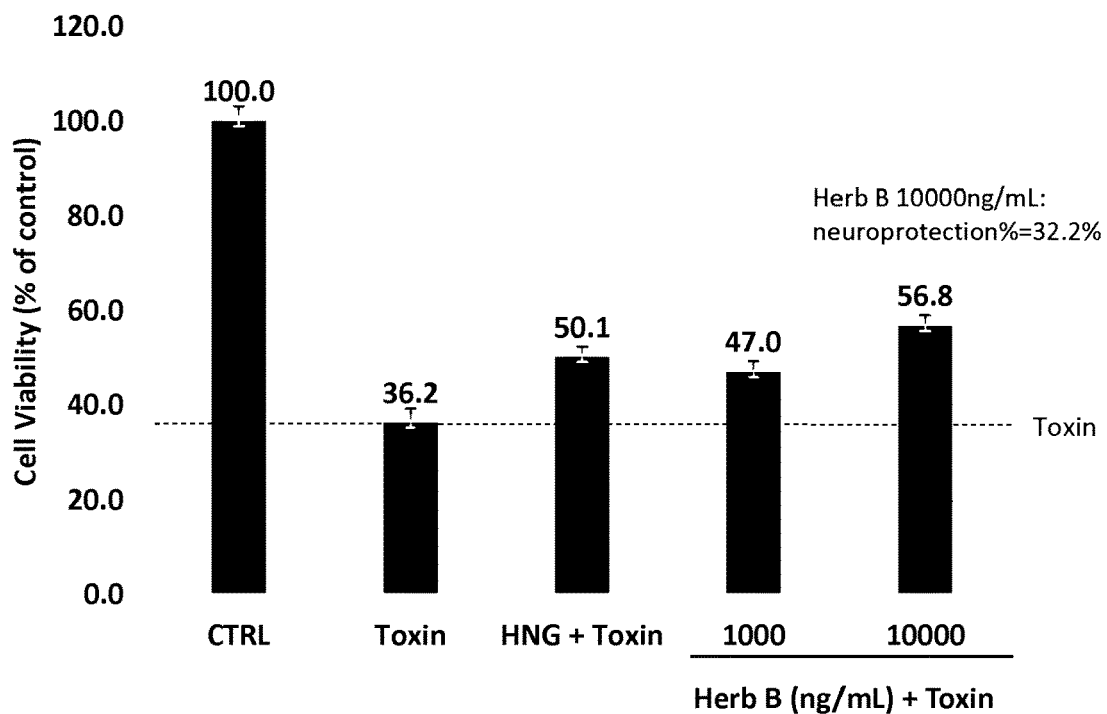
FIGS. 15a and 15b relate to Examples IV-5 and show neuroprotective, anti-apoptotic and neuro-rescuing effects of Herb B extracts in $H_2O_2$ treated mouse primary neuron models—when added at 48 hours before or 3 hours after toxin treatment.
Figure 15B:
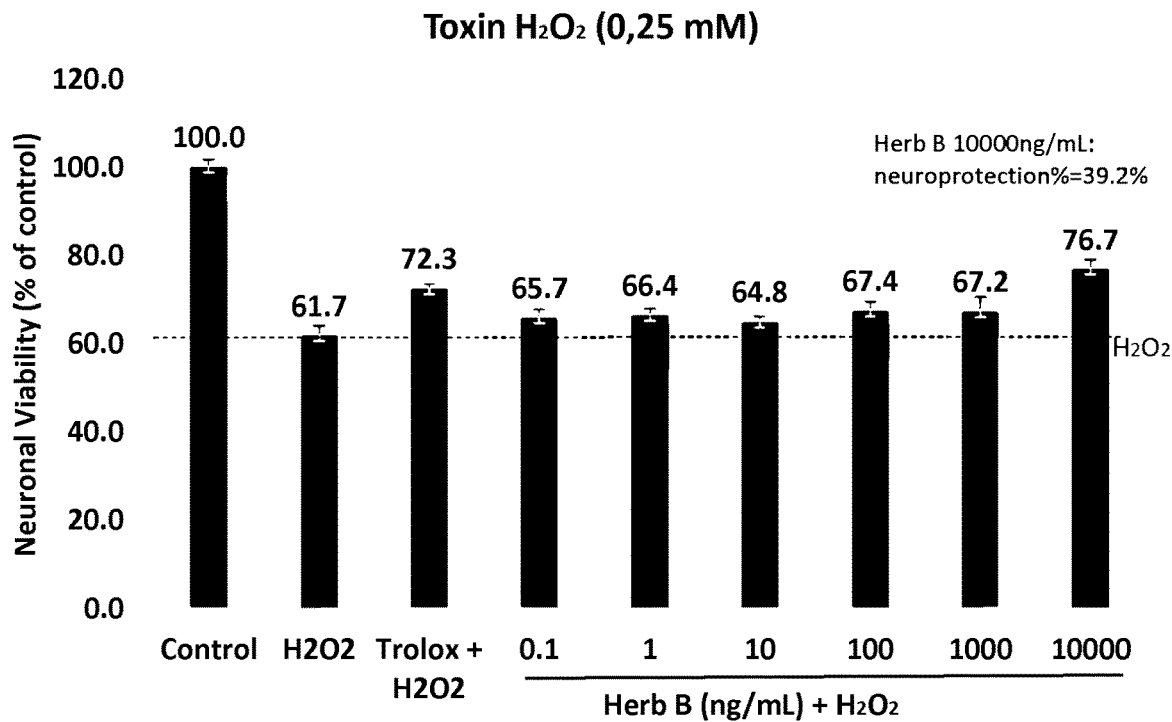

FIGS. 15a and 15b relate to Examples IV-5—neuroprotective, anti-apoptotic and neuro-rescuing effects of Herb B extracts in $H_2O_2$ treated mouse primary neuron models—when added at 48 hours before or 3 hours after toxins treatment FIG. 15a: Mouse primary cortical neurons were treated with vehicle or 0.25 mM $H_2O_2$ treatment. Three hours after $H_2O_2$ treatment, different concentrations of Herb B or Trolox (1 mM, used as positive control) were added into cortical neurons for an incubation up to 24 h. Cell viability was determined using the MTT assay (n=3 determinations per condition, 1 independent experiment). Data are represented as % of vehicle control (Mean±SD).

FIG. 15b: Mouse primary cortical neurons were treated with vehicle or different concentrations of Herb B or Trolox (1 mM, used as positive control) for 48 hours. Then, cortical neurons were incubated with 0.25 mM $H_2O_2$ treatment for a total of 24 h and cell viability was determined using the MTT assay (n=3 determinations per condition, 1 independent experiment). Data are represented as % of vehicle control (Mean±SD).

Figure 16:
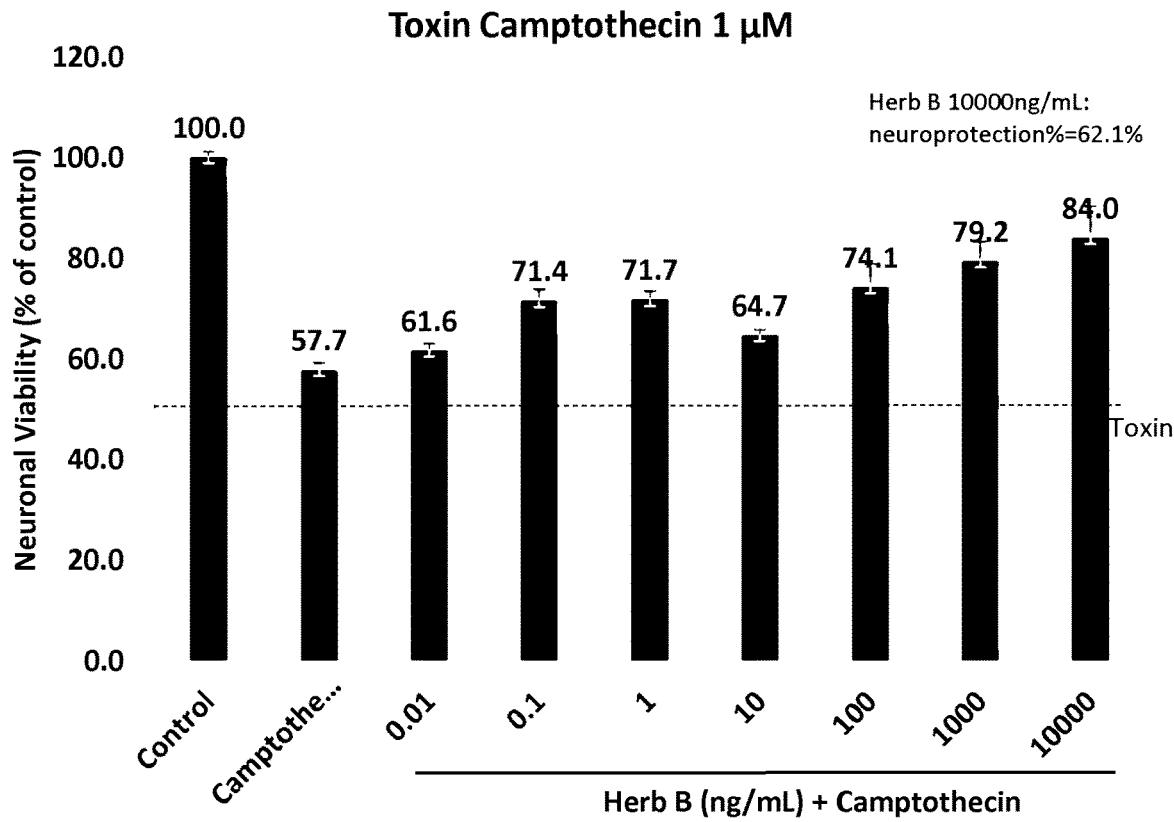
FIG. 16 relates to Example IV-6 and shows neuroprotective, anti-apoptotic and neuro-rescuing effects of herb B extract in camptothecin treated mouse primary neuron models—when added at 48 hours before camptothecin treatment.

FIG. 16 relates to Example IV-6—neuroprotective, anti-apoptotic and neuro-rescuing effects of herb B extract in camptothecin treated mouse primary neuron models—when added at 48 hours before camptothecin treatment Mouse primary neurons were incubated with vehicle or toxins in the absence or presence of different concentrations of Herb B added 48 hours before camptothecin's challenge. After the addition of Camptothecin, cells were further incubated for 24 h. Data are represented as % of vehicle control (Mean±SD).

EXPERIMENTAL PART

Abbreviations and Definitions

AβO Amyloid-β Oligomers
DHA Docosahexaenoic acid
HNG Humanin
iPSC(s) Induced Pluripotent Stem Cell(s)
MTT 3-(4,5-dimethylthiazol-2-yl)-2,5-diphenyltetrazolium bromide
NSE Neuron specific enolase
ELISA Enzyme-linked immunosorbent assay
sAPPα Secreted amyloid precursor protein-α
SD Standard Deviation
SBC003 Compound C, tripentadecanoin (CAS No.: 7370-46-9)
SBC002 Herb B
SBC001 An herb mixture contains SBC002 (i.e. Herb B) and SBC003 (i.e. compound C)

History of Compound C (SBC003)

One embodiment of the present invention relates to the compound of embodiment (14), also called herein "SBC003". This compound has originally been discovered from herb B, i.e. SBC002, which is an *Ophioglossum*. *Ophioglossum* is distributed all over the world in appropriate tropical and subtropical habitats.

Example of SBC003 Extraction Process:

SBC003 was isolated from SBC002 as follows:

1.1 Taking dry substance of SBC002 50 g, using four times volume of 95% of industrial ethanol maceration extracted three times in room temperature, further concentrated under reduced pressure, obtaining in ethanol extract A (estimated 10 g).

1.2 Taking ethanol extract A, using ethyl acetate (2 L) to extract 4 times, further concentrated under reduced pressure, obtaining ethyl acetate extract B (estimated 10 g).

1.3 Taking ethyl acetate extract B, using silica gel column chromatography (petroleum ether: acetone 20:1 to 1:1 gradient elution), obtaining band C1 (estimated 0.1 g).

1.4 Taking C1 strip by silica gel column chromatography (chloroform: methanol 30:1 to 10:1 gradient elution), obtaining C1I strip.

1.5 Taking C1I strip by thin layer chromatography (chloroform: methanol 9:1), obtaining SBC003 (estimated 0.02-0.1 g) with the following chemical structure:

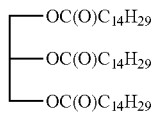

The chemical formula is $C_{48}H_{92}O_6$, named herein as Compound C, SBC003, tripentadecanoin, also known as 1,2,3-Propanetriyl tripentadecanoate, 1,2,3-propanetriyl tripentadecanoate, or 1,2,3-tripentadecanoylglycerol. The molecular weight is 765.24 g/mol (see embodiment (14)).

Examples (I) of Cellular Experiments for Compound C (SBC003)

Example I-1 of Compound C

The Effects of Compound C (Tripentadecanoin, SBC003) in Mouse Primary Neuron Models when Added 48 Hours Prior to AβO Treatment The aim of this study is to determine whether compound C might rescue neuronal death in in vitro neuron models. For that purpose, the neuro-protective effects of compound C at six concentrations were investigated using mouse primary cortical neurons challenged with Aβ1-42 oligomers (AβO). β-Amyloid peptide triggers a variety of pathological changes finally leading to neuronal dysfunction and degeneration in multiple neurological diseases including AD (Deshpande et al. The Journal of Neuroscience, 2006; 26(22):6011-6018).

Cortical neurons from embryonic day 16-17 are prepared from C57BL6/J mouse fetuses. In brief, dissociated cortical cells were plated (50.000 cells/well) in 48-well plates pre-coated with 1.5 μg/mL polyornithine (Sigma). Cells were cultured in a chemically defined Dulbecco's modified eagle's/F12 medium free of serum and supplemented with hormones, proteins and salts. Cultures were kept at 35° C. in a humidified 6% $CO_2$ atmosphere. Mouse cortical neurons were exposed for 24 h to 1.0 μM AβO after a 48-h pre-incubation with vehicle or different concentrations of Compound C. The AβO-induced neurotoxicity was evaluated using the MTT assay.

As expected, the incubation of cortical neurons with 1.0 μM AβO for 24 h resulted in a decreased cell viability by 48.6±1.4%. DHA (0.05 μM, positive control) reduced AβO-induced neuronal death with a remaining cell viability of 82.0±2.6% of control. These control data demonstrate that: i) as expected, DHA protected neurons, and ii) cells challenged with AβO could be successfully prevented by DHA pre-treatment, verifying the test system.

Neurons were pre-incubated with different concentrations of Compound C for 48 h and thereafter treated for 24 h with 1 μM AβO. The results were that in the presence of different concentrations of Compound C resulted in dose-dependent neuroprotective effect (FIG. 1 right and FIG. 2). The maximal neuroprotective effect was 100% at a dilution of the suspension corresponding to 320 nM (cell viability of 111.9±1.5%). The $EC_{50}$ effect is expected around 66 nM.

When neurons pre-incubated for 48 h with different concentrations of Compound C only, showed a trend for a higher cell viability of up to 116.6±3.7% at 1 nM of compound C (FIG. 1 left). Please note the compound C was not fully soluble in stock solutions.

In conclusion, the data suggest that Compound C offer a strong protection toward AβO-induced neurotoxicity. A neuronal-growth-stimulating effect of compound C is observed.

Example I-2 of Compound C

The Effects of Compound C (Tripentadecanoin) of Axonal Growth in Mouse Primary Neuron Models The aim of this study is to test the neurotrophic effects of different concentrations of compound C in mouse primary cortical neurons.

Cortical neurons from embryonic day 16-17 are prepared from C57B16/J mouse fetuses, as described in Example I-1. After 96-h incubation, axonal length is recorded. Briefly, cells were washed with ice-cold PBS and fixed with cold methanol. Following fixation, cells are immunolabelled using a specific antibody detecting total MAP2 protein. Antibodies to MAP2 are excellent markers on neuronal cells, their axons and neuronal dendrites. For quantification of axonal length, six independent images of labelled cells are captured using an inverted microscope. Pictures of cells are analyzed using Neuron-J software and axonal length is recorded manually. A minimum of 100 independent neurons are treated. The data are expressed as mean axonal length (expressed in μm) (Mean±SD). Statistical differences between vehicle-treated cells and cells treated with compounds are determined using a t-test.

Figure 3:
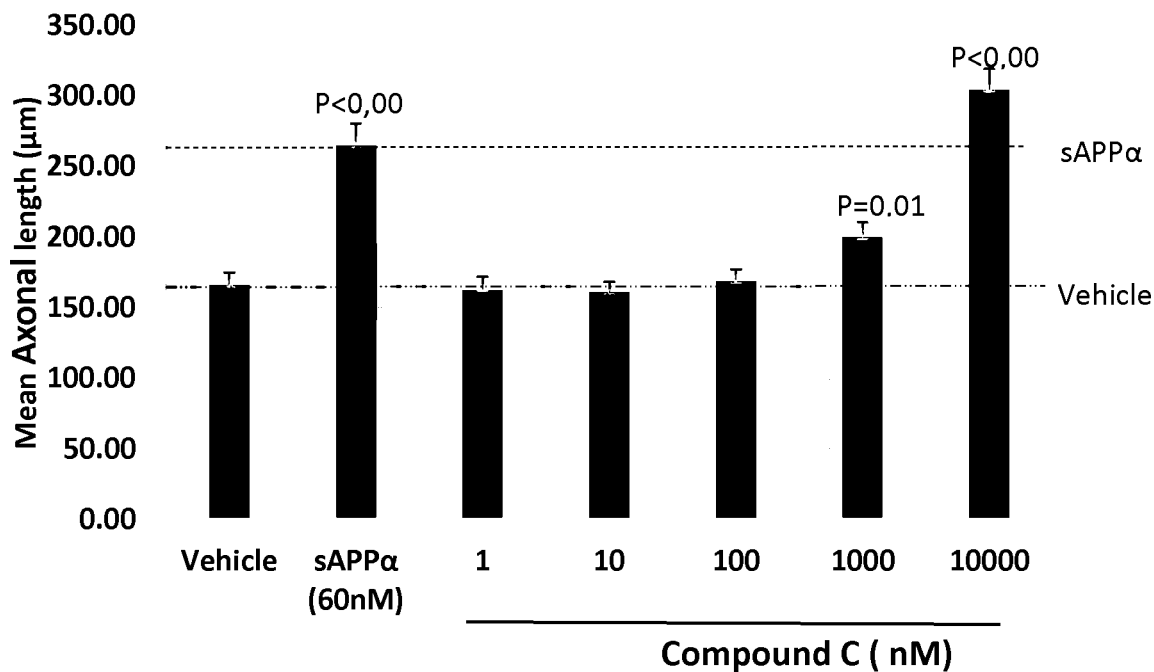
FIG. 3 relates to Example I-2 and shows axon outgrowth effects of Compound C.

As expected, sAPPα (positive control) strongly stimulated neuronal axon outgrowth of 264.63±157.51 μm vs. vehicle control of 165.96±90.18 μm (p<0.0001); while compound C strongly stimulated neuronal axon outgrowth of 304.27±149.60 μm at a concentration of 10000 nM vs. vehicle control (p<0.0001 vs. vehicle control); 199.93±101.17 μm at a concentration of 1000 nM vs. vehicle control (p<0.05 vs. vehicle control). (FIG. 3)

In summary, Compound C (tripentadecanoin) has demonstrated significant axonal growth effects and neurotrophic effects in mouse primary neuron models.

Example I-3 of Compound C

The Effects of Compound C (Tripentadecanoin) in Mouse Primary Neuron Models when Added Concomitantly with AβO or 3, and 6 Hours after AβO Treatment The aim of this study is to determine whether Compound C might present neuroprotective, anti-apoptotic and neuro-rescuing effects in in vitro AβO induced neuron death models. For that purpose, the neuro-protective effects of compound C at six concentrations were investigated using mouse primary cortical neurons challenged with Aβ1-42 oligomers (AβO). Compounds were added at different time points (concomitantly T0 with AβO and T3, or T6 after AβO) with the aim to identify rescuing effects or anti-apoptotic effects.

Cortical neurons from embryonic day 16-17 are prepared from C57B16/J mouse fetuses, as described in Example I-1.

Mouse cortical neurons were exposed for 24 h to 1.0 μM AβO. The AβO-induced neurotoxicity was evaluated using the MTT assay. As expected, the incubation of cortical neurons with 1.0 μM AβO for 24 h resulted in a decreased cell viability by 50.9±2.0%, 51.3±2.0% and 51.7±4.2% for plates 1, 2 and 3 respectively. (FIG. 4)

As expected, humanin peptide (HNG, S14 G variant of humanin peptide, positive control) added at T0 strongly reduced AβO-induced neuronal death with a remaining cell viability of 91.6±2.1% of control (FIG. 4). When added 3 or 6 h after AβO, HNG did not prevent cell death in agreement with historical data. These control data demonstrate that: as expected, HNG protects neuronal cells only when added concomitantly to AβO, verifying the test system.

Neurons were treated with different concentrations of compound C added concomitantly to AβO (T0), 3 h after AβO (T3), or 6 h after AβO (T6). The results were: in all experimental conditions (i.e. T0, T3 and T6), compound C showed dose-dependent neuroprotective effects. For a concentration of 1000 nM, compound C prevented AβO-induced cell death when added concomitantly to AβO (viability of 94.5±4.6%). Moreover, compound C protected from AβO-induced cell death when added 3 h after AβO at concentrations of 320 and 1000 nM (viability of 65.3±2.6% and 76.6±2.9%, respectively) and when added 6 h after AβO at a concentration of 1000 nM (viability of 62.4±3.5%). (FIG. 4)

The percentage of neuroprotection and anti-apoptosis effects was defined as: (neuron viability of compound C group−neuron viability of toxin treated group)/(100−neuron viability of toxin treated group)×100%. The % of neuroprotection and anti-apoptotic effects of compound C at 1000 nM is 88.7%, 52.0%, 22.3%, at T0, T3, or T6, respectively. (FIG. 4)

In summary, the data suggest that compound C offer a strong neuroprotective, anti-apoptotic and neuro-rescuing effects toward AβO-induced neurotoxicity. Compound C discriminate from humanin that it was more potent than humanin to rescue AβO-induced neuronal death.

Example I-4 of Compound C

The effects of Compound C (tripentadecanoin) in AβO treated human induced pluripotent stem cells (iPSC) when added concomitantly or 3 and 6 hours after AβO treatment To determine whether compound C might rescue neuronal death in human iPSC-derived neurons challenged with Aβ1-42 oligomers (AβO). In this cellular model, AβO induce a dramatic neuronal death that could be monitored by the level of neuronal specific enolase (NSE) using a specific ELISA assay. Compound C will be added at different time points (concomitantly and after AβO) with the aim to identify rescuing effects.

Cells (HIP-Neuronal progenitors, GlobalStem, Cat #GSC-4312, Lot #20010260) are plated in 96-well plates at a density of 60.000 cells per well and culture. Before experiments, cells are matured for five weeks and kept at 37° C. in a humidified 5% $CO_2$ atmosphere.

Cells are incubated with vehicle or 1 μM AβO in the absence or presence of different concentrations (i.e. 10, 100, 1000 and 10000 nM) of Compound C added concomitantly to AβO (T0), 3 h after AβO (T3), or 6 h after AβO (T6). Cells are incubated for 24 h in a final volume of 100 μL per well. For positive control, cells are treated similarly in the presence of 0.1 μM HNG (i.e. S14G variant of humanin peptide). In addition, neuronal loss is monitored using the detection of neuronal specific enolase (NSE) by ELISA assay according to supplier's recommendations (Clone-Cloud, Cat #SEA537Hu). A total of three data points per experimental condition will be generated here.

Human iPSC were exposed for 24 h to 1.0 μM AβO. The AβO-induced neurotoxicity was evaluated using the NSE assay. As expected, the incubation of neurons with 1.0 μM AβO for 24 h resulted in a decreased cell viability of 49.7±5.5%, 37.5±3.0% and 46.9±1.9% for plates 1, 2 and 3 respectively.

As expected, humanin peptide (HNG, positive control) added at T0 strongly reduced AβO-induced neuronal death with a neuron viability of 85.3±5.6% of control. When added 3 or 6 h after AβO, HNG did not prevent cell death. These control data demonstrate that: i) as expected, HNG protects neuronal cells only when added concomitantly to AβO, and ii) cells challenged with AβO can be successfully rescued, verifying the test system. (FIG. 5)

IPSCs were treated with different concentrations of Compound C added concomitantly to AβO (T0), 3 h after AβO (T3), or 6 h after AβO (T6). The results were as follows: Compound C in all experimental conditions (i.e. T0, T3 and T6), showed dose-dependent neuroprotective, neuro-rescuing and anti-apoptotic effects. For a concentration of 10000 nM, Compound C prevented AβO-induced cell death when added concomitantly to AβO (cell viability of 76.7±2.7%). Compound C protected from AβO-induced cell death when added 3 h after AβO at concentrations of 10000 nM (cell viability of 94.2±7.1%) and when added 6 h after AβO at a concentration of 10000 nM (cell viability of 88.8±1.3%). The % of neuroprotection and anti-apoptotic effects of compound C at 10000 nM is 53.7%, 90.8%, 78.9%, at T0, T3, or T6, respectively. (FIG. 5)

In conclusion, the data suggest that Compound C offers a strong protection, neuro-rescuing and anti-apoptotic effect toward AβO-induced neurotoxicity in human neurons derived from iPSC. Compound C discriminates from humanin as it was more potent than humanin to inhibit AβO-induced toxicity in this cellular model.

Example I-5 of Compound C

The Effects of Compound C (Tripentadecanoin) in Multiple Neuron Toxins Treated Mouse Primary Neuron Models—when Added at 3 Hours after Toxins Treatment To determine whether compound C might rescue neuronal death in multiple toxin stressed in vitro models. The neuroprotective effects of different concentrations of Compound C was investigated using mouse primary cortical neurons challenged with different types toxins. Compound C was added three hours (T3) after toxins with the aim to identify rescuing effects. Cell viability was investigated using the MTT assay after a 24-h incubation of cells with toxins.

Cortical neurons from embryonic day 16-17 are prepared from C57B16/J mouse fetuses, as described in Example I-1.

Stable oligomeric or fibrillar preparations are prepared according to historical protocols. The source of the different toxins is as follow:
  Aβ1-42 and Aβ325-35 from Bachem (ref H1368 and H1192, respectively).
  Human Tau (2N4R) protein from Evotec.
  Human α-synuclein from r-Peptide (ref 0101008603).
  Amylin from Bachem (ref H-7905.1000)
  Prion Protein$_{118-135}$ from Bachem (ref H-4206, respectively).

All treatments are done in triplicates in 48-well plates at DIV 6/7. Cells were incubated with vehicle or toxins (at the indicated final concentrations) in the absence or presence of different concentrations of Compound C (100, 1000, 10000 nM) added 3 h after toxins (T3). Cells were incubated for 24 h in a final volume of 140 μL per well.

The positives control (added at T3) used was 0.1 µM HNG (S14G variant of humanin peptide) as a well-known antiapoptotic peptide.

Cells were incubated for 24 h before monitoring cell viability using the MTT assay. Briefly, cells were incubated at 35° C. for 1 h with MTT (Sigma, Cat #M2128-10G, Lot #MKBH7489V). For that purpose, 14 µL of 5 mg/mL MTT (solubilized in PBS) are added in each well. After incubation, medium was removed and cells were lyzed with 150 µL DMSO for 10 minutes and protected from light. After complete solubilization of formazan, absorbance at 570 nm is recorded using a Spectrophotometer BMG Labtech Fluostar Omega.

The percentage of neuroprotection and anti-apoptosis effects was defined as: (neuron viability of compound C group−neuron viability of toxin treated group)/(100−neuron viability of toxin treated group)×100%.

Figure 6A:
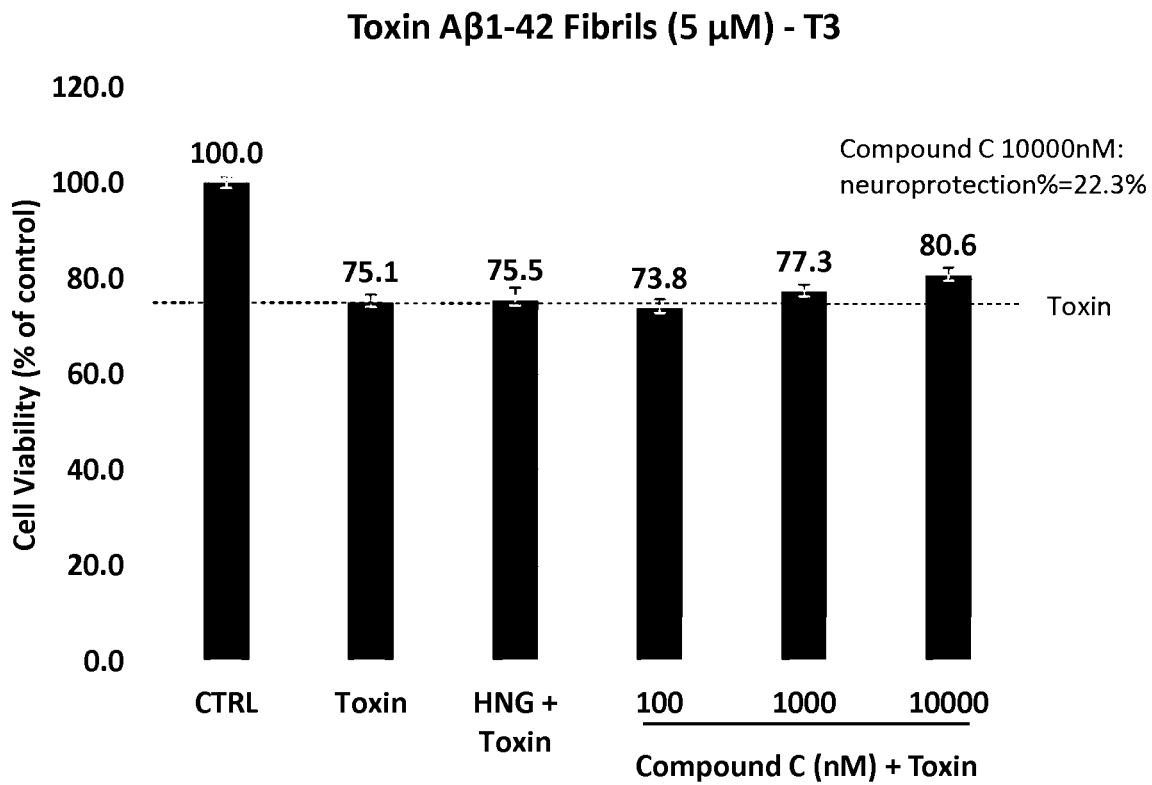
FIGS. 6a to 6i relate to Example I-5 and show neuroprotective, anti-apoptotic and neuro-rescuing effects of Compound C in multiple toxins treated mouse primary neuron models when added at 3 hours after toxin treatment.
Figure 6B:
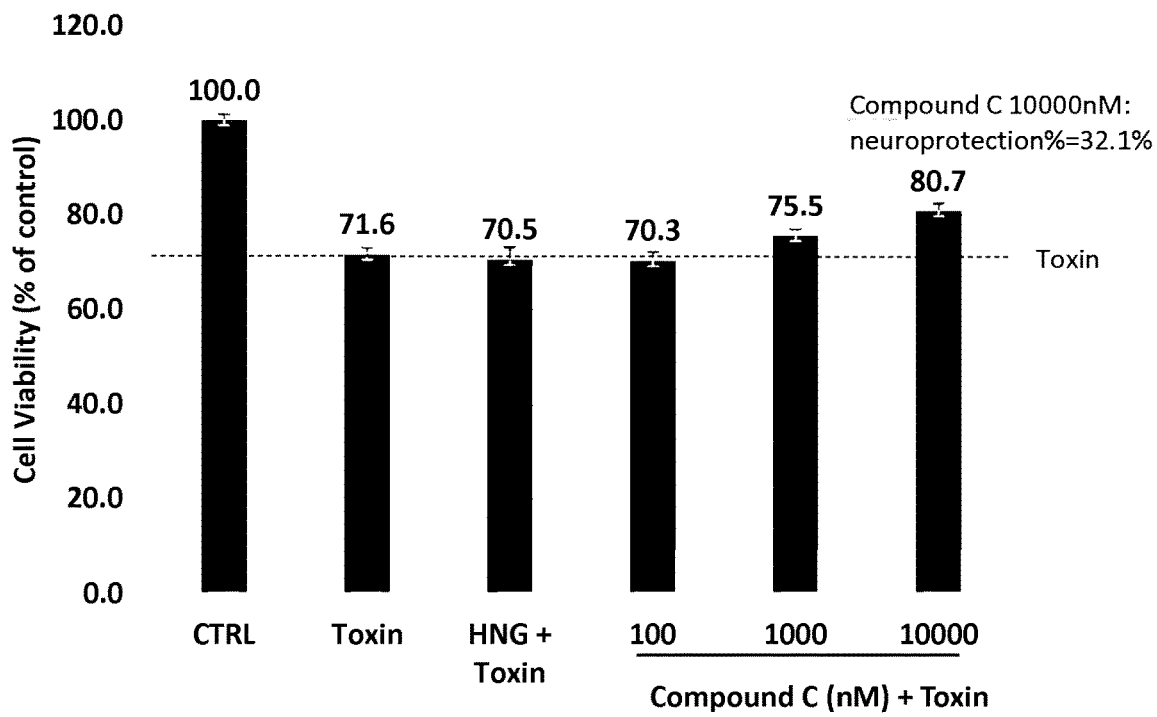
Figure 6C:
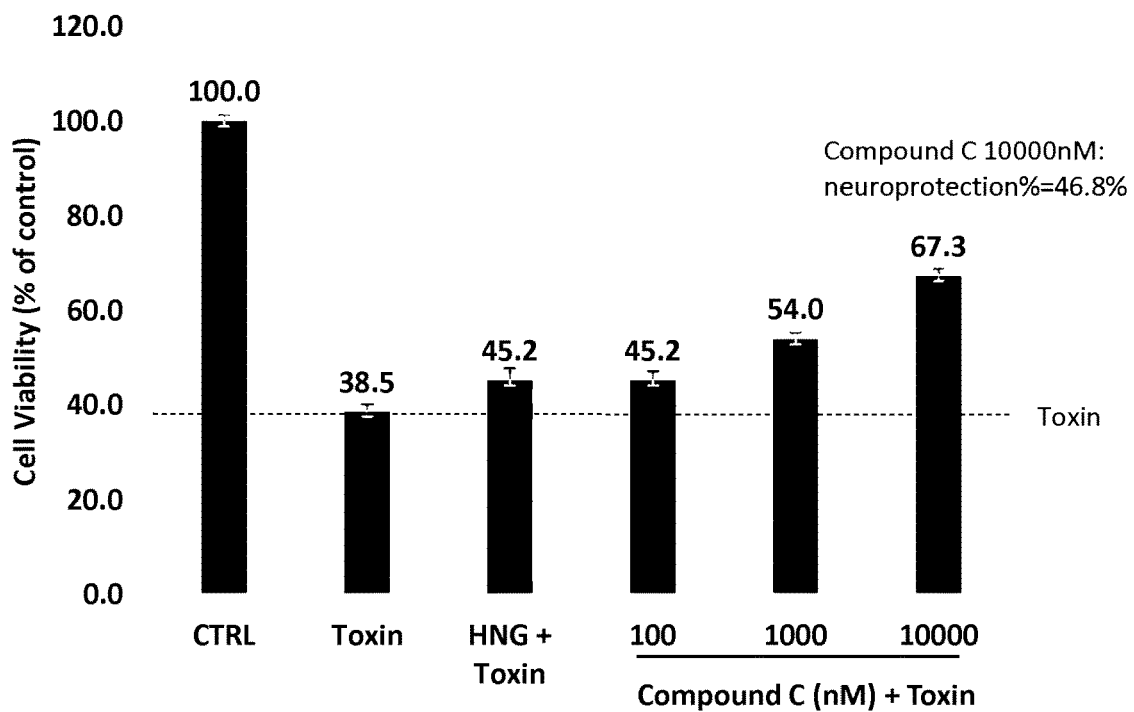

Compound C showed anti-apoptotic and neuroprotective effects against Aβ1-42 fibrils (22.3% at 10000 nM) (FIG. 6a) and Aβ25-35 fibrils (32.1% at 10000 nM) (FIG. 6b).

Figure 6D:
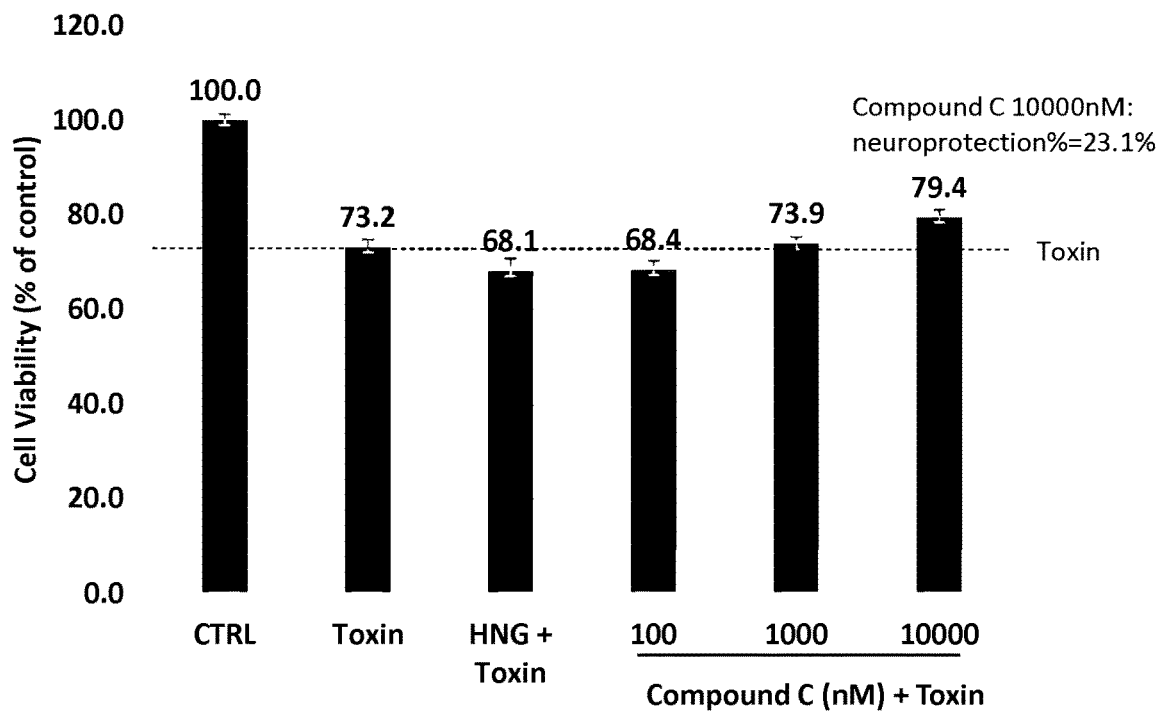
Figure 6E:
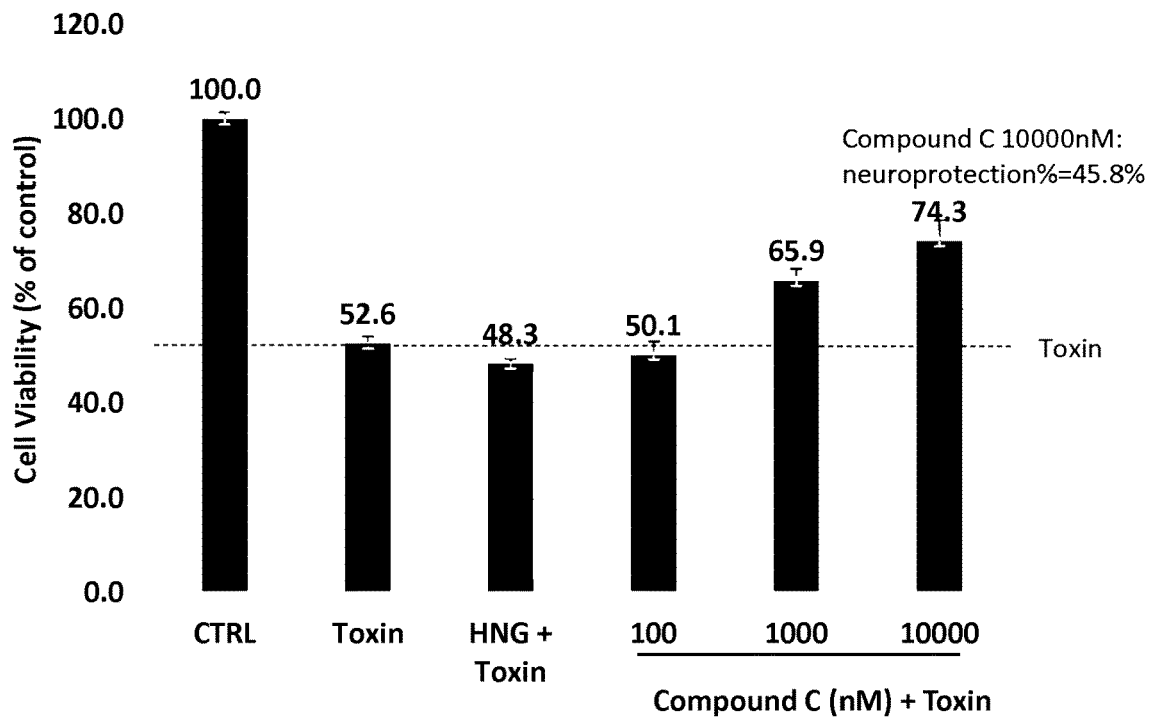
Figure 6F:
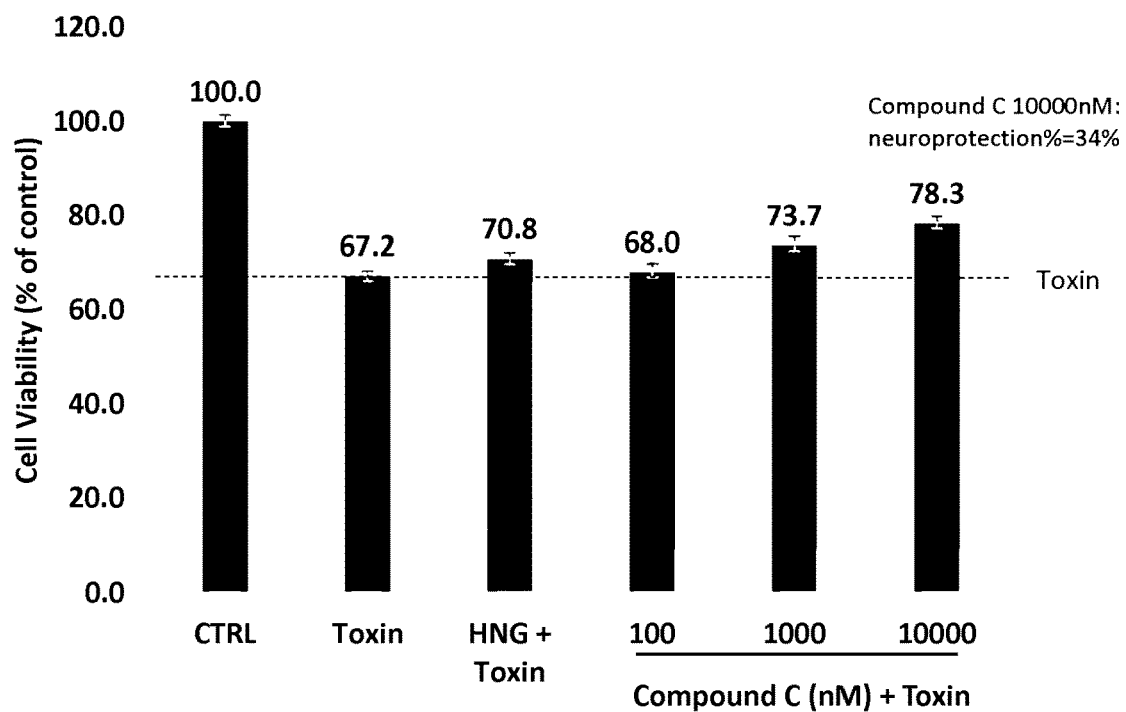
Figure 6G:
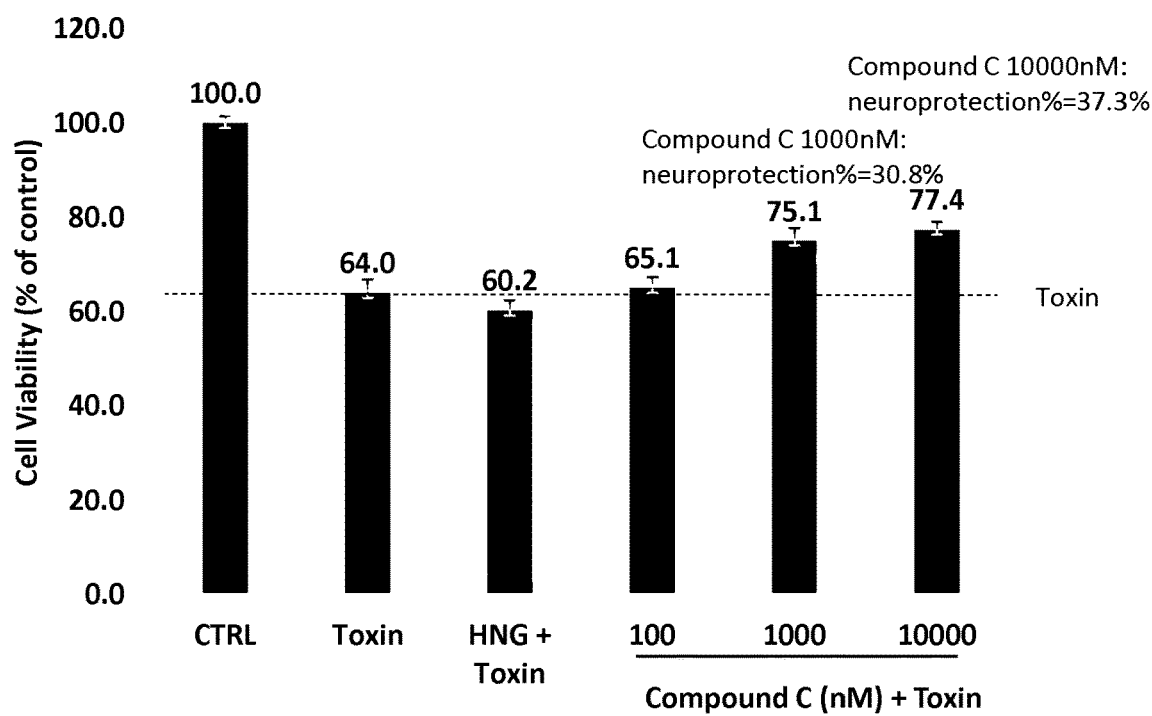

Compound C showed anti-apoptotic and neuroprotective effects against human tau oligomer-induced toxicity (46.8% at 10000 nM) (FIG. 6c) and tau fibril-induced toxicity (23.1% at 10000 nM) (FIG. 6d).

Compound C showed anti-apoptotic and neuroprotective effects against human alpha-synuclein oligomer-induced toxicity (FIG. 6e) (45.8% at 10000 nM) and against alpha-synuclein fibrils (FIG. 6f) (34.0% at 10000 nM).

Figure 6H:
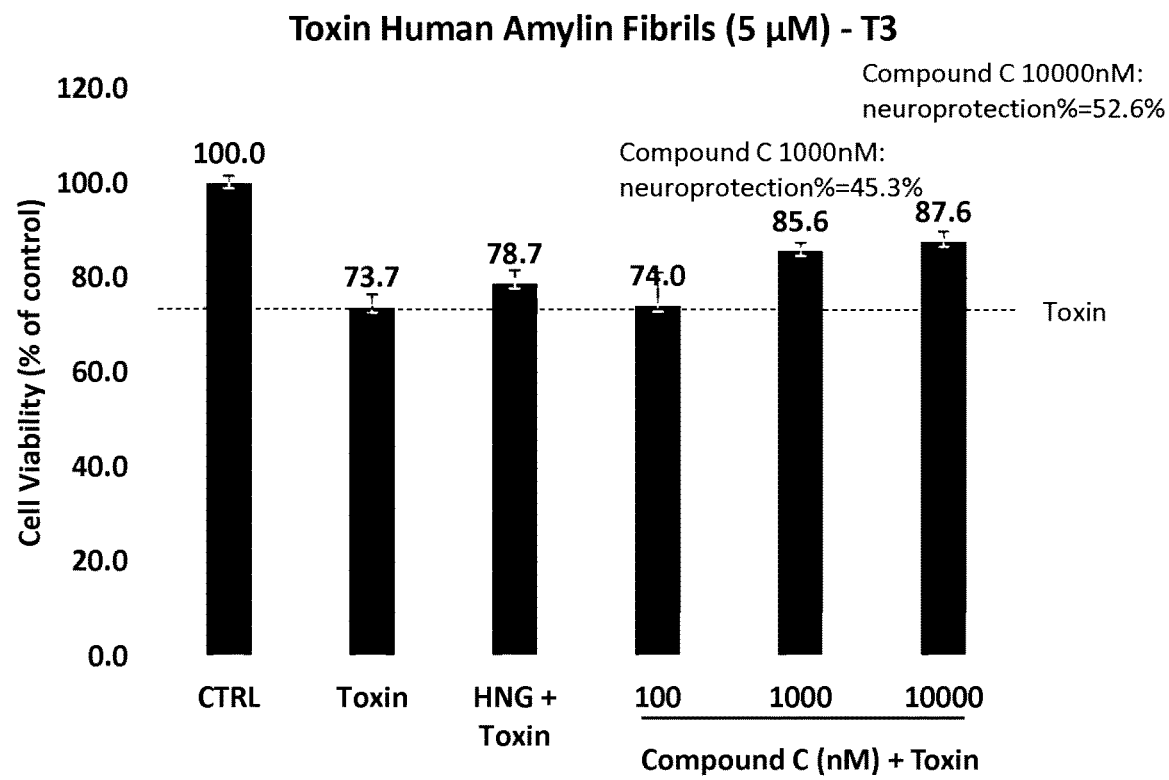

Compound C showed anti-apoptotic and neuroprotective effects against human amylin in both oligomers (30.8%, 37.3% at 1000, 10000 nM, respectively) (FIG. 6g) and fibrils assays (45.3%, 52.6% at 1000, 10000 nM, respectively) (FIG. 6h).

Figure 6I:
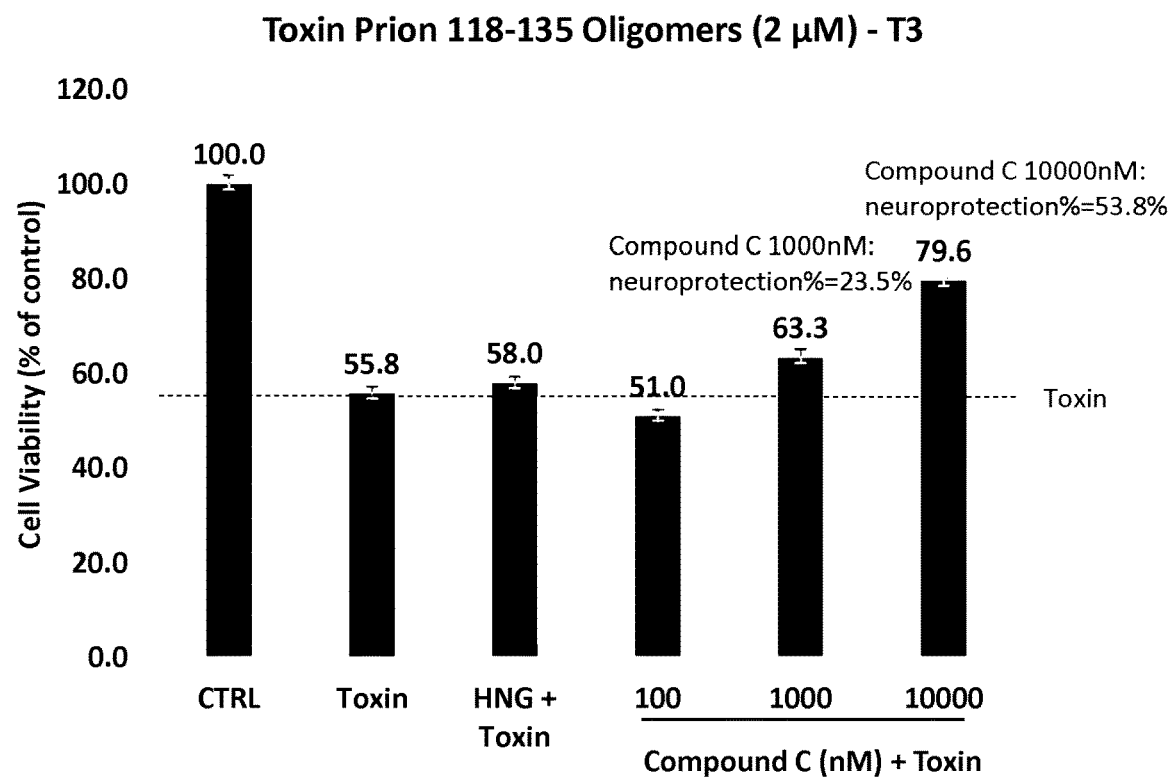

Compound C showed anti-apoptotic and neuroprotective effects against prion oligomer-induced toxicity (23.5%, 53.8%, respectively at 10000 nM) (FIG. 6i).

In conclusion, the data suggest that Compound C offers a strong protective, neuro-rescuing and anti-apoptotic effect toward Aβ1-42 fibrils-, Aβ25-35 fibrils-, human tau oligomer-, human tau fibrils-, human alpha-synuclein oligomer-, alpha-synuclein fibrils-, human amylin oligomers-, human amylin fibrils- and prion oligomers-induced neurotoxicity in mouse primary cortex neurons. Compound C discriminates from humanin as it is more potent than humanin to inhibit multiple toxins-induced neuron deaths in these cellular models.

Example I-6 of Fatty Acids with Odd Number of Carbons

The Effects of Different Fatty Acids with Odd Number of Carbons in AβO Treated Mouse Primary Neuron Models—when Added at 48 Hours Before AβO Treatment The aim of this study was to test if there was any difference in the neuro-protective effects of fatty acids containing odd number of carbons using mouse primary cortical neurons challenged with AβO. Compounds were added 48 hours before treatment with 1 µM AβO, with the aim to identify preventing effects. Cell viability was investigated using the MTT assay after a 24-h incubation of cells with AβO.

Cortical neurons from embryonic day 16-17 were prepared from C57Bl6/J mouse fetuses, as described in Example I-1.

All treatments were done in triplicates in 48-well plates. Cells were incubated with vehicle or 1 µM AβO in the absence or presence of different lipids at the indicated final concentrations) added at 48 hours before AβO. Cells were incubated with AβO for 24 h in a final volume of 140 µL per well.

For positive controls, cells are treated similarly (48 hours before AβO) in the presence of 0.05 µM DHA.

Following AβO-treatment, cell viability was measured using the MTT assay. Briefly, cells were incubated at 35° C. for 1 h with MTT (Sigma, Cat #M2128-10G, Lot #MKBH7489V). For that purpose, 14 µL of 5 mg/mL MTT (solubilized in PBS) were added in each well. After incubation, medium was removed and cells were lyzed with 150 µL DMSO for 10 minutes and protected from light. After complete solubilization of formazan, absorbance at 570 nm was recorded.

Mouse primary cortical neurons were exposed for 24 h to vehicle or 1 µM Aβ1-42 oligomers. AβO-induced neurotoxicity was evaluated using MTT assay. As expected, the incubation of cells with AβO for 24 h resulted in a decreased viability of 59.9±1.7% of control. (FIG. 7)

As expected, the preincubation of cells with 50 nM DHA prevented AβO-induced cell death. Indeed, primary neurons preincubated with 50 nM DHA for 48 h and challenged with 1 µM AβO exhibited a remaining cell viability of 90.9±3.1% of control.

In summary, the 48-h preincubation of cells with lipids with odd number of carbons GG05, GG07 or GG09 resulted in a dose independent neuroprotective effects at 0.01 and 0.1 µM, but lost neuroprotective effect at 1 µM (FIG. 7).

The names and codes of selected fatty acids were listed as follows:

| Compound code in the test | Name | No. of carbons | Neuroprotection (0.01 µM) | Neuroprotection (0.1 µM) |
|---|---|---|---|---|
| GG05 | Pentadecanoic acid | 15 | 21.9% | 14.0% |
| GG07 | Heptadecanoic acid | 17 | 27.4% | 21.4% |
| GG09 | Nonadecanoic acid | 19 | 31.2% | 25.9% |

Example I-7 of Compound C

The Effects of Compound C in Camptothecin Treated Mouse Primary Neuron Models—when Added at 48 Hours Before Camptothecin Treatment The neuro-protective effects of different concentrations of compound C was investigated using mouse primary cortical neurons challenged with camptothecin, which is a cytotoxic quinoline alkaloid which inhibits the DNA enzyme topoisomerase I (topo I).

Cortical neurons from embryonic day 16-17 are prepared from C57Bl6/J mouse fetuses, as described in Example I-1.

Camptothecin is obtained from Sigma, (ref C9911—(S)-(+)-Camptothecin).

Mouse primary neurons were incubated with vehicle or toxins in the absence or presence of different concentrations of compound C added 48 hours before toxin's challenge. After the addition of 1 µM camptothecin, cells were further incubated for 24 h in a final volume of 140 µL per well.

As expected, the incubation of cells with 1 µM camptothecin for 24 h resulted in a decreased cell viability of 57.7±1.6% of control. When preincubated for 48 h before camptothecin-treatment, compound C induced a dose-dependent neuroprotection (bell-shape curve), with a maximal effect at doses of 10 and 100 nM, with a cell viability of 73.5±1.5% and 73.4±5.9% of control, respectively. The neuroprotective and anti-apoptotic effects of compound C at 10 nM, 100 nM are 37.3%, 37.2%, respectively. (FIG. 8)

In conclusion, the data suggest that compound C offers protection toward neuronal death induced by camptothecin.

Example I-8 of Compound C (SBC003) and Herb B (SBC002)

The Effects of Compound C (SBC003) and Herb B (SBC002) on Age-Induced Protein Aggregates in *Saccharomyces cerevisiae*

Background: In most organisms, aging is associated with the accumulation of damaged and misfolded proteins. Pioneering studies from the group of Thomas Nystrom identified that this is also the case in budding yeast (Aguilaniu, et al. 2003 14; 299(5613):1751-3). Carbonylated proteins accumulate in replicative old mother yeast cells. Interestingly, these carbonylated proteins recruit the protein disaggregase Hsp104. Hsp104 is an hexameric ATPases Associated with diverse cellular Activities (AAA+) protein and translocase (Sweeny E A, Shorter J. J Mol Biol. 2016; 428(9 PtB):1870-85). Hsp104 couples ATP hydrolysis to disassembly and reactivation of proteins trapped in soluble preamyloid oligomers, disordered protein aggregates, and stable amyloid or prion conformers. HSP104 is endogenously generated due to aggregation of mis-folded proteins in old cells.

Objective: To understand the mode of action of Compound C (SBC003) and Herb B (SBC002) extracts, the effects of Compound C (SBC003) and Herb B (SBC002) extracts on the formation and maintenance of age-induced protein aggregates in budding yeast system were tested.

Methods: In old yeast cells, age induced protein aggregates recruit a specific set of chaperones and co-chaperones and hence can be easily visualized at the microscope. Hsp104 expressed endogenously as a fusion to the green fluorescent protein tag (Hsp104-GFP) form a focus in these cells. (FIG. 9a)

To test an effect on the formation of age-induced Hsp104-GFP foci, old cells were obtained and cultivated in the presence of Compound C (1 µM, 10 µM and 30 µM), Herb B (10 µg/ml), ethanol (0.3%, vehicle only) or in the absence of any treatment. Untreated young cells were obtained through a simple exponential growth.

Age was determined by staining bud scars with fluorescent brightener 28. In all conditions, old cells had a similar age distribution with an average age of 10 generations (n>73 cells). (FIG. 9b)

Most of the old cells untreated or treated with vehicle only contained one Hsp104-GFP focus (68.2±3.7% and 58.7±10.6% of the cells respectively). Treatment of cells with compound C (SBC003) at either 10 µM or 30 µM significantly reduced the proportion of cells with a Hsp104-GFP focus (37.5±6.0% and 34.3±13.7%, respectively, P<0.001). Treatment with compound C at 1 µM reduced the proportion of cells with a Hsp104-GFP focus, however this reduction was not statistically significant (46.2±4.8%, P>0.05). Treatment of cells with herb B extract (SBC002) presented with a significantly reduced proportion of cells containing an Hsp104-GFP focus (29.7±5.5%, P<0.01). (FIG. 9c).

Since Hsp104 belongs to the arsenal of proteins that counteract and channel protein aggregates to a single protein deposit, the concentration of Hsp104-GFP in old cells in all conditions was measured. The intensity of Hsp104-GFP was much higher in old cells than in young cells. However, compound C and herb B reduced the extent of this increase suggesting that Hsp104-GFP was less concentrated in cells exposed to these compounds. Hsp104-GFP intensity is higher at lower compound C concentration (1 and 10 µM) compared to the highest concentration tested (30 µM) and herb B treatment, correlating with the effect of these treatments on the percentage of cells that have an Hsp104-GFP focus. (FIG. 9d)

In conclusion, compound C and herb B extracts presented a strong effect on preventing and/or clearing the age-induced protein aggregation during normal yeast ageing.

Examples (II) of Functional Food (SBC003)

Compound C (tripentadecanoin) is a natural lipid which can be found in specific herbs, but can also be found in human/animal milk. The patients described in examples II suffered from incurable diseases without any efficient treatment have voluntarily requested the functional food which containing SBC003.

Example II-1 of Functional Food

This case refers to a female Taiwanese at 49 years old who was diagnosed optic atrophy for eight years and who was blind. On Day 1, when she received a form of function food containing SBC003, she felt her vision was brighter and clearer, could differentiate better the objects with sharp black and white contrast. She felt her spirit becoming better. She felt heat flow in her palms and feet. Then she ate a form of function food containing SBC003 about 7 mg/day for 7 days. She could see the chopsticks in front of her eyes when eating; her hands when washing bowls. She felt more sensitive to the lights in darkness. She felt warm in her palms and feet. After about one month, she had a brighter and better vision.

Example II-2 of Functional Food

This case refers to a male Taiwanese at 49 years old. He was diagnosed with amyotrophic lateral sclerosis (ALS) for nine years. He was lying on bed, with ventilator assisted breathing and unable to move a single finger. He could breathe by himself at the most 30 mins/day. He ate a form of function food containing SBC003 about 10 mg/day. About one month he could breathe by himself about 55 mins/day. He felt warm energy in his back.

Example II-3 of Functional Food

This case refers to a male Chinese at 48 years old. He was diagnosed with primary Parkinson's Diseases for 9 years with shaking, rigidity, slowness of movement, and difficulty with walking. He was treated with levodopa, and trihexyphenidyl for eight years with initial effects but lost effects gradually. Three years ago, he was placed with microelectrodes for deep brain stimulation to reduce motor symptoms as the drugs were ineffective. He still presented with symptoms of abnormal shaking in feet, rigidity, slowness of movement, and difficulty with walking. He ate a form of function food containing SBC003 about 10 mg/day. After about one week, his abnormal shaking in feet improved for about 2 weeks. Then he discontinued due to some reasons, afterwards, he re-started for another half month and his symptoms improvement again.

Example II-4 of Functional Food

This case refers to a male Taiwanese at his 49 years old. He was diagnosed as cerebellar atrophy with limb spasm and was paralyzed on bed in need of a 24-hour nursing assistance. He could not smile or speak, could not communicate with others. When people talked with him, he had no facial expressions. He ate a form of functional food containing SBC003 at about 10 mg/day. After about one month, he started to smile, and had facial expressions on his face and even tended to speak when people were talking with him.

Example II-5 of Functional Food

This case refers to a male Chinese with date of birth 22 Sep. 1959. In December-2015, he had severe spinal bones fractures in his thoracic and lumbar spines due to an accidental fall from a 10-meter high building. At that time, he could not walk, could not sit, was paralyzed on bed, lost feelings in his lower legs and had severe pains in lumbar area. After about 6 months, he had a bit improvement and could sit for about 1 hour/time, however other symptoms persisted. His CT showed a diagnosis of "complex burst type compression fracture of the superior end plate of the T11 vertebral body with fracture line extending to the posterior cortex as well as avulsed fracture of the anterior cortex with approximately 40-50% decreases in height with retropulsion of bony material into the spinal canal stenosis, especially at the T10-T11 disc level."

He ate a form of functional food containing SBC003 about 20 mg/day. On Day 1, he felt a stream of heat in his whole spinal area (especially lumbar area) after taking SBC003. For about 10 days, he had great improvement in the following symptoms: 1) remaining lumbar pains reduced to 40% of the pains before taking SBC003; 2) he could sit for up to 2 hours/time compared to only 1 hour/time before taking SBC003. In addition, he often felt a warm stream in his spinal area and his lower legs had less spasms than before.

Example II-6 of Functional Food

This case refers to a female Taiwanese with chronic kidney failure for 10 years and being treated with haemodialysis (three times weekly) for 2-3 years. She did not have any urine. Her serum creatinine was maintained at very high level, with a mean value of 9.21 mg/dl. She ate a form of functional food containing SBC003 about 10 mg/day to 25 mg/day for about 1 month. After about 2 months, she had 10 ml urine once per day; after increasing to 50-100 mg/day for about 2-3 months, she had urine about 2-3 times with a total volume of about 50 ml per day. Her serum creatinine was reduced to 8.88, 8.97, 8.55, 9.12 mg/dl, with an average level of 8.88 mg/dl. Her blood glucose level was also reduced to 70-105 mg/dl compared to 130-180 mg/dl (prior to the treatment).

Example II-7 of Functional Food

This case refers to a male Taiwanese with date of birth of 12 Sep. 1974 who has been diagnosed with asthma for about 29 years. The asthma occurred severely whenever feeling coldness or in early morning or drinking cold water or climbing stairs. For the past 29 years, he was treated with corticosteroids or bronchodilator if asthma attacks. After eating a form of functional food containing SBC003 about 5 mg for one or two time, he felt his symptoms greatly improved. Even if drinking a lot of cold water or feeling coldness, the asthma symptoms did not occur even at time of triggers.

Example II-8 of Functional Food

This case refers to a male Taiwanese with date of birth 4 Jul. 1977 who has diagnosed with asthma for about 20 years. The asthma occurred frequently. He was treated with bronchodilator if asthma attacks, at a frequency of once per two weeks. After eating a form of functional food containing SBC003 about 5 mg/time for about few times. The symptoms of asthma had greatly improved even when at triggers.

Examples (III) of Herb B (SBC002)

The SBC002 used for the treatment of the patients described in EXAMPLES III was made in a form of dried powder of a selected part of *Ophioglossum* thermale, *Ophioglossum petiolatum*, or *Ophioglossum* reticulatum.

Cases Studies of Patients Treated with SBC002

Example III-1 Case SBC002-001

1. Diagnosis in 2002: Optic Neuritis (Left)

Case SBC002-001 refers to a female patient with date of birth of 22 Sep. 1966. She had the first onset of blurred vision in her left eye in 2002 and underwent steroid pulse therapy seven days after onset. However, the vision did not improve and her residual vision was hand motion at 20 cm. There was no limb weakness.

2. Diagnosis in 2007: Optic Neuritis (Right); Optic Atrophy (Left)

On 2 Mar. 2007, she was admitted to China Medical University Hospital (CMUH) because of acute onset of blurred vision of her right eye for two days. The Relative Afferent Papillary Defect (RAPD) sign was positive. Optic neuritis was suspected. She received steroid pulse therapy.

3. Diagnosis in May 2008: optic atrophy (left); optic neuritis (right), probable multiple sclerosis; thoracic myelopathy On 26 Mar. 2008, RNFL Thickness Average Analysis showed 43.51 μm (OS), 77.60 μm (OD); on 19 May 2008 RNFL Thickness Average Analysis showed undetectable (<10 μm) (OS), 72.33 μm (OD).

On 24 May 2008, she had right eye blurred vision with eye pain induced by eye movement for 5 days. Under the impression of optic neuritis (OD), she was admitted for steroid pulse therapy. Magnetic Motor Evoked Potential (MEP) study suggested lesion above the level of left C5 spine; lesion between the levels of right C5 and L2 spines, and lesions below the levels of bilateral L2 spines.

On 27 May 2008, both pattern and goggles visual evoked potential (VEP) studies showed no pickups of waves P100 left stimulations and prolonged latencies with reduced amplitudes in waves P100 with right stimulations. VEP was suggestive of bilateral pre-chiasmal lesions, more prominent at left side. Somatosensory Evoked Potential (SSEP) study showed peripheral nerve lesions in both upper limbs; lesions (s) between the levels of bilateral C5 and L2 spines; and lesion below the level of left L2 spines.

Brain MRI was compatible with the diagnosis of right optic neuritis and showed some high signal finding. After pulse therapy, multiple sclerosis was suspected. On 31 May 2008, she was discharged with diagnosis of optic atrophy (OS); optic neuritis (OD), probable multiple sclerosis; thoracic myelopathy. After being discharged, she was recommended with medications including prednisolone 5 mg bid; mecobalanmin 250 mg Qd; vitamin B12 QID.

4. Diagnosis in August 2008: multiple sclerosis; recurrent right optic neuritis; old left optic neuritis with sequelae of optic atrophy; multiple sclerosis associated myelopathy On 1 Aug. 2008, she had worsening of right eye sight for one month. VEP study performed by pattern shift method: none pickup of VEP wave were seen in left or right eye stimulation respectively. Under the impression of MS, she was admitted for steroid pulse therapy and IFN-1b therapy. She was given steroid pulse therapy and IFN therapy and the symptoms got improved.

5. Diagnosis in January 2009: multiple sclerosis (acute relapse); cervical myelopathy; insomnia; neurogenic bladder.

On 10 Jan. 2009, she had acute onset of neck pain with right-sided weakness for 3 days with a suspect recurrent cervical myelitis. Next day she felt right leg easy spasm and right hand tenderness with numbness, then right-sided weakness was noted. The right hand had difficulties to take pen and chopsticks, right leg difficulty to be raised when walking, and difficulty to up-down stairs. She had received steroid pulse therapy. She felt neck pain subsided, but right-sided still weakness.

6. Diagnosed with cortical atrophy in June 2013

In June 2013, her brain MRI showed that the ventricles and sulci were dilated. Cortical atrophy was diagnosed.

7. Diagnosed with Sjögren's syndrome from January 2014

In January 2014, she had been followed up at neurological OPD in Taichung Hospital, Ministry of Health and Welfare due to progressive deterioration of bilateral blindness, blurred vision, fatiguability, hypesthesia and paresthesia at four limbs and itchy at left forearm. She was diagnosed as Sjögren's syndrome, eczema and mainly received treatment of geniquin (hydroxychloroquine sulfate) 200 mg BID.

8. SBC002 (Herb B) treatment from 21 Dec. 2015 Before 21 Dec. 2015, her both eyes had severely blurred visions. On 21 Dec. 2015, she started the first dose of the SBC002 at a dosage of 0.01-0.02 g/day. She reported a strong energy field at the back of her two eyes.

On Day 5 after the first dosage, she could see her fingers in front of her eyes.

On Day 17, she could see the chopsticks moving when eating while she could not see them before. On the same day, she visited Taichung Hospital, Ministry of Health and Welfare, VEP study (by goggle method) showed prolonged latency and dampened waveform of P100 response in left or right eye stimulation respectively (the measured latency: left=190.3 ms; right=190.8 ms). Fundus photography showed no apparent retinopathy.

On Day 27, she could see a white paper within 30 cm distance, could identify day and night, zebra crosswalk on the street, and outline of buildings. She could see colors of red, white, black and orange; and she could see the street lights in the evening.

On Day 32, RNFL Thickness Average Analysis showed 32 μm (OS); 38 μm (OD).

On Day 120, her brain MRI showed the Sylvian fissures and cerebral sulci were not widened. The ventricles were not dilated. Her brain MRI did not make a diagnosis of "cortical atrophy".

About 14 months after SBC002 treatment, RNFL Thickness Average Analysis showed 71 μm (OS); 49 μm (OD).

9. Comments

Before taking SBC002, from 2002 to 2015, the 50-year-old female patient had been suffering with multiple sclerosis and related complications for 13 years. She had left optic atrophy for 7 years and right optic neuritis for 8 years; cortical atrophy for 2.5 years. In August 2008, her VEP studies showed none pickup of VEP wave in left or right eye stimulation. RNFL in left eye was undetectable (<10 μm). Even though she had been treated for 5 years with steroids, interferon, immunosuppressive therapy, the course of the multiple sclerosis progressed to a neurodegenerative nature.

About 5 days of taking SBC002 her vision partially recovered; after 17 days, VEP studies showed P100 waves in left or right eye came back, indicating the recovery of function of optic nerves in both sides; after 32 days, her RNFL in left eye was increased from <10 μm to 32 μm; after 14 months, her RNFL thickness was increased to 71 μm. Her brain cortical atrophy disappeared after 4 months of herb B treatment. The main concomitant medication, hydroxychloroquine sulfate has a warning of irreversible retinal damage, retinopathy with changes in pigmentation and visual field defects. Examining carefully the important events before her vision recovery in the context of 13 years' progressive disease and optic atrophy, her recovery in vision and cortex was unlikely to be explained by the natural disease course. Based on the unexpected vision recovery in this case and clear temporal relationship, the direct causal role of SBC002 in the recovery of optic atrophy and cortical atrophy was concluded.

Example III-2 Case SBC002-002

This case refers to a female patient with the date of birth on 22 Jun. 1966. In February 2016, she had a stroke (cerebral hemorrhage). After the stroke, she recovered soon but with remaining symptoms of hemianopia. She could not sleep well in the evening and could only sleep for 2-3 hours intermittently. She took SBC002 10 mg. In the evening of taking this herb, she slept during the whole night for 8 hours till being woken up by a morning call.

Example III—3 an Observational Case Study on the Effect and Safety of an Herbal Mixture (SBC001) which Contains SBC002

Unmet medical needs exist for the treatment of neurological diseases including multiple sclerosis (MS), optic neuritis (ON), Acute Inflammatory Demyelinating Polyneuropathy (AIDP), and cranial nerve diseases. A retrospective and prospective case chart review study has been conducted to observe the clinical efficacy and safety of herb mixture, named as SBC001 (containing about 5-10% of SBC002), which was used as a key ingredient for the treatment of neurological diseases.

Nine patients well-documented with hospital records were collected retrospectively (n=8), or prospectively (n=1). Information regarding disease onset date, hospital diagnosis and treatment, symptoms, efficacy and safety were collected and recorded. For the one patient prospectively followed, a diary recording daily symptoms was used to collect the patient reported outcome. Descriptive analysis was performed for all parameters.

The onset age of diseases was 14-71 years. Male: female ratio was 4:5. Five patients had MS, 2 patients had AIDP, and 2 patients had cranial nerve palsy. Eight patients had visual symptoms; 6 patients had symptoms of limb weakness or numbness. Duration of diseases before the treatment varied from 4 days to 5 years, with the majority (6/9)<6 months. All patients were diagnosed by hospitals supported by clinical course, symptoms, neurological examinations, and MRI findings.

Of them, 6/9 patients had been heavily treated by hospital standard therapies (steroids, immunosuppressant, nonsteroidal anti-inflammatory drugs); and 3/9 patients had been provided with nutritional or supportive therapies (e.g. vitamins). Of them 6/9 patients' symptoms temporarily improved after hospital treatment however relapsed, so they had sought for alternative medicines; and 3/9 patients did not respond to hospital treatment. Equivalent dosage of SBC002 contained in SBC001 was 0.05-0.2 g/time, 3-5 times/day. Six patients were treated with this herb mixture only; 3 patients were concomitantly used with steroids for about 2 weeks, and then took the herb mixture. Of them, 7 patients could comply to the treatment regime; and 2 were not able to follow the treatment regime.

Totally 7/9 patients had a complete recovery of their symptoms after this herb treatment; 1/9 patients had improvement; 1/9 did not respond. Time to effect was 1 day to 2 months. Time to complete recovery was 25 days to 6 months.

Visual symptoms (n=8): 6/8 patients with visual symptoms completely recovered within 25 days to 6 months; and time to effect was 1 day to 2 months. 1 patient did not improve; 1 patient improved.

Limb symptoms (n=6): 3/6 patients with limb weakness or numbness completely recovered within 3-6 months. The time to effect was 1 day to 1.5 month.

Medical image (n=3): of the 3 patients with paired brain MRI results before and after treatment, 2 of them indicated with MRI improvement.

Four patients also reported a memory improvement after 1-2 months.

Off-treatment sustainability: Till the last follow up, 6 patients with a complete recovery and discontinued the treatment. Of the 6 patients, they had reported a symptom free survival for 1.5 years, 1.5 years, 3.8 years, 4.5 years, 4.5 years, 22 years, respectively.

In 5 patients, they self-discontinued the treatment and symptoms relapsed quickly; after resuming the treatment, their symptoms improved again. The positive dechallenge and positive rechallenge indicated the causal relationship between the symptoms improvement with this treatment could not be ruled out.

In general, the herbal mixture (SBC001) containing SBC002 was safe and well tolerated. One patient had reported vomiting at the beginning of treatment and resolved after treatment interruption for 3 days. No other adverse events or toxicity had been observed. Based on the observational case review, this herbal mixture (SBC001) containing SBC002 indicated clinical benefits for patients with MS, ON, AIDP, cranial nerve disease and other neurological diseases, with a favorable safety profile.

Case Studies of Healthy Volunteers Treated with SBC002

Example III-4 Case SBC002-003

The case refers to a healthy male subject with date of birth on 12 Sep. 1974. At the first time, after 10-30 minutes of taking SBC002 0.005 g, he felt his vision became more bright and clear. His memory and reaction speed also increased.

Example III-5 Case SBC002-004

The case refers to a healthy female subject with date of birth 16 May 1983. At the first time after taking SBC002 0.002 g, she felt her mind state was clearer and her thoughts were quicker.

Example III-6 Case SBC002-005

The case refers to a healthy male subject with date of birth 4 Jul. 1977. At the first time after taking SBC002 0.005 g, he felt his vision became more bright and clear. His memory became better, and his reaction was faster.

Example III-7 Case SBC002-006

The case refers to a healthy male subject with date of birth 30 Jul. 1970. On the first day (15 Jan. 2016) after first dosing of SBC002 0.01 g, he felt his vision was brighter, visual acuity was higher; felt fatigue in his eyes after long time of watching computers was reduced; and felt the pressure inside his eyes was reduced. He felt faster and clearer thinking which lasted for 5 days.

Example III-8 Case SBC002-007

This case refers to a female subject with 900-950 degrees of myopia in both eyes with date of birth 29 Jul. 1974. On the first day after first dosing 0.01 g, in 20 minutes, she felt her left eye was surrounded by hot energy, in 30 minutes her right eye was surrounded by hot energy as well, in 40 minutes, the whole brain was enriched with hot energy and she started to feel very quiet mind status. Afterwards, she took 0.01 g/day, she reported that she did not feel vision fatigue after 7 hours of working (before she often felt vision fatigue after 4-5 hours of staring at computers). She felt clearer vision acuity and less vision fatigue after one month of SBC002 treatment. After discontinuation of SBC002, her vision acuity decreased and her vision fatigue was similar as before taking SBC002.

Examples (IV) OF Herb B Extracts (SBC002) in Celluar Models

Example IV-1 of Herb B Extracts

The effects of Herb B (SBC002) Extracts in mouse primary neuron models when added 48 hours prior to AβO treatment or without AβO treatment The aim of this study is to determine whether extracts of herb B might rescue neuronal death in in vitro neuron models. For that purpose, the neuro-protective effects of herb B extracts at six concentrations were investigated using mouse primary cortical neurons challenged with Aβ1-42 oligomers (AβO). β-Amyloid peptide triggers a variety of pathological changes finally leading to neuronal dysfunction and degeneration in multiple neurological diseases including AD.

Cortical neurons from embryonic day 16-17 are prepared from C57BL6/J mouse fetuses. In brief, dissociated cortical cells are plated (50.000 cells/well) in 48-well plates pre-coated with 1.5 µg/mL polyornithine (Sigma). Cells are cultured in a chemically defined Dulbecco's modified eagle's/F12 medium free of serum and supplemented with hormones, proteins and salts. Cultures are kept at 35° C. in a humidified 6% $CO_2$ atmosphere. Mouse cortical neurons were exposed for 24 h to 1.0 μM AβO after a 48-h pre-incubation with vehicle or different concentrations of herb B extracts. The AβO-induced neurotoxicity was evaluated using the MTT assay.

Preparation of Herb B Extracts:
I. prepare the stock solution (10 mg/ml), add 1 ml DMSO into herb B (10 mg) in 1.5 ml eppendorf tube, then rotate the eppendorf tube overnight at a temperature of 30-37° C.
II. take the supernatant (stock solution), then dilute the solution to 1000-fold by cell culture medium; the highest dose solution is obtained (10 μg/ml).
III. dilute the highest dose solution by 3-fold series dilution using cell culture medium to achieve the other 5 dosages of 3.2 μg/ml, 1 μg/ml, 320 ng/ml, 100 ng/ml, 32 ng/ml.

As expected, the incubation of cortical neurons with 1.0 μM AβO for 24 h resulted in a decreased cell viability by 48.6±1.4%. DHA (0.05 μM, used as a positive control) reduced AβO-induced neuronal death with a remaining cell viability of 82.0±2.6% of control. These control data demonstrate that: i) as expected, DHA protects neuronal cells, and ii) cells challenged with AβO can be successfully rescued, verifying the test system.

Neurons were pre-incubated with different concentrations of herb B extracts for 48 h and thereafter treated for 24 h with 1 μM AβO. The results were that in the presence of different concentrations of herb B extracts resulted in dose-dependent neuroprotective effect (FIG. 10 right and FIG. 11). The neuroprotective effect was 100% at all concentrations (cell viability of 119.5±6.4%).

When neurons pre-incubated for 48 h with different concentrations of herb B extracts only, showed a higher cell viability of 111.4±3.2% or 112.9±4.1% at 32 or 10000 ng/mL of herb B extracts, respectively (FIG. 10 left).

In conclusion, the data suggest that herb B extracts offer a strong protection toward AβO-induced neurotoxicity. A neuronal-growth-stimulating effect of herb B extracts is observed.

Example IV-2 of Herb B Extracts

The Effects of Herb B Extracts in Mouse Primary Neuron when Added Concomitantly, or 3 and 6 Hours after AβO Treatment The aim of this study is to determine whether Herb B extracts might rescue neuronal death in vitro neuron models. For that purpose, the neuro-protective effects of Herb B extracts at six concentrations were investigated using mouse primary cortical neurons challenged with Aβ1-42 oligomers (AβO). Treatments were added at different time points (concomitantly T0 and T3, or T6 after AβO) with the aim to identify rescuing effects or anti-apoptotic effects.

Cortical neurons from embryonic day 16-17 are prepared from C57Bl6/J mouse fetuses, as described in Example IV-1. Herb B extracts was similarly prepared as above described in Example IV-1.

Herb B extracts were added into mouse primary cortical neurons at different time points (concomitantly T0, T3, or T6 after AβO). Mouse cortical neurons were exposed for 24 h to 1.0 μM AβO. The AβO-induced neurotoxicity was evaluated using the MTT assay. As expected, the incubation of cortical neurons with 1.0 μM AβO for 24 h resulted in a decreased cell viability (50.9±2.0%, 51.3±2.0% and 51.7±4.2% for plates 1, 2 and 3 respectively). (FIG. 12).

Figure 12:
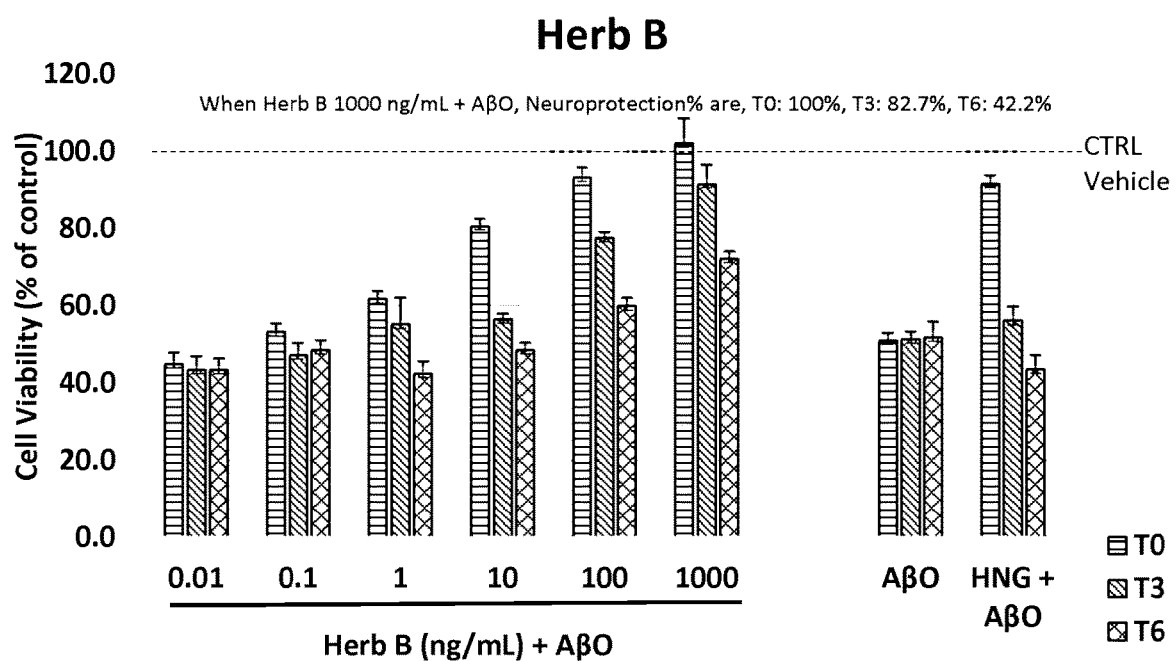
FIG. 12 relates to Examples IV-2 and shows neuroprotective, anti-apoptotic and neuro-rescuing effects of Herb B extracts in mouse primary neuron when added concomitantly, or 3 or 6 hours after A$\beta$O treatment.

As expected, humanin peptide (HNG, positive control) added at T0 strongly reduced AβO-induced neuronal death with a remaining cell viability of 91.6±2.1% of control (FIG. 12). When added 3 or 6 h after AβO, HNG did not prevent cell death in agreement with historical data. These control data demonstrate that: i) as expected, HNG protects neuronal cells only when added concomitantly to AβO, and ii) cells challenged with AβO can be successfully rescued, verifying the test system.

Neurons were treated with different concentrations of herb B extracts added concomitantly to AβO (T0), 3 h after AβO (T3), or 6 h after AβO (T6). The results were: for herb B extracts: in all experimental conditions (i.e. T0, T3 and T6), herb B extracts showed dose-dependent neuroprotective effects. Herb B extracts completely prevented AβO-induced cell death when added concomitantly to AβO (cell viability of 93.3±2.5% and 102.2±6.3% at concentrations of 100 or 1000 ng/mL, respectively). Moreover, herb B extracts protected AβO-induced neuron death when added 3 h after AβO (cell viability of 77.5±1.5% and 91.6±4.9%, at concentrations of 100 and 1000 ng/ml, respectively) and when added 6 h after AβO (cell viability of 59.9±2.2% and 72.1±2.0%, at concentrations of 100 and 1000 ng/ml, respectively). (FIG. 12)

The percentage of neuroprotection and anti-apoptosis effects was defined as: (neuron viability of herb B extract group−neuron viability of toxin treated group)/(100−neuron viability of toxin treated group)×100%. The % of neuroprotection and anti-apoptotic effects of herb B extract at 1000 ng/ml is 100%, 82.7%, 42.2%, at T0, T3, or T6, respectively. (FIG. 12)

In conclusion, the data suggest that herb B extracts offer a strong protective, anti-apoptotic and neuro-rescuing effects toward AβO-induced neurotoxicity. Herb B extracts discriminate from humanin that it was more potent than humanin to prevent and rescue AβO-induced neuronal death.

Example IV-3 of Herb B Extracts

The Effects of Herb B Extracts in AβO Treated Human Induced Pluripotent Stem Cells (iPSC) when Added Concomitantly or 3 and 6 Hours after AβO Treatment To determine whether Herb B extracts might rescue neuronal death in human iPSC-derived neurons challenged with Aβ1-42 oligomers (AβO). In this cellular model, AβO induce a dramatic neuronal death that could be monitored by the level of neuronal specific enolase (NSE) using a specific ELISA assay. Herb B extracts would be added at different time points (concomitantly and after AβO) with the aim to identify rescuing effects.

Cells (HIP-Neuronal progenitors, GlobalStem, Cat #GSC-4312, Lot #20010260) were plated in 96-well plates at a density of 60.000 cells per well and culture. Before experiments, cells were matured for five weeks and kept at 37° C. in a humidified 5% $CO_2$ atmosphere.

Herb B extracts was similarly prepared as above described in Example IV-1.

Cells were incubated with vehicle or 1 μM AβO in the absence or presence of different concentrations (i.e. 10, 100, 1000 and 10000 ng/ml) of Herb B extracts added concomitantly to AβO (T0), 3 h after AβO (T3), or 6 h after AβO (T6). Cells are incubated for 24 h in a final volume of 100 μL per well. For positive control, cells are treated similarly in the presence of 0.1 µM HNG (i.e. S14G variant of humanin peptide). In addition, neuronal loss was monitored using the detection of neuronal specific enolase (NSE) by ELISA according to supplier's recommendations (Clone-Cloud, Cat #SEA537Hu). A total of six data points per experimental condition was generated here.

Human iPSC was exposed for 24 h with 1.0 µM AβO. The AβO-induced neurotoxicity was evaluated using the NSE assay. As expected, the incubation of neurons with 1.0 µM AβO for 24 h resulted in a decreased cell viability of 49.7±5.5%, 37.5±3.0% and 46.9±1.9% for plates 1, 2 and 3 respectively.

As expected, humanin peptide (HNG, positive control) added at T0 strongly reduced AβO-induced neuronal death with a neuron viability of 85.3±5.6%. When added 3 or 6 h after AβO, HNG did not prevent cell death in agreement with historical data. These control data demonstrate that: i) as expected, HNG protects neuronal cells only when added concomitantly to AβO, and ii) cells challenged with AβO can be successfully rescued, verifying the test system. (FIG. 13)

IPSCs were treated with different concentrations of Herb B extracts added concomitantly to AβO (T0), 3 h after AβO (T3), or 6 h after AβO (T6). The results were as follows: Herb B extracts in all experimental conditions (i.e. T0, T3 and T6), showed dose-dependent neuroprotective effects.

For a concentration of 100, 1000, 10000 ng/mL, Herb B extracts prevented AβO-induced cell death when added concomitantly to AβO (cell viability of 69.0±6.3%, 72.7±2.4% or 78.6±5.4%, respectively); when added 3 h after AβO (cell viability of 70.6±7.7%, 71.1±3.4%, 86.0±6.1%, respectively) and when added 6 h after AβO (cell viability of 56.6±5.0%, 53.9±14.9%, 74.9±6.7%, respectively). The % of neuroprotection and anti-apoptotic effects of herb B extract at 1000 ng/ml is 57.4%, 77.6%, 52.8%, at T0, T3, or T6, respectively. (FIG. 13a, 13b, 13c) In conclusion, the data suggest that Herb B extracts offer a strong protective, anti-apoptotic and neuro-rescuing effects toward AβO-induced neurotoxicity in human neurons derived from iPSC. Herb B extracts discriminate from humanin as it was more potent than humanin to inhibit AβO-induced toxicity in this cellular model.

Example IV-4 of Herb B Extracts

The Effects of Herb B Extracts in Multiple Neuron Toxins Treated Mouse Primary Neuron Models—when Added at 3 Hours after Toxins Treatment To determine whether Herb B extracts might rescue neuronal death in multiple toxin stressed in vitro models. The neuro-protective effects of different concentrations of Herb B extracts was investigated using mouse primary cortical neurons challenged with different types toxins. Herb B extracts was added three hours (T3) after toxins with the aim to identify rescuing effects. Cell viability was investigated using the MTT assay after a 24-h incubation of cells with toxins.

Cortical neurons from embryonic day 16-17 are prepared from C57B16/J mouse fetuses, as described in Example IV-1. Herb B extracts was similarly prepared as described in Example IV-1.

Stable oligomeric or fibrillar preparations are prepared according to historical protocols. The source of the different toxins is as follow:

A$\beta_{25-35}$ fibrils from Bachem (H1192).
Human Tau (2N4R) protein from Evotec.
Human α-synuclein from r-Peptide (ref 0101008603).
Amylin obtained from Bachem (ref H-7905.1000).
Prion protein$_{118-135}$ from Bachem (ref H-4206).

All treatments are done in triplicates in 48-well plates at DIV 6/7. Cells were incubated with vehicle or toxins (at the indicated final concentrations) in the absence or presence of different concentrations of herb B extracts (1000, 10000 ng/ml) added 3 h after toxins (T3). Cells were incubated for 24 h in a final volume of 140 µL per well.

The positives control (added at T3) used was 0.104 HNG (S14G variant of humanin peptide) as a well-known antiapoptotic peptide.

Cells were incubated for 24 h before monitoring cell viability using the MTT assay. Briefly, cells were incubated at 35° C. for 1 h with MTT (Sigma, Cat #M2128-10G, Lot #MKBH7489V). For that purpose, 14 µL of 5 mg/mL MTT (solubilized in PBS) are added in each well. After incubation, medium was removed and cells were lyzed with 150 µL DMSO for 10 minutes and protected from light. After complete solubilization of formazan, absorbance at 570 nm is recorded using a Spectrophotometer BMG Labtech Fluostar Omega.

The percentage of neuroprotection and anti-apoptosis effects of herb B extracts was defined as the (neuron viability of herb B extracts group–neuron viability of toxin treated group)/(100–neuron viability of toxin treated group)×100%.

Figure 14A:
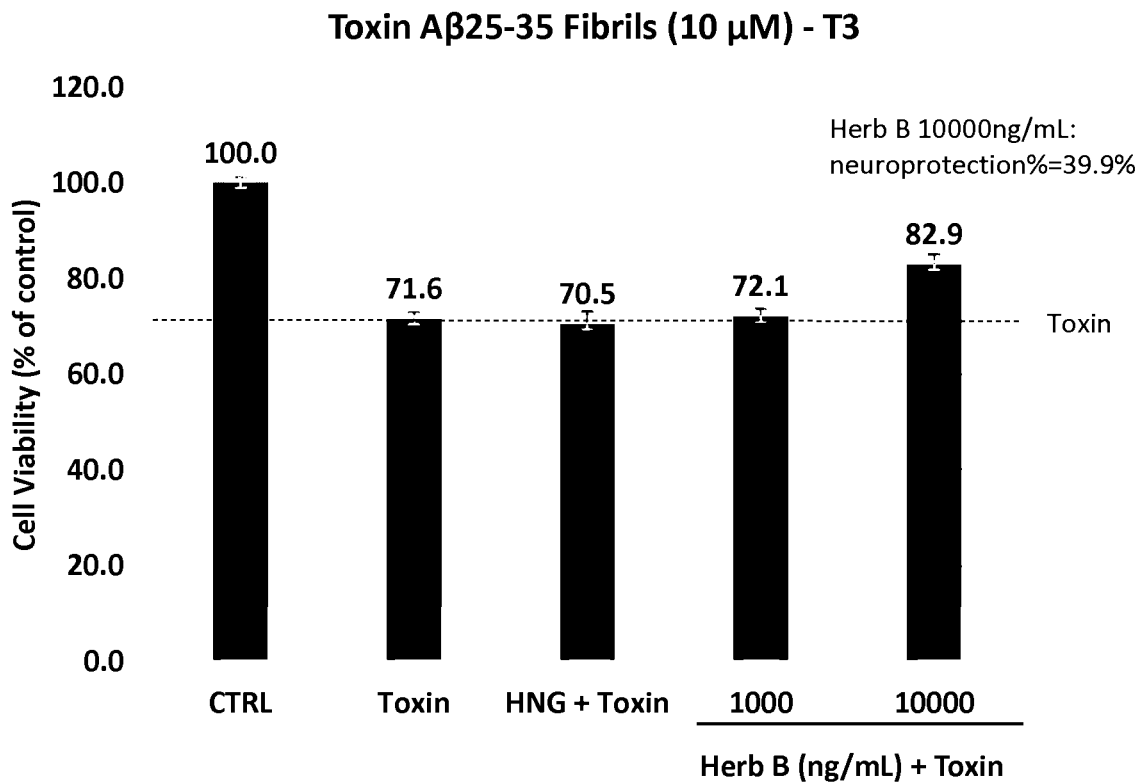
FIGS. 14a to 14f, relate to Examples IV-4 and show neuroprotective, anti-apoptotic and neuro-rescuing effects of Herb B extracts in multiple neuron toxins treated mouse primary neuron models—when added at 3 hours after toxin treatment.

Herb B extracts showed anti-apoptotic and neuroprotective effects against 10 µM Aβ25-35 fibrils at a concentration of 10000 ng/ml with a cell viability of 82.9±2.2%, resulting in 39.9% protection (FIG. 14a).

Figure 14B:
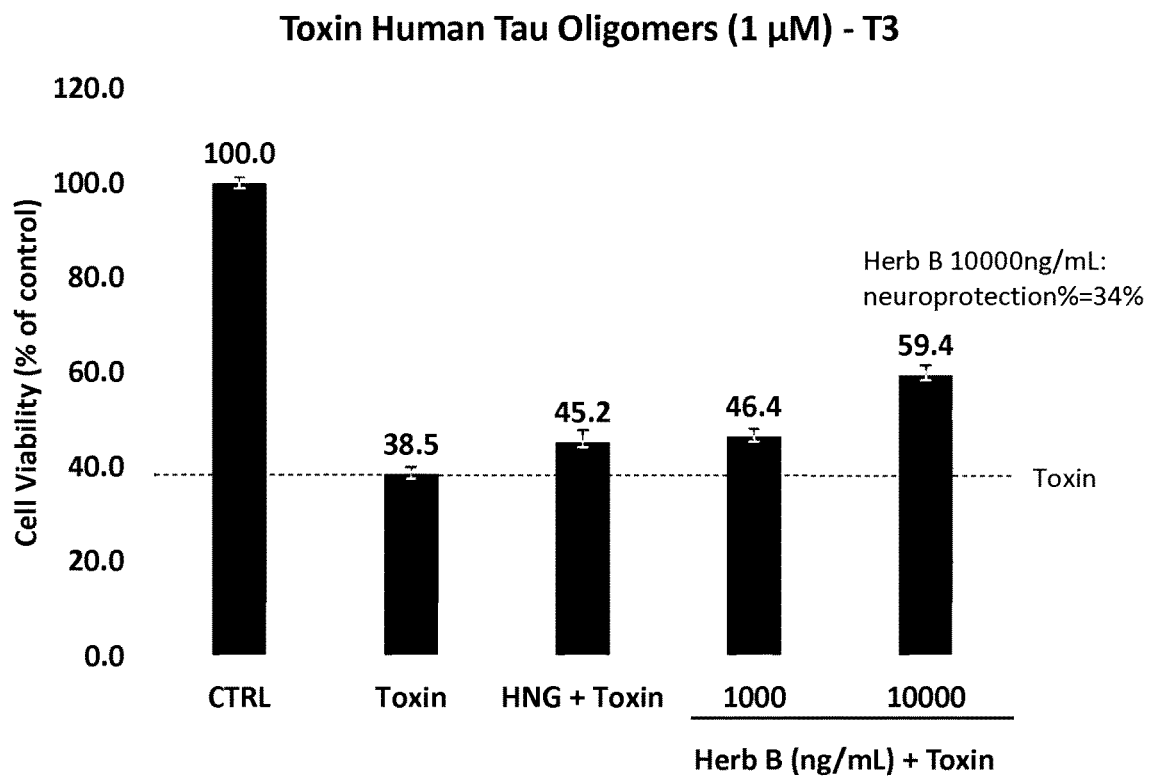

Herb B extracts showed dose-dependent anti-apoptotic and neuroprotective effects against 1 µM human tau oligomers, with the maximal effect at concentration of 10.000 ng/mL with a cell viability of 59.4±2.1%, resulting in 34.0% protection. (FIG. 14b).

Figure 14C:
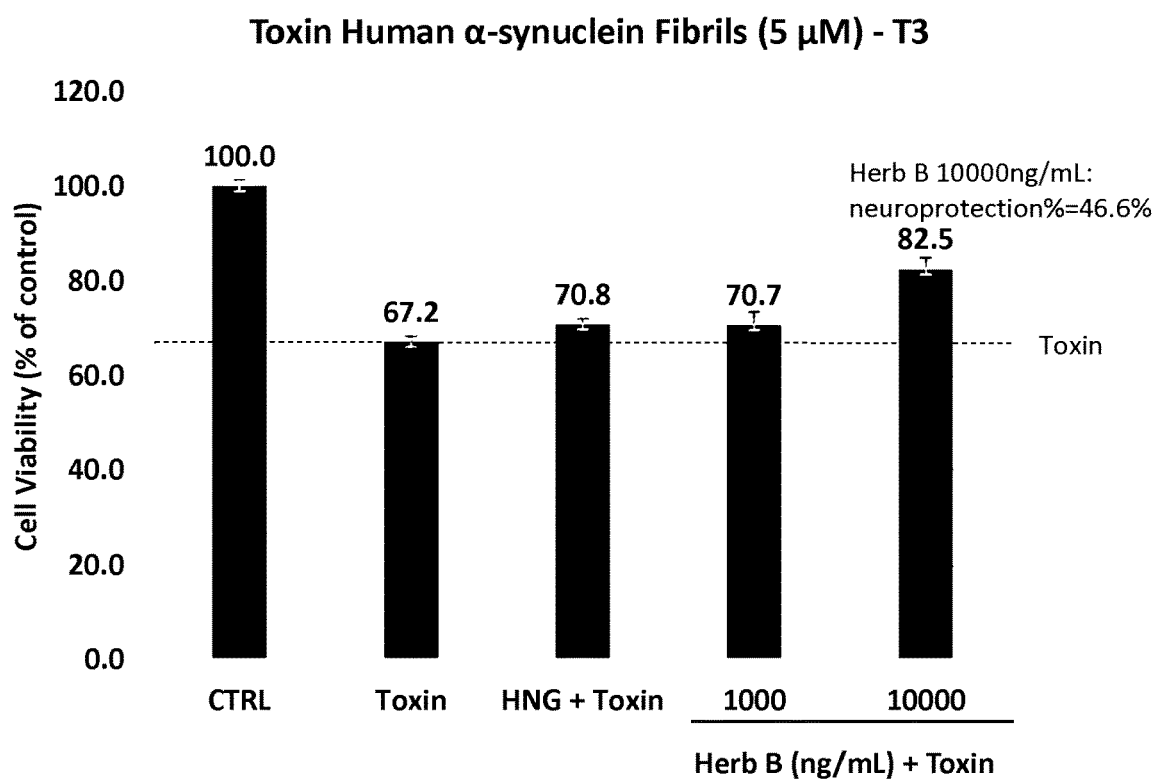
Figure 14D:
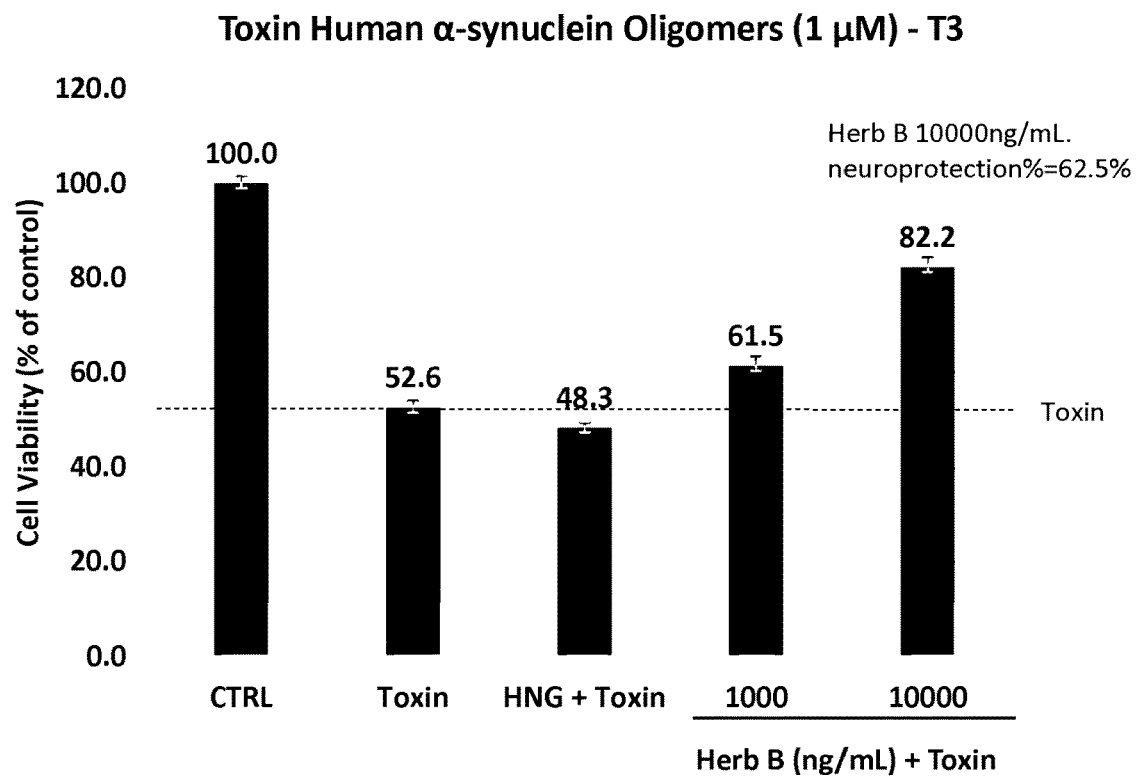

Herb B extracts showed dose-dependent anti-apoptotic and neuroprotective effects against α-synuclein fibrils and α-synuclein oligomer, with the maximal effect at a dose of 10.000 ng/mL, with a cell viability of 82.5±2.6% and 82.2±2.2%, resulting in 46.6% and 62.5% protection, respectively (FIGS. 14c and 14d).

Figure 14E:
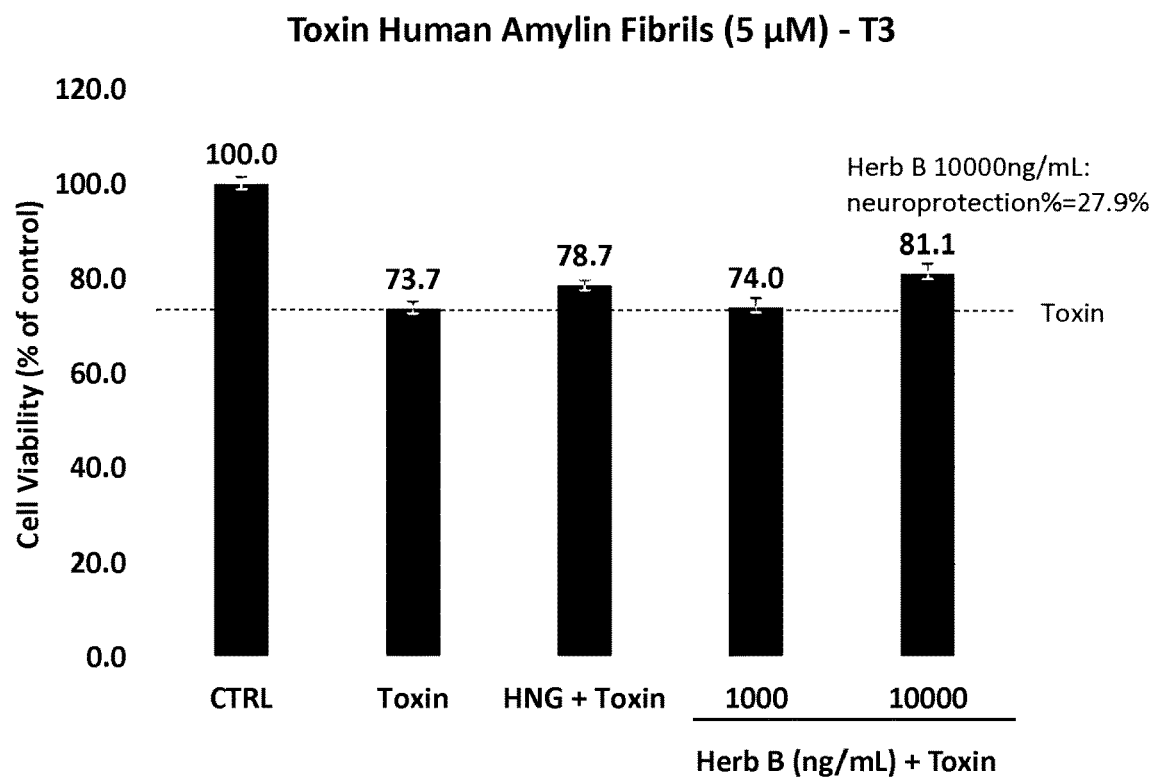

Herb B extracts showed anti-apoptotic and neuroprotective effects against 5 µM amylin fibrils with the maximal effect at a concentration of 10.000 ng/mL, with a cell viability of 81.1±2.5%, resulting in 27.9% protection (FIG. 14e).

Figure 14F:
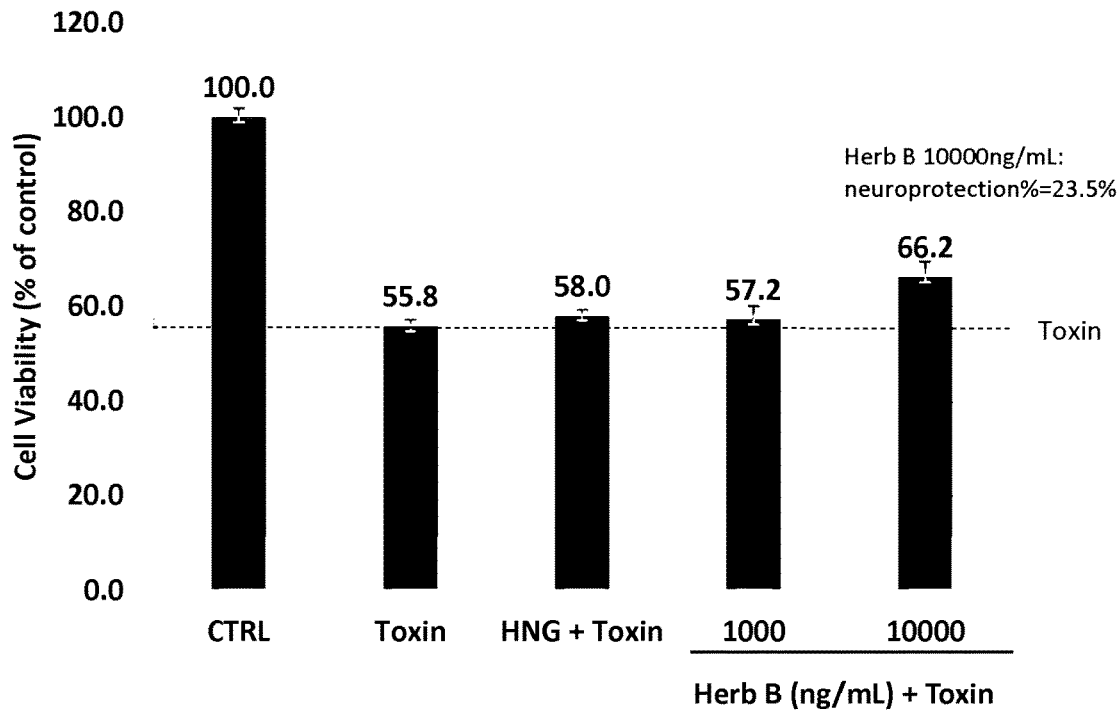

Herb B extracts showed anti-apoptotic and neuroprotective effects against 2 µM Prion 118-135 oligomers with the maximal effect at a concentration of 10.000 ng/mL, with a cell viability of 66.2±3.3%, resulting in 23.5% protection (FIG. 14f).

In conclusion, the study has demonstrated that herb B extracts offers a strong protection, neuro-rescuing and antiapoptotic effect toward Aβ25-35 fibrils-, human tau oligomer-, human tau fibrils-, human alpha-synuclein oligomer-, alpha-synuclein fibrils-, human amylin fibrils- and prion oligomers-induced neurotoxicity in mouse primary cortex neurons. Herb B extracts discriminates from humanin as it is more potent than humanin to inhibit multiple toxins-induced neuron deaths in these cellular models.

Example IV-5 of Herb B Extracts

The Effects of Herb B Extracts in H$_2$O$_2$ Treated Mouse Primary Neuron Models—when Added at 48 Hours Before or 3 Hours after Toxins Treatment To determine whether Herb B extracts might rescue neuronal death in H$_2$O$_2$ stressed in vitro models. Herb B extracts was added at 48 hours before or three hours (T3) after toxins with the aim to identify rescuing effects. Cell viability was investigated using the MTT assay after a 24-h incubation of cells with toxins.

Cortical neurons from embryonic day 16-17 are prepared from C57B16/J mouse fetuses, described in Example IV-1. Herb B extracts was similarly prepared as above described in Example IV-1. 1 mM Trolox (Sigma, ref 238813) was used as a well-known antioxidant agent.

Mouse primary cortical neurons were treated for 24 h with 0.25 mM $H_2O_2$. Herb B extracts or Trolox were added at 3 hours after $H_2O_2$ treatment. Neurotoxicity of toxins was evaluated using the MTT assay. As expected, the incubation of cells with toxins for 24 h resulted in a decrease of cell viability of 36.2±3.0% for $H_2O_2$, respectively. Trolox, added at $T_3$ and used as a positive control, partially inhibited cell death induced by $H_2O_2$. When added at 3 h after $H_2O_2$, Herb B extracts induced a dose-dependent neuroprotection with a maximal effect at a dose of 10.000 ng/mL with a cell viability of 56.8±2.4%. The % of neuroprotection and anti-apoptotic effects of herb B extract at 10000 ng/ml is 32.2%. (FIG. 15a)

Mouse primary cortical neurons were incubated with vehicle or different concentrations of herb B extracts or 1 mM Trolox added 48 hours, then neurons were treated for 24 h with 0.25 mM $H_2O_2$. Neurotoxicity of $H_2O_2$ was evaluated using the MTT assay. As expected, the incubation of cells with $H_2O_2$ for 24 h resulted in a decreased cell viability of 61.7±2.5%. Trolox (1 mM), added 48 h before $H_2O_2$ partially inhibited cell death induced by $H_2O_2$. When preincubated for 48 h before $H_2O_2$, Herb B extracts prevented $H_2O_2$-induced cell death at a dose of 10.000 ng/mL with a cell viability of 76.7±2.4%. The % of neuroprotection and anti-apoptotic effects of herb B extract at 10000 ng/ml is 39.2%. (FIG. 15b)

In conclusion, the data suggest that Herb B extracts offer a protective, and anti-oxidative effects toward $H_2O_2$-induced neurotoxicity when added at 48 hours before $H_2O_2$ treatment or added at 3 hours after adding $H_2O_2$.

Example IV-6 of Herb B Extracts

The effects of Herb B extracts in Camptothecin treated mouse primary neuron models—when added at 48 hours before Camptothecin treatment The neuro-protective effects of different concentrations of Herb B extracts was investigated using mouse primary cortical neurons challenged with camptothecin, which is a cytotoxic quinoline alkaloid which inhibits the DNA enzyme topoisomerase I (topo I).

Cortical neurons from embryonic day 16-17 are prepared from C57B16/J mouse fetuses, as described in Example IV-1. Camptothecin is obtained from Sigma, (ref C9911—(S)-(+)-Camptothecin). Herb B extracts was similarly prepared as above described in Example IV-1.

Cells were incubated with vehicle or toxins (at the indicated final concentrations described in plate-layout below) in the absence or presence of different concentrations of compound C added 48 hours before toxin's challenge. After the addition of 1 μM camptothecin, cells were further incubated for 24 h in a final volume of 140 μL per well.

As expected, the incubation of cells with 1 μM camptothecin for 24 h resulted in a decreased cell viability of 57.7±1.6% of control. When preincubated for 48 h before camptothecin-treatment, Herb B extracts induced a dose-dependent neuroprotection, with a maximal effect at a dose of 10.000 ng/mL. Cell viability was of 84.0±6.4% of control. The % of neuroprotection and anti-apoptotic effects of herb B extract at 10000 ng/ml is 62.1%. Interestingly, the neuroprotective effect of Herb B extracts appeared to be bi-phasic. Indeed, the neuroprotective effect of Herb B extracts at a dose of 10 ng/mL was below the effects of Herb B extracts at doses of 1 and 100 ng/mL. (FIG. 16)

In conclusion, the data suggest that Herb B extracts offer strong protection, neuro-rescuing and anti-apoptotic effects toward neuronal death induced by camptothecin.

The invention claimed is:

1. A method for the treatment of a disease, said method comprising:
administering an effective amount of a compound of formula (I) or a pharmaceutically acceptable salt thereof to a subject in need thereof

wherein $R^1$, $R^2$ and $R^3$ are —C(O)$R^4$, with $R^4$ being $C_{14}$-alkyl,
wherein said disease is at least one selected from the group consisting of retinal degenerative diseases and optic nerve degenerative diseases.

2. The method of claim 1, wherein said retinal degenerative diseases and optic degenerative diseases are selected from the group consisting of optical atrophy, Leber's hereditary optic neuropathy, dominant optic atrophy, age-related macular degeneration, glaucoma, and retinitis pigmentosa.

3. The method of claim 1, wherein said compound of formula (I) is administered in a dosage from 1 mg/day to 1000 mg/day to said subject in need thereof.

* * * * *

UNITED STATES PATENT AND TRADEMARK OFFICE
CERTIFICATE OF CORRECTION

PATENT NO. : 11,406,616 B2
APPLICATION NO. : 16/307663
DATED : August 9, 2022
INVENTOR(S) : Yuhong Dong, Chun-Hsiung Chang and Sheng-Tang Lin It is certified that error appears in the above-identified patent and that said Letters Patent is hereby corrected as shown below:

On the Title Page

Column 1, Line 2 in the INVENTORS currently reads:
"Taiwan (TW);"
And should read:
--Taiwan (CN);--;

Column 2, Line 1 Item (56) in the FOREIGN PATENT DOCUMENTS currently reads:
"1 244 722"
And should read:
--1 244 772--;

Column 2, Line 8 Item (56) in OTHER PUBLICATIONS currently reads:
"Sep. 29, 2017."
And should read:
--Sep. 26, 2017.--;

(Pg. 2), Column 1, Line 7 Item (56) in OTHER PUBLICATIONS currently reads:
"Disease,", J. Am."
And should read:
--Disease," J. Am.--;

(Pg. 2), Column 2, Line 13 Item (56) in OTHER PUBLICATIONS currently reads:
"Sweeney et al.,"
And should read:
--Sweeny et al.,--;

(Pg. 2), Column 2, Line 35 Item (56) in OTHER PUBLICATIONS currently reads:
"PLos One;"

Signed and Sealed this
First Day of November, 2022

Katherine Kelly Vidal
*Director of the United States Patent and Trademark Office*

And should read:
--PLoS One;--.